(12) United States Patent
Nagai et al.

(10) Patent No.: US 9,174,935 B2
(45) Date of Patent: *Nov. 3, 2015

(54) TRANSITION METAL COMPLEXES OF BIS[THIOHYDRAZIDE AMIDE] COMPOUNDS

(75) Inventors: Masazumi Nagai, Lexington, MA (US); Jianhua Shen, Andover, MA (US)

(73) Assignee: Synta Pharmaceuticals Corp., Lexington, MA (US)

(*) Notice: Subject to any disclaimer, the term of this patent is extended or adjusted under 35 U.S.C. 154(b) by 464 days.

This patent is subject to a terminal disclaimer.

(21) Appl. No.: 13/125,003

(22) PCT Filed: Oct. 21, 2009

(86) PCT No.: PCT/US2009/061480
§ 371 (c)(1),
(2), (4) Date: Aug. 16, 2011

(87) PCT Pub. No.: WO2010/048284
PCT Pub. Date: Apr. 29, 2010

(65) Prior Publication Data
US 2011/0294877 A1    Dec. 1, 2011

Related U.S. Application Data

(60) Provisional application No. 61/196,932, filed on Oct. 22, 2008.

(51) Int. Cl.
| | | |
|---|---|---|
| *A61K 31/30* | (2006.01) | |
| *A61P 35/00* | (2006.01) | |
| *A61K 31/28* | (2006.01) | |
| *C07C 327/56* | (2006.01) | |
| *C07D 213/83* | (2006.01) | |
| *C07D 231/14* | (2006.01) | |
| *C07D 307/68* | (2006.01) | |

(52) U.S. Cl.
CPC ............ *C07C 327/56* (2013.01); *C07D 213/83* (2013.01); *C07D 231/14* (2013.01); *C07D 307/68* (2013.01); *C07C 2101/02* (2013.01)

(58) Field of Classification Search
USPC ........................................................ 514/499
See application file for complete search history.

(56) References Cited

U.S. PATENT DOCUMENTS

| | | | |
|---|---|---|---|
| 6,762,204 B2 | 7/2004 | Koya et al. | |
| 6,800,660 B2 | 10/2004 | Koya et al. | |
| 6,825,235 B2 | 11/2004 | Chen et al. | |
| 6,924,312 B2 | 8/2005 | Koya et al. | |
| 7,001,923 B2 | 2/2006 | Koya et al. | |
| 7,037,940 B2 | 5/2006 | Koya et al. | |
| 7,074,952 B2 | 7/2006 | Chen et al. | |
| 7,345,094 B2 | 3/2008 | Koya et al. | |
| 7,368,473 B2 | 5/2008 | Koya et al. | |
| 7,385,084 B2 | 6/2008 | Koya et al. | |
| 7,435,843 B2 | 10/2008 | Chen et al. | |
| 7,579,503 B2 | 8/2009 | Koya et al. | |
| 7,645,904 B2 | 1/2010 | Chen et al. | |
| 7,652,168 B2 | 1/2010 | Chen et al. | |
| 7,671,092 B2 | 3/2010 | Koya et al. | |
| 7,678,832 B2 | 3/2010 | Lunsmann et al. | |
| 7,709,683 B2 | 5/2010 | Chen et al. | |
| 7,750,042 B2 | 7/2010 | Koya et al. | |
| 7,763,658 B2 | 7/2010 | Koya et al. | |
| 7,795,313 B2 | 9/2010 | Koya et al. | |
| 2006/0142386 A1 | 6/2006 | Barsoum | |
| 2006/0142393 A1 | 6/2006 | Sherman et al. | |
| 2006/0167106 A1 | 7/2006 | Zhang et al. | |
| 2007/0088057 A1 | 4/2007 | Lunsmann et al. | |
| 2008/0118562 A1 | 5/2008 | Koya | |
| 2008/0119440 A1 | 5/2008 | Koya | |
| 2008/0176828 A1 | 7/2008 | Williams et al. | |
| 2008/0226588 A1 | 9/2008 | McLeod | |
| 2009/0023736 A1 | 1/2009 | Koya et al. | |
| 2009/0042991 A1 | 2/2009 | Barsoum et al. | |
| 2009/0093538 A1 | 4/2009 | Bertin et al. | |
| 2009/0137682 A1 | 5/2009 | Dahl | |
| 2010/0068174 A1 | 3/2010 | Jacobson | |
| 2010/0081635 A1 | 4/2010 | Chen et al. | |
| 2010/0093828 A1 | 4/2010 | Koya et al. | |

(Continued)

FOREIGN PATENT DOCUMENTS

| | | | | |
|---|---|---|---|---|
| JP | 52-15549 A | | 8/1993 | |
| WO | WO 2006009940 A1 | * | 1/2006 | ............ C07C 327/56 |

OTHER PUBLICATIONS

El-Asmy et al., Structural studies on cadmium(II), cobalt(II), copper(II), nickel(II) and zinc(II) complexes of 1-malonyl-bis(4-phenylthiosemicarbazide, Transition Met. Chem., 15:12-15, 1990.*

M. Mohan et al., Synthesis, Characterization and Antitumor Properties of Some Metal Complexes of 2,6-Diacetylpyridine Bis(N4-azacyclic Thiosemicarbazones), J. Inorganic Biochem. 34, 41-54 (1998).

G. F. de Sousa et al., "Structural and Spectral Studies of a Heterocyclic N(4)-Substituted Bis(thiosemicarbazone), H22,6Achexim.H20, Its Heptacoordinated Tin(IV) Complex [Bu2Sn(2,6Achexim)], and its Binuclear Zinc(II) Complex [Zn(2,6Achexim)]2", Polyhedron, 19, 841-847 (2000).

(Continued)

*Primary Examiner* — Jeffrey S Lundgren
*Assistant Examiner* — Zenab Olabowale
(74) *Attorney, Agent, or Firm* — McCarter & English, LLP; Steven G. Davis

(57) ABSTRACT

The present invention is directed to a compound comprising a bis[thiohydrazide amide] or a deprotonated form thereof, complexed to a transition metal cation, wherein the bis[thiohydrazide amide] is represented by Structural Formula (I), or a prodrug, isomer, ester, salt, hydrate, solvate, polymorph or a deprotonated form thereof. In one embodiment, the compound is represented by Structural Formula (II), or a prodrug, isomer, ester, salt, hydrate, solvate or polymorph thereof. The present invention also provides a pharmaceutical composition comprising the compound of the invention and method of use thereof.

24 Claims, 26 Drawing Sheets

(56) References Cited

U.S. PATENT DOCUMENTS

| | | |
|---|---|---|
| 2010/0249239 A1 | 9/2010 | Lunsmann et al. |
| 2010/0280075 A1 | 11/2010 | Koya et al. |
| 2010/0324143 A1 | 12/2010 | Koya et al. |
| 2011/0098476 A1 | 4/2011 | Chen et al. |
| 2011/0196025 A1 | 8/2011 | Kostik et al. |
| 2011/0245262 A1 | 10/2011 | Sun et al. |
| 2011/0245577 A1 | 10/2011 | Koya |
| 2011/0288162 A1 | 11/2011 | Masazumi et al. |
| 2011/0294814 A1 | 12/2011 | Kowalczyk-Prezewloka et al. |
| 2011/0294877 A1 | 12/2011 | Masazumi et al. |
| 2011/0294895 A1 | 12/2011 | Lunsmann et al. |
| 2012/0035266 A1 | 2/2012 | Koya et al. |
| 2012/0065206 A1 | 3/2012 | Jiang et al. |
| 2012/0065235 A1 | 3/2012 | Sun et al. |
| 2013/0035386 A1* | 2/2013 | Nagai et al. .................. 514/494 |

OTHER PUBLICATIONS

Yusupov, V.G. et al., "Copper(II) Complexes with Benzoyl-, thiobenzoylhydrazones and thiosemicarbazones of diacetyl and 1,1-diacetylcyclopropane", *Koordinatsionnaya Khimiya* 16(10), 1350-1354 (1990) (English abstract only).

Agrawal, S. et al., (1986) "Spectroscopic studies of N-salicyl-N'-2-furanthiocarboxy hydrazine and its 3d metal complexes, new potential antitumor agents", *Spectrochimica Acta*, vol. 42A, No. 4, pp. 507-513.

Singh, N.K. et al., (2002) "Antitumor and Immunomodulatory Effects of Cu(II) Complexes of Thiobenzyhdrazide", *Metal-Based Drugs*, vol. 9, Nos. 1-2, pp. 109-118.

\* cited by examiner

TRANSITION METAL COMPLEXES OF BIS[THIOHYDRAZIDE AMIDE] COMPOUNDS

RELATED APPLICATIONS

This application is the U.S. National Stage filed under 35 USC 371 of PCT/US2009/061480, filed Oct. 21, 2009, which claims the benefit of U.S. Provisional Application No. 61/196,932, filed Oct. 22, 2008 end is incorporated herein by reference in its entirety.

BACKGROUND OF THE INVENTION

It has been reported in U.S. Pat. Nos. 6,800,660; 6,762,204; 7,037,940; 7,001,923; and 6,924,312 that certain bis[thiohydrazide amide] compounds significantly enhance the anti-cancer activity of paclitaxel and paclitaxel analogs. In particular, N-malonyl-bis(N'-methyl-N'-thiobenzoylhydrazide) in combination with paclitaxel has been shown to increase the time to progression of patients suffering from stage IV metastatic melanoma relative to patients treated with paclitaxel alone. It would be advantageous to have still more active bis[thiohydrazide amide] anti-cancer compounds.

SUMMARY OF THE INVENTION

The present invention is directed to a compound comprising a bis[thiohydrazide amide] represented by Structural Formula (I):

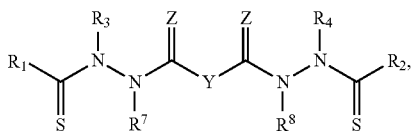

(I)

or a prodrug, isomer, ester, salt, hydrate, solvate, polymorph or deprotonated form thereof complexed, coordinated or chelated to a transition metal cation, wherein:

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aryl group;

Y is a covalent bond or a substituted or unsubstituted straight chained hydrocarbyl group, or Y, taken together with both >C=Z groups to which it is bonded, is a substituted or unsubstituted aryl group;

$R_7$ and $R_8$ are independently —H, an optionally substituted aliphatic group, or an optionally substituted aryl group; and Z is O or S.

One example of a compound of this type is represented by Structural Formula (II):

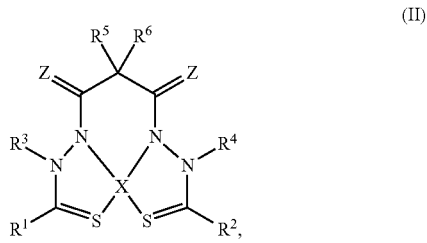

(II)

or a prodrug, isomer, ester, salt, hydrate, solvate, or polymorph thereof, wherein:

$R_5$ and $R_6$ are each independently —H, an aliphatic or substituted aliphatic group, or $R_5$ is —H and $R_6$ is optionally substituted aryl group, or $R_5$ and $R_6$, taken together, are an optionally substituted $C_2$-$C_6$ alkylene group;

X is a transition metal cation with a +2 charge; and the remainder of the variables are as described above for Structural Formula (I).

Another embodiment is a pharmaceutical composition comprising a compound of the invention and a pharmaceutically acceptable carrier or diluent. The pharmaceutical compositions can be used in therapy, for example, as an anti-proliferative agent (e.g., anti-cancer agent). In addition, the pharmaceutical compositions can be used in therapy to treat disorders responsive to Hsp70 induction, or the pharmaceutical compositions can be used in therapy to treat disorders responsive to natural killer cell induction, such as bacterial infections, fungal infections, viral infections, or parasitic infections. The pharmaceutical compositions can also be used in therapy to treat, reduce or inhibit angiogenesis in a subject in need thereof.

The present invention also provides for a method of treating a subject with cancer, treating a subject with an Hsp70-responsive disorder, treating a subject with a disorder responsive to natural killer cell induction or treating, reducing or inhibiting angiogenesis in a subject in need thereof. The method comprises administering to the subject an effective amount of a compound of the invention or a pharmaceutical composition of the invention. In one embodiment, the compound of the invention is administered with paclitaxel (Taxol®) or a paclitaxel analog.

The use of a compound of the invention for the manufacture of a medicament for treating a subject with cancer, for treating a subject with an Hsp70-responsive disorder, for treating a subject with a disorder responsive to natural killer cell induction or for treating, reducing or inhibiting angiogenesis in a subject in need thereof is also provided in the present invention.

The present invention is also directed to the use of a compound of the invention for treating a subject with cancer, for treating a subject with an Hsp70-responsive disorder, for treating a subject with a disorder responsive to natural killer cell induction or for treating, reducing or inhibiting angiogenesis in a subject in need thereof.

DETAILED DESCRIPTION OF THE INVENTION

Figure 1:
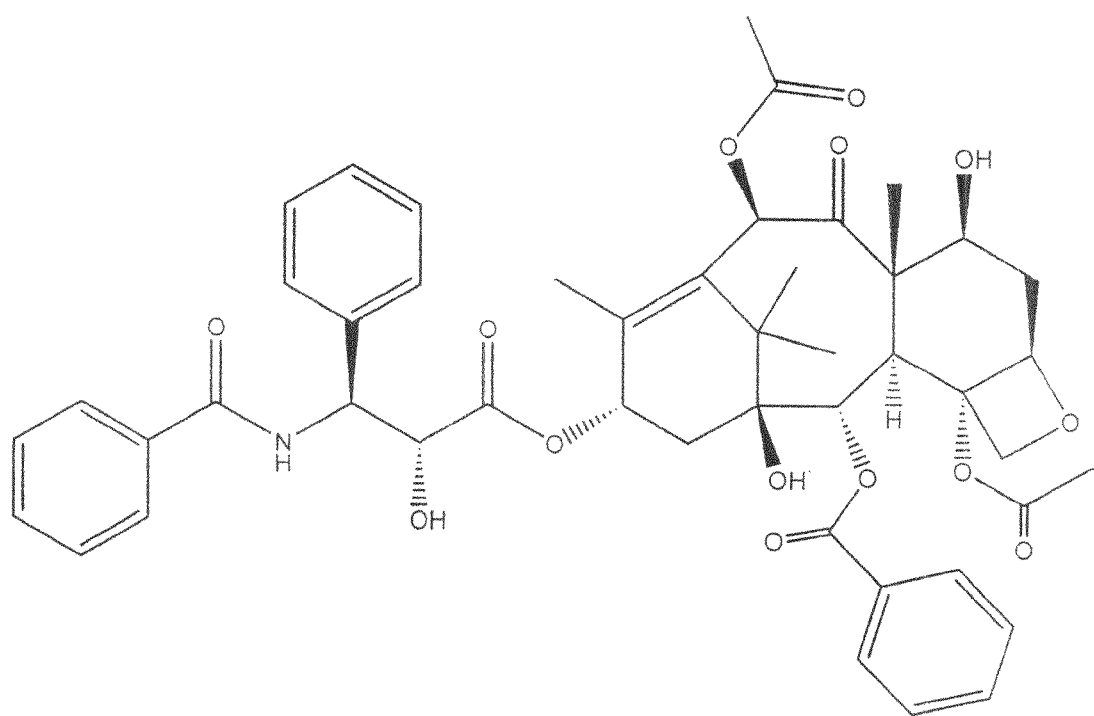
FIG. 1 is the structure of paclitaxel (Taxol®).

The present invention is directed to transition metal complexes (coordinates or chelates) of bis[thiohydrazide amide] represented by Structural Formula (I) or a prodrug, isomer, ester, salt, hydrate, solvate, polymorph or deprotonated form thereof. One example of a complex of this type is represented by Structural Formula (II) described above.

As used herein, "complexed" means that the bis[thiohydrazide amide] or a prodrug, isomer, ester, salt, hydrate, solvate, polymorph or deprotonated form thereof attaches to the transition metal ion through one or more coordinate covalent bonds or coordination bonds.

As used herein, "chelated" means that the bis[thiohydrazide amide] or a prodrug, isomer, ester, salt, hydrate, solvate, polymorph or deprotonated form thereof binds to the transition metal ion at two or more attachment points through coordinate covalent bonds or coordination bonds.

As used herein, "coordinate", "coordinated", "coordinate covalent bond" and "coordination bond" have the meanings that are commonly known to one of ordinary skill in the art.

As used herein, a "deprotonated form" of bis[thiohydrazide amide] refers to a molecule wherein one or more protons from the bis[thiohydrazide amide] or a prodrug, isomer, ester, salt, hydrate, solvate, or polymorph thereof were removed. For example, a deprotonated form of a bis[thiohydrazide amide] of Structural Formula (I), wherein $R_7$ and $R_8$ are both —H, is represented by the following Structural Formula:

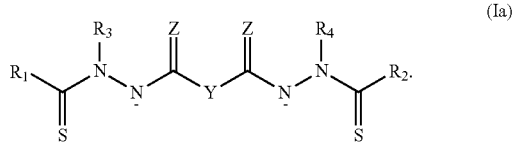

(Ia)

A "transition metal cation" refers to a positively charged ion of a metal in Groups 3-12 of the periodic table. Examples include $Ni^{2+}$, $Cu^+$, $Cu^{2+}$, $Co^{2+}$, $Co^{3+}$, $Fe^{2+}$, $Fe^{3+}$, $Zn^{2+}$, $Pt^{2+}$, $Pd^{2+}$, $V^{4+}$, $V^{5+}$, $Cr^{2+}$, $Cr^{3+}$, $Cr^{4+}$, $Mn^{2+}$, $Mn^{3+}$, $Mn^{4+}$ and $Mn^{5+}$. In a specific embodiment, the transition metal cations have a +2 charge. Examples include $Ni^{2+}$, $Cu^{2+}$, $Co^{2+}$, $Fe^{2+}$, $Zn^{2+}$, $Pt^{2+}$ and $Pd^{2+}$. In a specific embodiment, the transition metal cation is $Cu^+$, $Cu^{2+}$ or $Ni^{2+}$. In a more specific embodiment, the transition metal cation is $Cu^{2+}$. The molar ratio of bis[thiohydrazide amide] or a prodrug, isomer, ester, salt, hydrate, solvate, polymorph or a deprotonated form thereof to transition metal cation recited in this paragraph is, for example, equal to or greater than 0.5 and equal to or less than 2.0 (i.e. 0.5≤ratio≤2.0) or 1.

In another embodiment, the compound of the present invention is represented by Structural Formula (II):

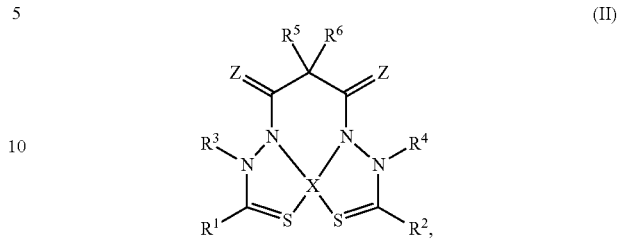

(II)

or a prodrug, isomer, ester, salt, hydrate, solvate, or polymorph thereof, wherein the variables are as described above. Examples of X include $Ni^{2+}$, $Cu^{2+}$, $Co^{2+}$, $Fe^{2+}$, $Zn^{2+}$, $Pt^{2+}$ and $Pd^{2+}$.

In another embodiment, the compound is represented by the following Structural Formula:

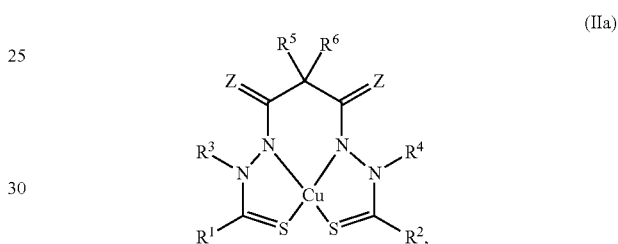

(IIa)

or a prodrug, isomer, ester, salt, hydrate, solvate, or polymorph thereof. Variables are as described above for Structural Formula (II).

In another embodiment, the compound is represented by the following Structural Formula:

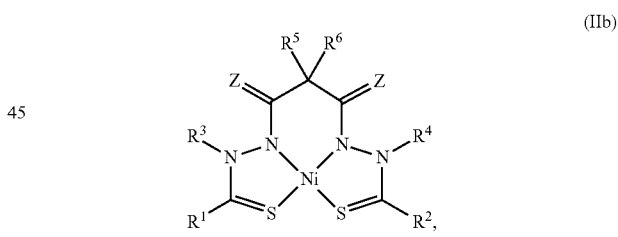

(IIb)

or a prodrug, isomer, ester, salt, hydrate, solvate, or polymorph thereof. Variables are as described above for Structural Formula (II).

In one embodiment, the bis[thiohydrazide amide] of Structural Formula (I) is represented by Structural Formula (III):

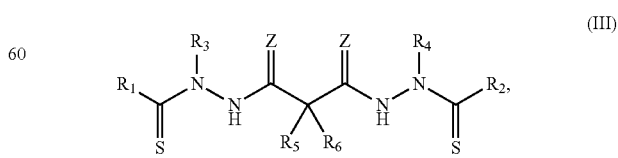

(III)

or a prodrug, isomer, ester, salt, hydrate, solvate, polymorph or deprotonated form thereof. The variables in Structural Formula (III) are as defined for Structural Formula (II). Preferably for Structural Formulas (I)-(III), including Structural Formulas (IIa) and (IIb), Z is O, $R_1$ and $R_2$ are the same and $R_3$ and $R_4$ are the same.

In another embodiment, the compound is represented by Structural Formula (IV):

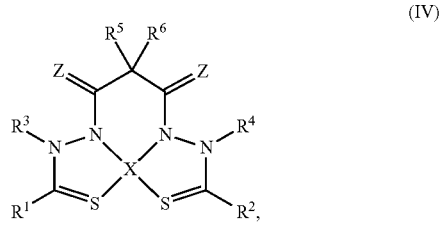

or a prodrug, isomer, ester, salt, hydrate, solvate, or polymorph thereof. Variables are as described above for Structural Formula (II), provided that when $R_1$ and $R_2$ are both phenyl, both Z atoms are O, and $R_3$ and $R_4$ are both methyl, then $R_5$ and $R_6$ are not both —H. In another embodiment of Structural Formula (IV), X is not $Cu^{2+}$ or $Ni^{2+}$.

In another embodiment, the bis[thiohydrazide amide] of Structural Formula (I) is represented by Structural Formula (V):

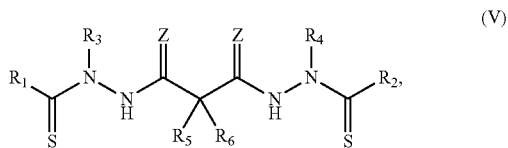

or a prodrug, isomer, ester, salt, hydrate, solvate, polymorph or deprotonated form thereof. The variables in Structural Formula (V) are as defined for Structural Formula (II), provided that when $R_1$ and $R_2$ are both phenyl, both Z atoms are O, and $R_3$ and $R_4$ are both methyl, then $R_5$ and $R_6$ are not both —H.

Alternatively for Structural Formulas (II), (IIa), (IIb), (III), (IV) and (IV) $R_1$ and $R_2$ are each an optionally substituted aryl group; $R_3$ and $R_4$ are each an optionally substituted aliphatic group; $R_5$ and $R_6$ are each independently —H, an aliphatic or substituted aliphatic group, or $R_5$ is —H and $R_6$ is optionally substituted aryl group, or $R_5$ and $R_6$, taken together, are an optionally substituted $C_2$-$C_6$ alkylene group; and each Z is O. Suitable substituents for an aryl and aliphatic group are provided below.

In another alternative for Structural Formulas (II), (IIa), (IIb (III), (IV) and (IV), $R_1$ and $R_2$ are each an optionally substituted phenyl group; $R_3$ and $R_4$ are each an optionally substituted alkyl group; $R_5$ is —H; $R_6$ is —H, an alkyl or substituted alkyl group; and each Z is O. Suitable substituents for an aryl and aliphatic group are provided below.

In another alternative for Structural Formulas (II), (IIa), (IIb), (III), (IV) and (IV), the phenyl groups represented by $R_1$ and $R_2$ are optionally substituted with one or more (e.g. two, three, four, five, etc.) groups independently selected from the group consisting of $C_1$-$C_4$ alkyl, $C_1$-$C_4$ alkoxy, $C_1$-$C_4$ haloalkyl, $C_1$-$C_4$ haloalkoxy, phenyl, benzyl, pyridyl, —OH, —$NH_2$, —F, —Cl, —Br, —I, —$NO_2$ and —CN, wherein the phenyl and benzyl substituents are optionally substituted with one or more (e.g. two, three, four, five etc.) substituents independently selected from the group consisting of halo, $C_1$-$C_4$ alkyl, $C_1$-$C_4$ alkoxy, $C_1$-$C_4$ haloalkyl, and $C_1$-$C_4$ haloalkoxy; the alkyl groups represented by $R_3$ and $R_4$ are optionally substituted with one or more (e.g. two, three, four, five etc.) substituents independently selected from the group consisting of —OH, halogen, phenyl, benzyl, pyridyl, and $C_1$-$C_8$ alkoxy, wherein the phenyl and benzyl substituents are optionally substituted with one or more (e.g. two, three, four, five etc.) substituents independently selected from the group consisting of halo, $C_1$-$C_4$ alkyl, $C_1$-$C_4$ alkoxy, $C_1$-$C_4$ haloalkyl, and $C_1$-$C_4$ haloalkoxy; $R^5$ is H; $R_6$ is —H or methyl; and each Z is O.

In another alternative for Structural Formulas (II), (IIa), (IIb), (III), (IV) and (IV), $R_1$ and $R_2$ are each an optionally substituted aliphatic group; $R_3$ and $R_4$ are each an optionally substituted aliphatic group; $R_5$ and $R_6$ are each independently —H, an aliphatic or substitute aliphatic group, or $R_5$ is —H and $R_6$ is optionally substituted aryl group, or $R_5$ and $R_6$, taken together, are an optionally substituted $C_2$-$C_6$ alkylene group; and each Z is O. Suitable substituents for an aliphatic group are provided below.

In another alternative for Structural Formulas (II), (IIa), (IIb), (III), (IV) and (IV), $R_1$ and $R_2$ are both a $C_3$-$C_8$ cycloalkyl group optionally substituted with at least one alkyl group; $R_3$ and $R_4$ are each an optionally substituted alkyl group; $R_5$ is —H; $R_6$ is —H, an alkyl or substituted alkyl group; and each Z is O.

In another alternative for Structural Formulas (II), (IIa), (IIb), (III), (IV) and (IV), $R_1$ and $R_2$ are both a $C_3$-$C_8$ cycloalkyl group optionally substituted with at least one alkyl group; the alkyl groups represented by $R_3$ and $R_4$ are optionally substituted with one or more (e.g. two, three, four, five etc.) substituents independently selected from the group consisting of —OH, halogen, phenyl, benzyl, pyridyl, and $C_1$-$C_8$ alkoxy, wherein the phenyl and benzyl substituents are optionally substituted with one or more (e.g. two, three, four, five etc.) substituents independently selected from the group consisting of halo, $C_1$-$C_4$ alkyl, $C_1$-$C_4$ alkoxy, $C_1$-$C_4$ haloalkyl, and $C_1$-$C_4$ haloalkoxy; $R^5$ is H; $R_6$ is —H or methyl; and each Z is O. $R_1$ and $R_2$ are preferably cyclopropyl or 1-methylcyclopropyl.

In the embodiments described above, preferably $R_1$ and $R_2$ are the same and $R_3$ and $R_4$ are the same.

Specific examples of values for variables in Structural Formulas (II), (IIa), (IIb) or (III), wherein each Z is O and the remainder of the variables are defined as follows:

$R_1$ and $R_2$ are both phenyl, $R_3$ and $R_4$ are both methyl, and $R_5$ and $R_6$ are both —H;

$R_1$ and $R_2$ are both phenyl, $R_3$ and $R_4$ are both ethyl, and $R_5$ and $R_6$ are both —H;

$R_1$ and $R_2$ are both 4-cyanophenyl, $R_3$ and $R_4$ are both methyl, $R_5$ is methyl, and $R_6$ is —H;

$R_1$ and $R_2$ are both 4-methoxyphenyl, $R_3$ and $R_4$ are both methyl, and $R_5$ and $R_6$ are both H;

$R_1$ and $R_2$ are both phenyl, $R_3$ and $R_4$ are both methyl, $R_5$ is methyl, and $R_6$ is —H;

$R_1$ and $R_2$ are both phenyl, $R_3$ and $R_4$ are both ethyl, $R_5$ is methyl, and $R_6$ is —H;

$R_1$ and $R_2$ are both 4-cyanophenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, and $R_5$ and $R_6$ are both —H;

$R_1$ and $R_2$ are both 2,5-dimethoxyphenyl, $R_3$ and $R_4$ are both methyl, $R_5$ is methyl, and $R_6$ is —H;

$R_1$ and $R_2$ are both 3-cyanophenyl, $R_3$ and $R_4$ are both methyl, and $R_5$ and $R_6$ are both —H;

$R_1$ and $R_2$ are both 3-fluorophenyl, $R_3$ and $R_4$ are both methyl, and $R_5$ and $R_6$ are both —H;

$R_1$ and $R_2$ are both 4-chlorophenyl, $R_3$ and $R_4$ are both methyl, $R_5$ is methyl, and $R_6$ is —H;

$R_1$ and $R_2$ are both 2-methoxyphenyl, $R_3$ and $R_4$ are both methyl, and $R_5$ and $R_6$ are both —H;

$R_1$ and $R_2$ are both 3-methoxyphenyl, $R_3$ and $R_4$ are both methyl, and $R_5$ and $R_6$ are both —H;

$R_1$ and $R_2$ are both 2,3-dimethoxyphenyl, $R_3$ and $R_4$ are both methyl, and $R_5$ and $R_6$ are both —H;

$R_1$ and $R_2$ are both 2,3-dimethoxyphenyl, $R_3$ and $R_4$ are both methyl, $R_5$ is methyl, and $R_6$ is —H;

$R_1$ and $R_2$ are both 2,5-difluorophenyl, $R_3$ and $R_4$ are both methyl, and $R_5$ and $R_6$ are both —H;

$R_1$ and $R_2$ are both 2,5-difluorophenyl, $R_3$ and $R_4$ are both methyl, $R_5$ is methyl, and $R_6$ is —H;

$R_1$ and $R_2$ are both 2,5-dichlorophenyl, $R_3$ and $R_4$ are both methyl, and $R_5$ and $R_6$ are both —H;

$R_1$ and $R_2$ are both 2,5-dimethylphenyl, $R_3$ and $R_4$ are both methyl, and $R_5$ and $R_6$ are both —H;

$R_1$ and $R_2$ are both cyclopropyl, $R_3$ and $R_4$ are both methyl, and $R_5$ and $R_6$ are both —H;

$R_1$ and $R_2$ are both cyclopropyl, $R_3$ and $R_4$ are both ethyl, and $R_5$ and $R_6$ are both —H;

$R_1$ and $R_2$ are both cyclopropyl, $R_3$ and $R_4$ are both methyl, $R_5$ is methyl, and $R_6$ is —H;

$R_1$ and $R_2$ are both 1-methylcyclopropyl, $R_3$ and $R_4$ are both methyl, and $R_5$ and $R_6$ are both —H;

$R_1$ and $R_2$ are both 1-methylcyclopropyl, $R_3$ and $R_4$ are both methyl. $R_5$ is methyl and $R_6$ is —H;

$R_1$ and $R_2$ are both 1-methylcyclopropyl, $R_3$ and $R_4$ are both methyl, $R_5$ is ethyl, and $R_6$ is —H;

$R_1$ and $R_2$ are both 1-methylcyclopropyl, $R_3$ and $R_4$ are both methyl, $R_5$ is n-propyl, and $R_6$ is —H;

$R_1$ and $R_2$ are both 1-methylcyclopropyl, $R_3$ and $R_4$ are both methyl, and $R_5$ and $R_6$ are both methyl;

$R_1$ and $R_2$ are both 1-methylcyclopropyl, $R_3$ and $R_4$ are both ethyl, and $R_5$ and $R_6$ are both —H;

$R_1$ and $R_2$ are both 1-methylcyclopropyl, $R_3$ is methyl, $R_4$ is ethyl, and $R_5$ and $R_6$ are both —H;

$R_1$ and $R_2$ are both 2-methylcyclopropyl, $R_3$ and $R_4$ are both methyl, and $R_5$ and $R_6$ are both —H;

$R_1$ and $R_2$ are both 2-phenylcyclopropyl, $R_3$ and $R_4$ are both methyl, and $R_5$ and $R_6$ are both —H;

$R_1$ and $R_2$ are both 1-phenylcyclopropyl, $R_3$ and $R_4$ are both methyl, and $R_5$ and $R_6$ are both —H;

$R_1$ and $R_2$ are both cyclobutyl, $R_3$ and $R_4$ are both methyl, and $R_5$ and $R_6$ are both —H;

$R_1$ and $R_2$ are both cyclopentyl, $R_3$ and $R_4$ are both methyl, and $R_5$ and $R_6$ are both —H;

$R_1$ and $R_2$ are both cyclohexyl. $R_3$ and $R_4$ are both methyl, and $R_5$ and $R_6$ are both —H;

$R_1$ and $R_2$ are both cyclohexyl, $R_3$ and $R_4$ are both phenyl, and $R_5$ and $R_6$ are both —H;

$R_1$ and $R_2$ are both methyl, $R_3$ and $R_4$ are both methyl, and $R_5$ and $R_6$ are both —H;

$R_1$ and $R_2$ are both methyl, $R_3$ and $R_4$ are both t-butyl, and $R_5$ and $R_6$ are both —H;

$R_1$ and $R_2$ are both methyl, $R_3$ and $R_4$ are both phenyl, and $R_5$ and $R_6$ are both —H;

$R_1$ and $R_2$ are both t-butyl, $R_3$ and $R_4$ are both methyl, and $R_5$ and $R_6$ are both —H;

$R_1$ and $R_2$ are both ethyl, $R_3$ and $R_4$ are both methyl, and $R_5$ and $R_6$ are both —H; or $R_1$ and $R_2$ are both n-propyl, $R_3$ and $R_4$ are both methyl, and $R_5$ and $R_6$ are both —H.

Exemplary bis[thiohydrazide amides] are represented by the following structural formulas:

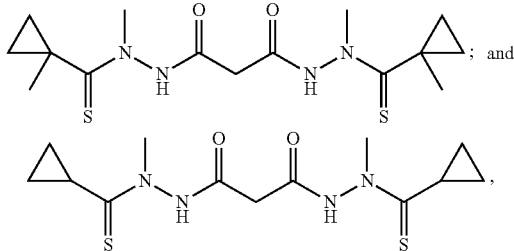

or a prodrug, isomer, ester, salt, hydrate, solvate, or polymorph thereof.

Exemplary compounds of the invention are represented by the following Structural Formulas:

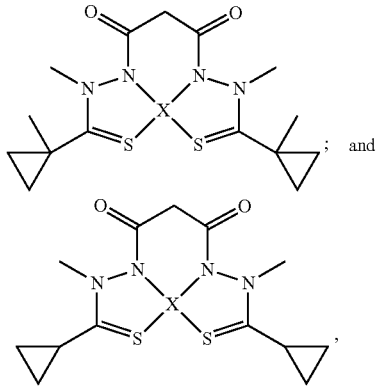

or a prodrug, isomer, ester, salt, hydrate, solvate, or polymorph thereof.

The compounds of the invention are advantageously in substantially pure form, e.g., greater than 50%, 60%, 70%, 80%, 90%, 95%, 97%, 99%, 99.5% or 99.9% pure by weight. "Percent purity by weight" means the weight of the compound divided by the weight of the compound plus impurities times 100%.

The compounds of the present invention can be prepared by reacting a bis[thiohydrazide amide] or a prodrug, isomer, ester, salt, hydrate, solvate, or polymorph thereof, described herein with a transition metal salt. The transition metal salt can be any inorganic or organic salts of the transition metal cation. For example, chloride salt, nitrate salt, sulfate salt, acetate salt and the like can be reacted with a bis[thiohydrazide amide] or a prodrug, isomer, ester, salt, hydrate, solvate, or polymorph thereof described herein to afford the compounds of the present invention. In one embodiment, the transition metal salt is a copper(II) salt, such as $CuCl_2$. In another embodiment, the transition metal salt is a nickel(II) salt, such as $NiCl_2.6H_2O$.

The ratio of the bis[thiohydrazide amide] or a prodrug, isomer, ester, salt, hydrate, solvate, or polymorph thereof and the transition metal cation source used is typically in the range of 0.5 to 2.0 or 0.8 to 1.2. In one embodiment, the ratio is about 1.

Solvents, such as methylene chloride, acetonitrile, acetone, alcohols (such as methanol, ethanol), tetrahydrofuran and water can be used in the reaction of the bis[thiohydrazide amide] or a prodrug, isomer, ester, salt, hydrate, solvate, or polymorph thereof with the transition metal salts. In one embodiment, the solvent is ethanol.

The bis[thiohydrazide amides] used to prepare the disclosed compounds can be prepared according to methods described in U.S. Pat. Nos. 6,800,660, 6,762,204, and 6,825, 235 and U.S. Publication No. 2008/0146842. The entire teachings of these patents and publications are incorporated herein by reference.

Certain compounds of the invention may be obtained as different isomers (e.g., stereoisomers, coordination isomers, linkage isomers, hydrate isomers, and the like). The invention includes isomeric forms of the disclosed compounds and both pure isomers and mixtures thereof, including racemic mixtures. Isomers can the separated and isolated using any suitable method, such as chromatography.

The compounds of the invention may contain one or more chiral centers and/or double bonds and, therefore, exist as stereoisomers, such as double-bond isomers geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, the term "polymorph" means solid crystalline forms or a compound of the present invention described herein. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound of the present invention described herein, that further includes a stoichiometric or non-stoichiometric amount of solvent bound by non-covalent intermolecular forces.

As used herein, the term "hydrate" means a compound of the present invention described herein, that further includes a stoichiometric or non-stoichiometric amount of water bound by non-covalent intermolecular forces.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms.

The compounds of the invention or bis[thiohydrazide amide] described herein may be present in the form of salts. In one embodiment, the salts of the compounds of the invention refer to non-toxic "pharmaceutically acceptable salts." In another embodiment, the salts also include non-pharmaceutically acceptable salts, such as trifluoroacetate.

Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalaeturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

An "alkyl group" is saturated straight or branched chain linear or cyclic hydrocarbon group. Typically, a straight chained or branched alkyl group has from 1 to about 20 carbon atoms, preferably from 1 to about 10, and a cyclic alkyl group has from 3 to about 10 carbon atoms, preferably from 3 to about 8. An alkyl group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A $C_1$-$C_8$ straight chained or branched alkyl group or a $C_3$-$C_8$ cyclic alkyl group is also referred to as a "lower alkyl" group. Suitable substituents for an alkyl group are those which do not substantially interfere with the anti-cancer activity of the disclosed compounds. Suitable substituents are as described below for aliphatic groups. Preferred substituents on alkyl groups include, —OH, —$NH_2$, —$NO_2$, —CN, —COOH, halogen, aryl, $C_1$-$C_8$ alkoxy, $C_1$-$C_8$ haloalkoxy and —CO($C_1$-$C_8$ alkyl). More preferred substituents on alkyl groups include —OH, halogen, phenyl, benzyl, pyridyl, and $C_1$-$C_8$ alkoxy. More preferred substituents on alkyl groups include —OH, halogen, and $C_1$-$C_4$ alkoxy.

A "straight chained hydrocarbyl group" is an alkylene group, i.e., —$(CH_2)_y$—, with one or more (preferably one) internal methylene groups optionally replaced with a linkage group. y is a positive integer (e.g., between 1 and 10), preferably between 1 and 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine (—N($R^a$)—), wherein $R^a$ is defined below. A preferred linkage group is —C($R_5R_6$)—, wherein $R_5$ and $R_6$ are defined above. Suitable substituents for an alkylene group and a hydrocarbyl group are those which do not substantially interfere with the anti-cancer activity of the disclosed compounds. $R_5$ and $R_6$ are preferred substituents for an alkylene or hydrocarbyl group represented by Y.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A $C_1$-$C_8$ straight chained or branched alkyl group or a $C_3$-$C_8$ cyclic alkyl group is also referred to as a "lower alkyl" group.

The term "aromatic group" may be used interchangeably with "aryl," "aryl ring," "aromatic ring," "aryl group" and "aromatic group." Aromatic groups include carbocyclic aromatic groups such as phenyl, naphthyl, and anthracyl, and heteroaryl groups such as imidazolyl, thienyl, furanyl, pyridyl, pyrimidyl, pyranyl, pyrazolyl, pyrroyl, pyrazinyl, thiazole, oxazolyl, and tetrazole. The term "heteroaryl group" may be used interchangeably with "heteroaryl," "heteroaryl ring," "heteroaromatic ring" and "heteroaromatic group." Heteroaryl groups are aromatic groups that comprise one or more heteroatom, such as sulfur, oxygen and nitrogen, in the ring structure. Preferably, heteroaryl groups comprise from one to four heteroatoms.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

Substituents for an arylene group are as described below aryl group.

Non-aromatic heterocyclic rings are non-aromatic rings which include one or more heteroatoms such as nitrogen, oxygen or sulfur in the ring. The ring can be five, six, seven or eight-membered. Preferably, heterocyclic groups comprise from one to about four heteroatoms. Examples include tetrahydrofuranyl, tetrahydrothiophenyl, morpholino, thiomorpholino, pyrrolidinyl, piperazinyl, piperidinyl, and thiazolidinyl.

The terms "lower alkoxy", "lower acyl", "(lower alkoxy)methyl" and "(lower alkyl)thiomethyl" mean to —O-(lower alkyl), —C(O)-(lower alkyl), —$CH_2$—O-(lower alkyl) and —$CH_2$—S-(lower alkyl), respectively. The terms "substituted lower alkoxy" and "substituted lower acyl" mean —O-(substituted lower alkyl) and —C(O)— (substituted lower alkyl), respectively.

Suitable substituents for an aryl group, non-aromatic heterocyclic group, an aliphatic group, alkylene group or a hydrocarbyl group represented by the variables in the structural formulas described herein are those which do not significantly reduce the biological activity of the compound. Examples include —$R^a$, —OH, —Br, —Cl, —I, —F, —$OR^a$, —O—$COR^a$, —$COR^a$, —CN, —NCS, —$NO_2$, —COOH, —$SO_3H$, —$NH_2$, —$NHR^a$, —N($R^aR^b$), —$COOR^a$, —CHO, —$CONH_2$, —$CONHR^a$, —CON($R^aR^b$), —$NHCOR^a$, —$NR^cCOR^a$, —$NHCONH_2$, —$NHCONR^aH$, —NHCON($R^aR^b$), —$NR^cCONH_2$, —$NR^cCONR^aH$, —$NR^cCON$($R^aR^b$), —C(=NH)—$NH_2$, —C(=NH)—$NHR^a$, —C(=NH)—N($R^aR^b$), —C(=$NR^c$)—$NH_2$, —C(=$NR^c$)—$NHR^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, —NH—C(=$NR^c$)—$NHR^a$, —NH—C(=$NR^c$)—N($R^aR^b$), —$NR^d$—C(=NH)—$NH_2$, —$NR^d$—C(=NH)—$NHR^a$, —$NR^d$—C(=NH)—N($R^aR^b$), —$NR^d$—C(=$NR^c$)—$NH_2$, —$NR^d$—C(=$NR^c$)—$NHR^a$, —$NR^d$—C(=$NR^c$)—N($R^aR^b$), —$NHNH_2$, —$NHNHR^a$, —$NHNR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$, wherein $R^a$—$R^d$ are each independently an alkyl group, aromatic group, non-aromatic heterocyclic group; or, —N($R^aR^b$), taken together, form an optionally substituted non-aromatic heterocyclic group, wherein the alkyl, aryl and non-aromatic heterocyclic group represented by $R^a$—$R^d$ and the non-aromatic heterocyclic group represented by —N($R^aR^b$) are each optionally and independently substituted with one or more groups represented by $R^\#$, wherein $R^\#$ is $R^+$, —$OR^+$, —O(haloalkyl), —$SR^+$, —$NO_2$—CN, —NCS, —N($R^+$)$_2$, —$NHCO_2R^+$, —NHC(O)$R^+$, —NHNHC(O)$R^+$, —NHC(O)N($R^+$)$_2$, —NHNHC(O)N($R^+$)$_2$, —$NHNHCO_2R^+$, —C(O)C(O)$R^+$, —C(O)$CH_2$C(O)$R^+$, —$CO_2R^+$, —C(O)$R^+$, C(O)N($R^+$)$_2$, —OC(O)$R^+$, —OC(O)N($R^+$)$_2$, —S(O)$_2R^+$, —$SO_2N(R^+)_2$, —S(O)$R^+$, —$NHSO_2N(R^+)_2$, —$NHSO_2R^+$, —C(=S)N($R^+$)$_2$, or —C(=NH)—N($R^+$)$_2$; wherein $R^+$ is —H, a C1-C4 alkyl group, a monocyclic heteroaryl group, a non-aromatic heterocyclic group or a phenyl group optionally substituted with alkyl, haloalkyl, alkoxy, haloalkoxy, halo, —CN, —$NO_2$, amine, alkylamine or dialkylamine; or —N($R^+$)$_2$ is a non-aromatic heterocyclic group, provided that non-aromatic heterocyclic groups represented by $R^+$ and —N($R^+$)$_2$ that comprise a secondary ring amine are optionally acylated or alkylated. Commonly used substituents for an aryl group represented by the variables in the structural formulas described herein include $C_1$-$C_4$ alkyl, $C_1$-$C_4$ alkoxy, haloalkyl, $C_1$-$C_4$ haloalkoxy, phenyl (optionally substituted with halo $C_1$-$C_4$ alkyl, $C_1$-$C_4$ alkoxy, $C_1$-$C_4$ haloalkyl, $C_1$-$C_4$ haloalkoxy), benzyl (optionally substituted with halo $C_1$-$C_4$ alkyl, $C_1$-$C_4$ alkoxy, $C_1$-$C_4$ haloalkyl, $C_1$-$C_4$ haloalkoxy), pyridyl, —OH, —$NH_2$, —F, —Cl, —Br, —I, —$NO_2$ and —CN. Commonly used substituents for an non-aromatic heterocyclic group, an aliphatic group, alkylene group or a hydrocarbyl group represented by the variables in the structural formulas described herein include —OH, halogen, phenyl (optionally substituted with halo $C_1$-$C_4$ alkyl, $C_1$-$C_4$ alkoxy, $C_1$-$C_4$ haloalkyl, $C_1$-$C_4$ haloalkoxy), benzyl (optionally substituted with halo $C_1$-$C_4$ alkyl, $C_1$-$C_4$ alkoxy, $C_1$-$C_4$ haloalkyl, $C_1$-$C_4$ haloalkoxy), pyridyl, and $C_1$-$C_8$ alkoxy.

Preferred substituents for a cycloalkyl group, including cycloalkyl groups represented by $R_1$ and $R_2$, are alkyl groups, such as a methyl or ethyl group.

The compounds of the invention are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds of the invention can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

One embodiment of the present invention is a method of treating a subject with a proliferative disorder comprising administering to the subject an effective amount of a compound or a pharmaceutical composition thereof. Cancer, including multidrug resistant cancer, is one type of proliferative disorder that can be treated with the compounds of the invention. Non-malignant proliferative disorders are also included in the invention.

"Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, ameliorating or improving a clinical symptom or indicator associated with a cancer (such as tissue or serum components) and/or reducing the likelihood of the cancer recurring once it has been removed or gone into remission.

It has been surprisingly found that the transition metal chelates, coordinates or complexes disclosed herein show sufficient anti-cancer activity to make them suitable for monotherapies, as well as in combination or in co-therapies with other anti-proliferative or anticancer therapies. In particular, it has been found that transition metal chelates, coordinates or complexes of compounds of the aforementioned U.S. Pat. Nos. 6,800,660; 6,762,204; 7,037,940; 7,001,923; and 6,924,312 can have sufficient anti-cancer activity to make them suitable for monotherapies, as well as in combination or in co-therapies with other anti-proliferative or anticancer therapies such as paclitaxel.

Other anti-proliferative or anticancer therapies may be combined with the compounds or the pharmaceutical compositions of this invention to treat proliferative diseases and cancer. Examples include combination therapy with other anti-cancer drugs, surgery, radiotherapy (including, but not limited to, gamma-radiation, neutron beam radiotherapy, electron beam radiotherapy, proton therapy, brachytherapy, and systemic radioactive isotopes), thermal therapy (see, for example, U.S. Publication No. 2008/0119440, the entire teachings of which are incorporated herein by reference) and endocrine therapy. Other anticancer agents that may be used in combination with the compounds or the pharmaceutical compositions of the present invention include biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs. Specific examples of anticancer agents are described in detail below. Preferably, the co-administered anti-cancer drug is an agent that stabilizes microtubules, such as paclitaxel or an analog of paclitaxel.

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma. Ewing's tumor, leiomyosarcoma, rhabdomyosarcoma, colon carcinoma, pancreatic cancer; breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinorna, medullary carcinoma, bronchogenic carcinoma, renal cell carcinoma, hepatoma, bile duct carcinoma, choriocarcinoma, seminoma, embryonal carcinoma. Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Erie Cancer Medicine* 5th Ed., Bast et al. Eds., B. C. Decker Inc. (2000). The entire teachings of the preceding references are incorporated herein by reference.

Additional cancers that can be treated or prevented by the methods of the present invention include, but are not limited to oral cavity and pharynx cancers, including tongue, mouth, pharynx, and other oral cavity cancers; digestive system cancers, including esophagus, small intestine, rectum, anus, anal canal, anorectum, liver and intrahepatic bile duct, gallbladder and other biliary, pancreas and other digestive organs; respiratory system cancers, including larynx and bronchus; bone and joint cancers; soft tissue (including heart) cancers; genital system cancers, including uterine cervix, uterine corpus, ovary, vulva, vagina and other genital, female, testis, penis and other genital, male; urinary system cancers, including kidney and renal pelvis, and ureter and other urinary organs; eye and orbit cancers; leukemia, including acute myeloid leukemia and chronic myeloid leukemia.

In one embodiment, the disclosed method is believed to be particularly effective in treating a subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line), monocytic leukemia (e.g., as exemplified by the THP-1 (acute) cell line); and lymphoma (e.g., as exemplified by the U937 cell line).

In another embodiment, the disclosed method is believed to be particularly effective in treating a subject with melanoma.

In another embodiment, the disclosed method is believed to be particularly effective in treating a subject with renal cell carcinoma.

The disclosed method is particularly effective at treating subjects whose cancer has become "drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiters syndrome, pityriasis rubra pilaris, and hyperproliferative variants of disorders of keratinization (e.g., actinic keratosis, senile keratosis), sclerodenua, and the like.

Drugs that can be used in combination with the compounds of the invention to treat a patient with a proliferative disorder such as cancer, or to reduce the likelihood of the reoccurrence of a proliferative disorder such as cancer, include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate, apoptosis gene modulators; apoptosis regulators; apurinic acid; ara-CDP-DL-PTBA; arginine deaminase; asulacrine; atamcstane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogs; clotrimazole; collismycin A; collismycin B; combretastatin A4; combretastatin analog; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analog; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analog; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogs; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone, N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin, osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; piranthicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed, ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in combination with the compounds of the invention to treat a proliferative disorder such as cancer, or to reduce the likelihood of the reoccurrence of a proliferative disorder such as cancer, include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoproten IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Gcnentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALAN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNE-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4-IgG antibody (Elan); and CAT-152 is a human anti-TGF-β2 antibody (Cambridge Ab Tech).

Chemotherapeutic agents that can be used in combination with the compounds of the invention to treat a patient with a proliferative disorder such as cancer, or to reduce the likelihood of the reoccurrence of a proliferative disorder such as cancer, include but are not limited to alkylating agents, antimetabolites, natural products, or hormones.

Examples of alkylating agents useful for the treatment or prevention (reduction in the likelihood of developing or the likelihood of reoccurrence) of a proliferative disorder such as cancer in the methods and compositions of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates busulfan), nitrosoureas (e.g., carmustine, lomusitne, semustine, streptozocin, etc.), or triazenes (decarbazine, etc.). Examples of antimetabolites useful for the treatment or prevention (reduction in the likelihood of developing or the likelihood of reoccurrence) of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention (reduction in the likelihood of developing or the likelihood of reoccurrence) of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., asparaginase), or biological response modifiers (e.g., interferon alpha). Examples of hormones and antagonists useful for the treatment or prevention (reduction in the likelihood of developing or the likelihood of reoccurrence) of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and with the compositions of the invention for the treatment or prevention (reduction in the likelihood of developing or the likelihood of reoccurrence) of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In one embodiment, the compounds of the invention can be used in combination with an immunotherapeutic agent for the treatment of a proliferative disorder such as cancer, or to reduce the likelihood of the reoccurrence of a proliferative disorder such as cancer. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include: cancer vaccines, tumor cell vaccines (autologous or allogeneic), dendritic cell vaccines, antigen vaccines, anti-idiotype vaccines, DNA vaccines, Lymphokine-Activated Killer (LAK) Cell Therapy, or Tumor-Infiltrating Lymphocyte (TIL) Vaccine with Interleukin-2 (IL 2). Active immunotherapies are currently being used to treat or being tested to treat various types of cancers, including melanoma, kidney (renal) cancer, bladder cancer, prostate cancer, ovarian cancer, breast cancer, colorectal cancer, lung cancer, leukemia, prostate cancer, non-Hodgkin's lymphoma, pancreatic cancer, lymphoma, multiple myeloma, head and neck cancer, liver cancer, malignant brain tumors, and advanced melanoma.

Examples of passive immunotherapies include: monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to a chemotherapy drug (chemolabeled), a radioactive particle (radiolabeled), or a toxin (immunotoxin). A number of naked monoclonal antibody drugs have been approved for treating cancer, including:

Rituximab (Rituxat™), a antibody against the CD20 antigen used to treat B cell non-Hodgkin lymphoma; Trastuzumab (Herceptin), an antibody against the HER2 protein used to treat advanced breast cancer; Alemtuzumab (Campath), an antibody against the CD52 antigen used to treat B cell chronic lymphocytic leukemia (B-CLL); Cetuximab (Erbitux), an antibody against the EGFR protein used in combination with irinotecan to treat advanced colorectal cancer and to treat head and neck cancers; and Bevacizumab (Avastin) which is an antiangiogenesis therapy that works against the VEGF protein and is used in combination with chemotherapy to treat metastatic colorectal cancer. A number of conjugated monoclonal antibodies have been approved for treating cancer, including: Radiolabeled antibody Ibritumomab tiuxetan (Zevalin) which delivers radioactivity directly to cancerous B lymphocytes and is used to treat B cell non-Hodgkin lymphoma; radiolabeled antibody Tositumomab (Bexxar) which is used to treat certain types of non-Hodgkin lymphoma; and immunotoxin Gemtuzumab ozogamicin (Mylotarg) which contains calicheamicin and is used to treat acute myelogenous leukemia (AML). BL22 is a conjugated monoclonal antibody currently in testing for treating hairy cell leukemia and there are several immunotoxin clinical trials in progress for treating leukemias, lymphomas, and brain tumors. There are also approved radiolabeled antibodies used to detect cancer, including OncoScint for detecting colorectal and ovarian cancers and ProstaScint for detecting prostate cancers. Targeted therapies containing toxins are toxins linked to growth factors and do not contain antibodies. An example of an approved targeted therapy containing toxins is denileukin diftitox (Ontak) which is used to treat a type of skin lymphoma (cutaneous T cell lymphoma).

Examples of adjuvant immunotherapies include: cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP). Clinical studies have shown that combining IL-2 with other cytokines, such as IFN-alpha, can lead to a synergistic response.

Several types of immunotherapies are being used to treat melanoma patients. IFN-alpha and IL-2 are approved for treatment of people with metastatic melanoma. BCG is being tested in combination with melanoma vaccines and other immunotherapies. Tumor-infiltrating lymphocytes have been shown to shrink melanoma tumors in a phase 1 clinical trial. Human monoclonal antibodies to ganglioside antigens have been shown to regress cutaneous recurrent melanoma tumors. Some autologous and allogeneic tumor cell vaccines, antigen vaccines (including polyvalent antigen vaccines), viral vaccines, and dendritic cell vaccines have also been shown to shrink tumors. Clinical trials continue for these and other melanoma immunotherapies. Melanoma patients with a high IgM response often survive better than those who elicit no or low IgM antibodies (Morton et al., 1992). Combined IL-12/TNF-alpha immunotherapy has been shown to significantly retard tumor growth in three tumor models in mice (B16F10 melanoma, Lewis lung (LL/2) carcinoma and L1 sarcoma) as compared with controls and mice treated with either cytokine alone. IFN-alpha is approved for the treatment of malignant melanoma, chronic myelogenous leukemia (CML), hairy cell leukemia, and Kaposi's sarcoma.

Several types of immunotherapies are being used to treat patients that have renal cancer. IFN-alpha and IL-2 are approved for treatment of people with metastatic renal (kidney) cancer. A combination therapy using IL-2, interferon, and chemotherapy is being tested for treatment of renal cancer. Treatment with a tumor cell vaccine plus the adjuvant BCG has been shown to shrink tumors in some advanced renal cancer patients. DNA vaccines and tumor-infiltrating lymphocytes are also being tested as treatments for renal cancer. Chimeric bispecific G250/anti-CD3 monoclonal antibodies have been shown to mediate cell lysis of renal cell carcinoma cell lines by cloned human CD8+ T cells or by IL-2 stimulated peripheral blood lymphocytes.

As used herein, a "microtubulin stabilizer" means an anti-cancer agent which acts by arresting cells in the G2-M phases due to stabilization of microtubules. Agents which are microtubulin stabilizers can be used in combination with the compounds of the invention to treat patients having a proliferative disorder such as cancer, or to reduce the likelihood of the reoccurrence of a proliferative disorder such as cancer. Examples of microtubulin stabilizers include paclitaxel and paclitaxel analogs. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anti-cancer agent which acts by inhibiting tubulin polymerization or microtubule assembly. Agents which are microtubulin inhibitors can be used in combination with the compounds of the invention to treat patients having a proliferative disorder such as cancer, or to reduce the likelihood the reoccurrence of a proliferative disorder such as cancer. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanalocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Reserastatin phosphate sodium; BPR-0Y-007 (National Health Research Institutes); SSR-250411 (Sanofi); Combretastatin A4; and analogs and derivatives thereof.

Figure 2:
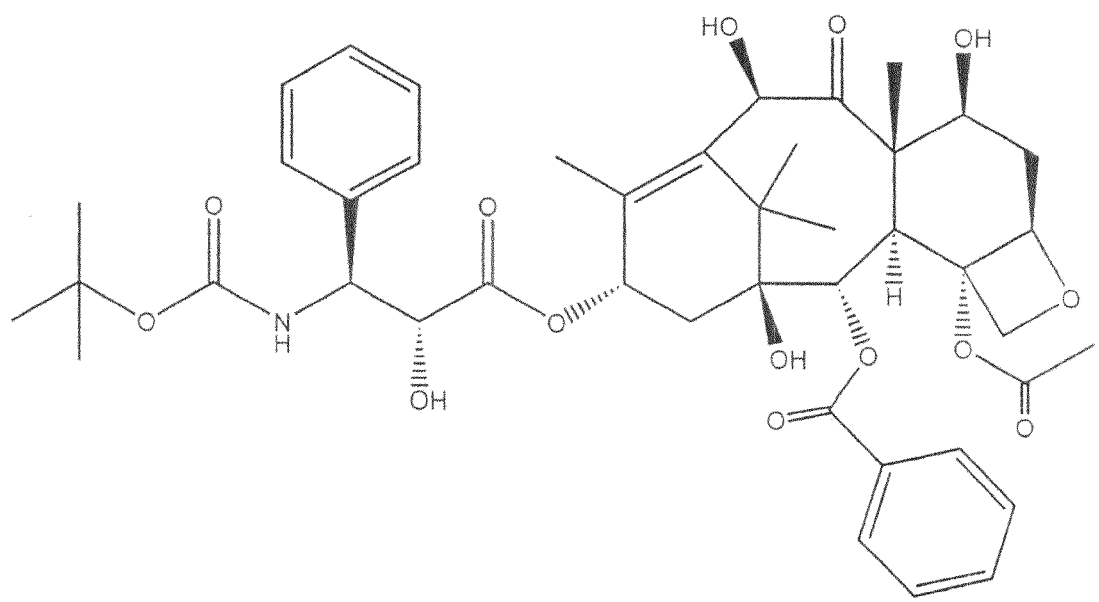
FIG. 2 is the structure of docetaxol (Taxotere®).
Figure 3:
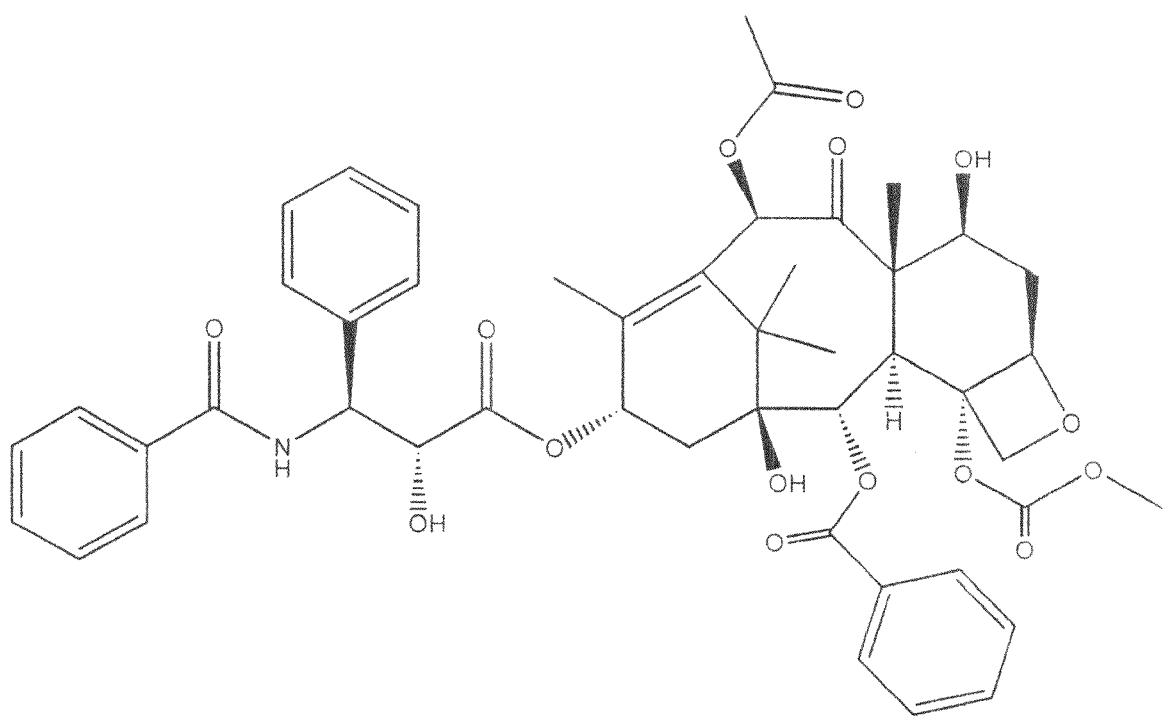
FIGS. 3-23 are each the structure of a paclitaxel analog.
Figure 4:
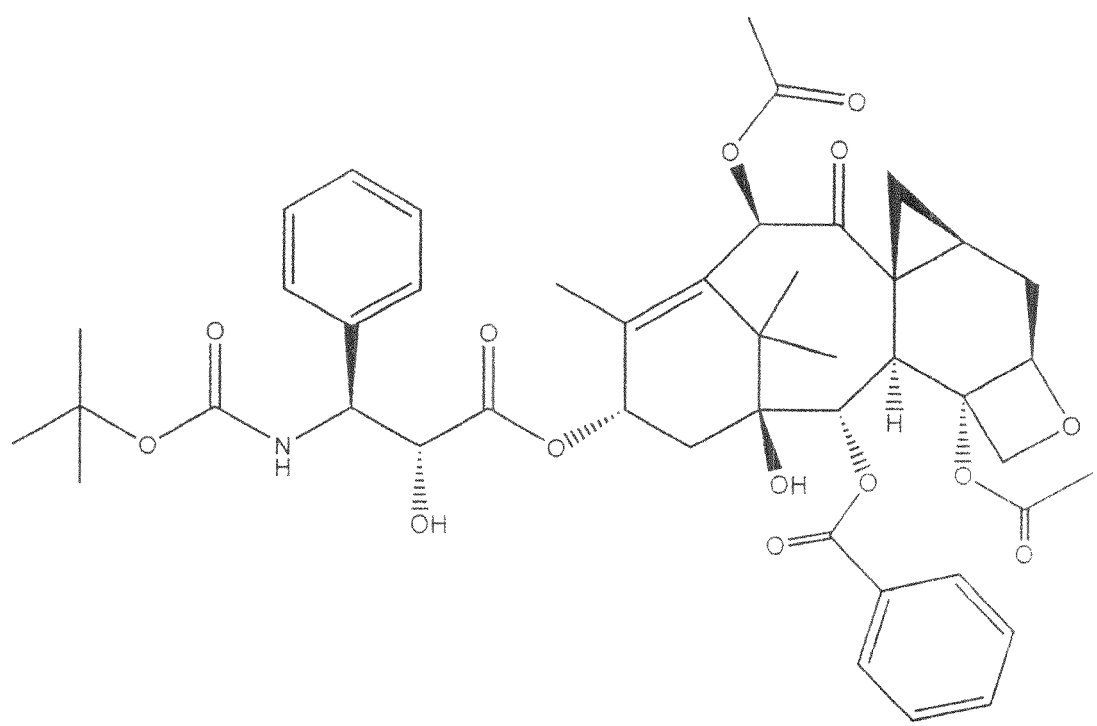
Figure 5:
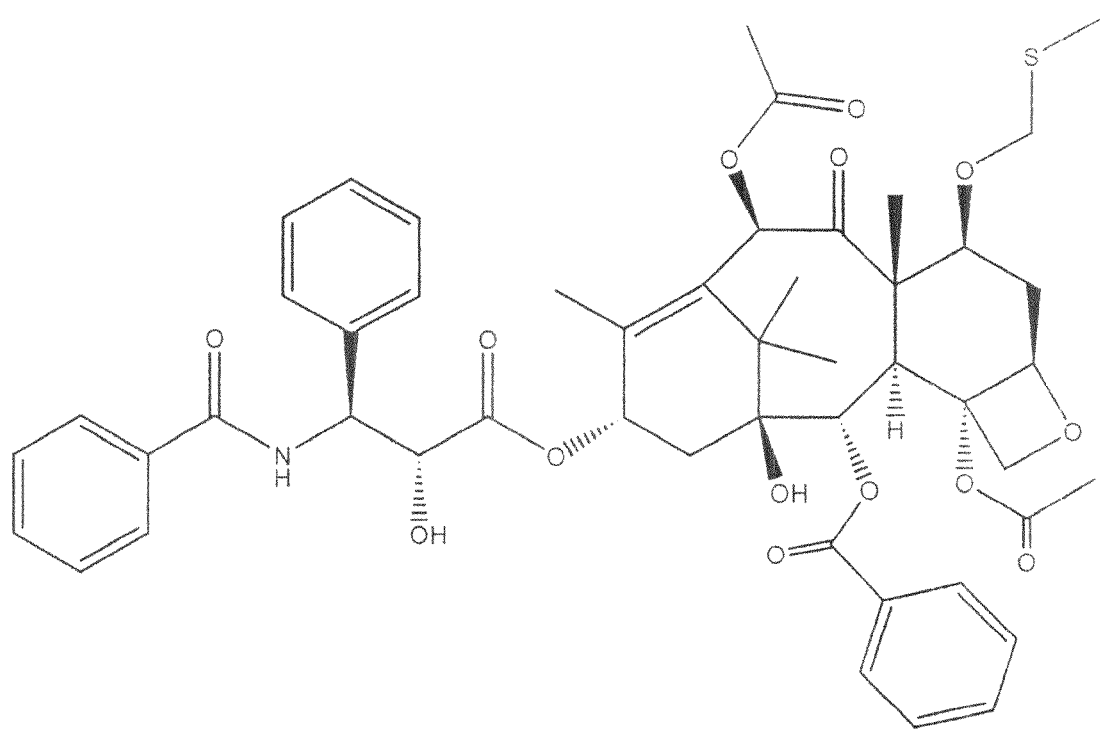
Figure 6:
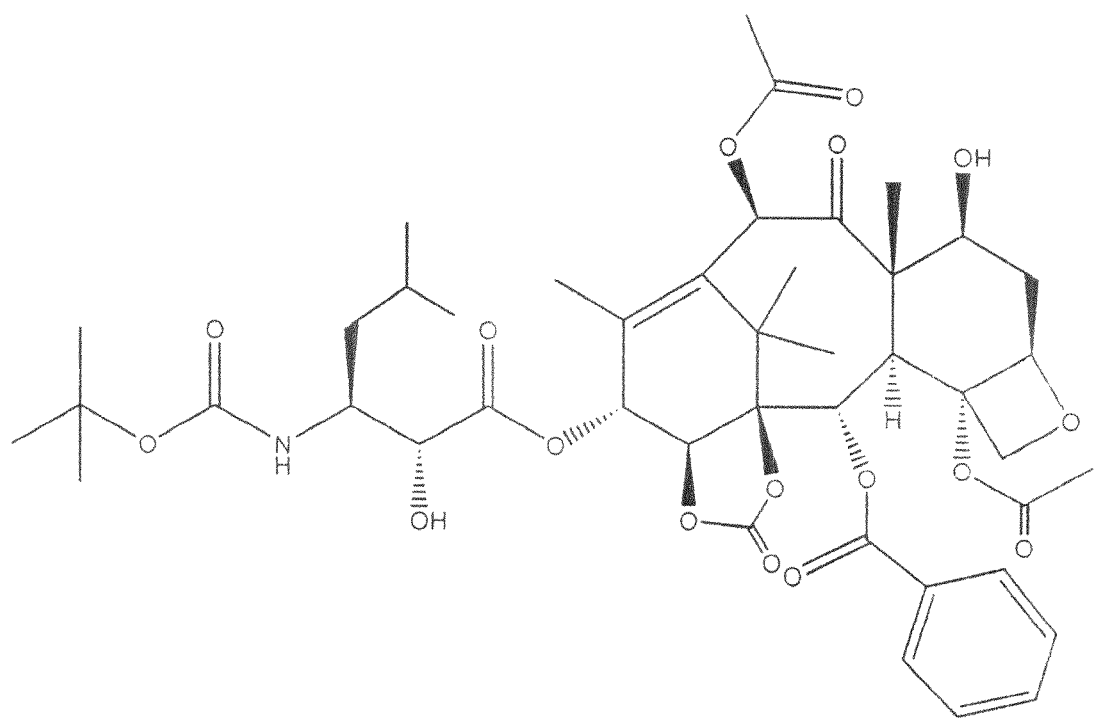
Figure 7:
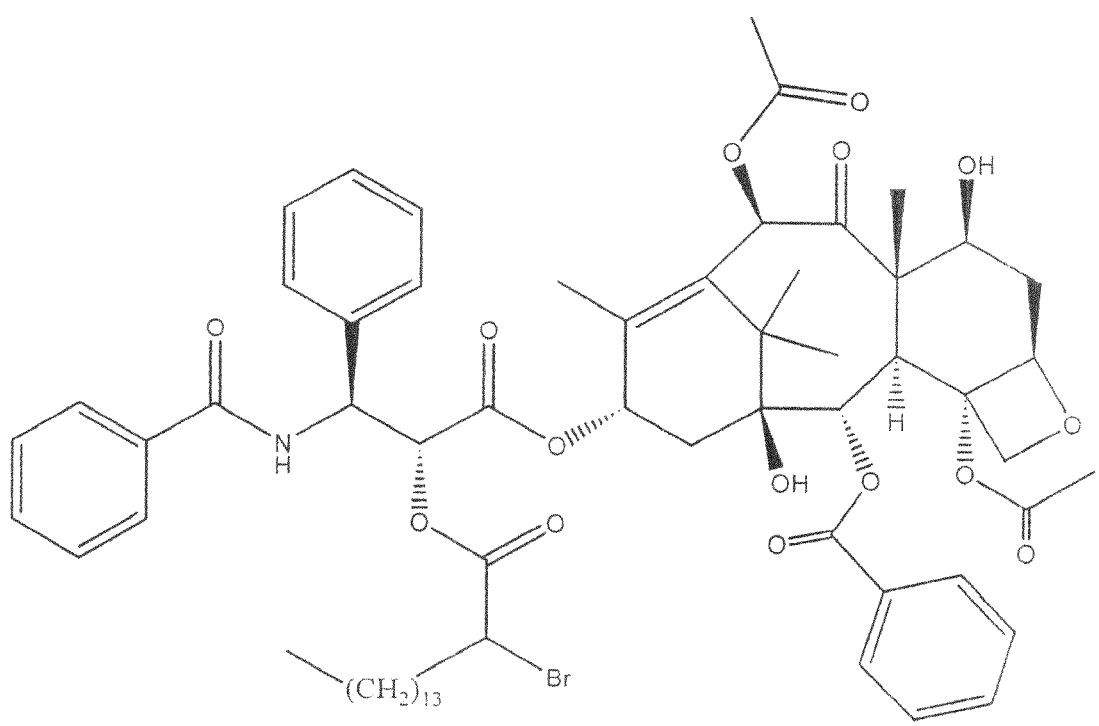
Figure 8:
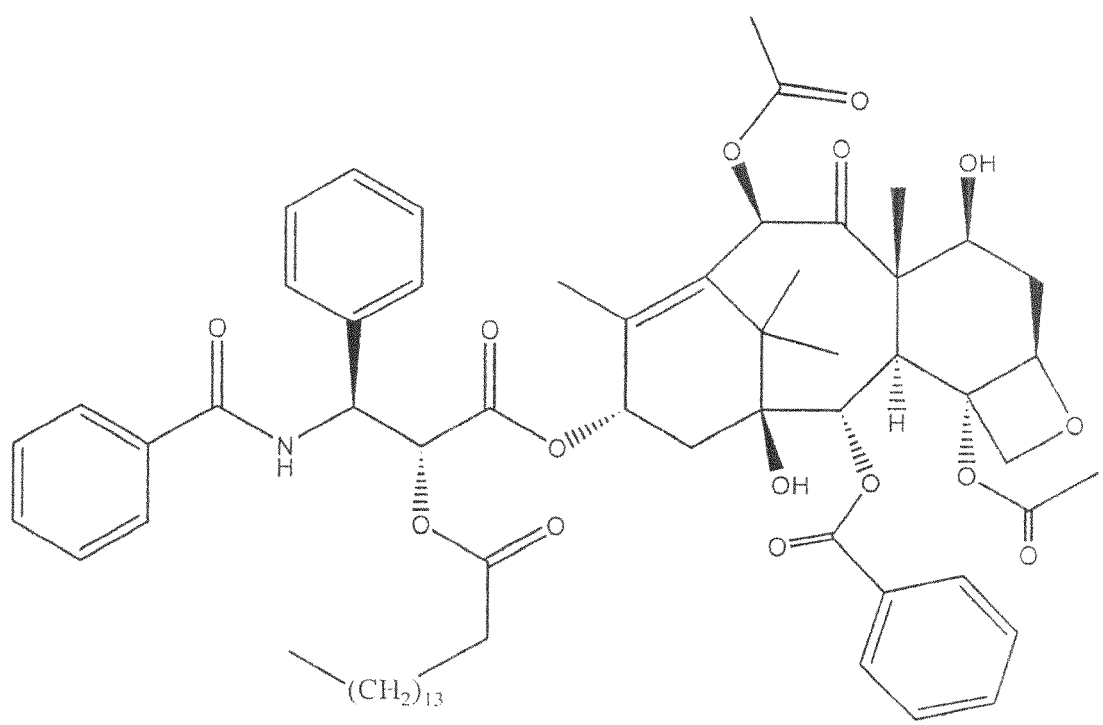
Figure 9:
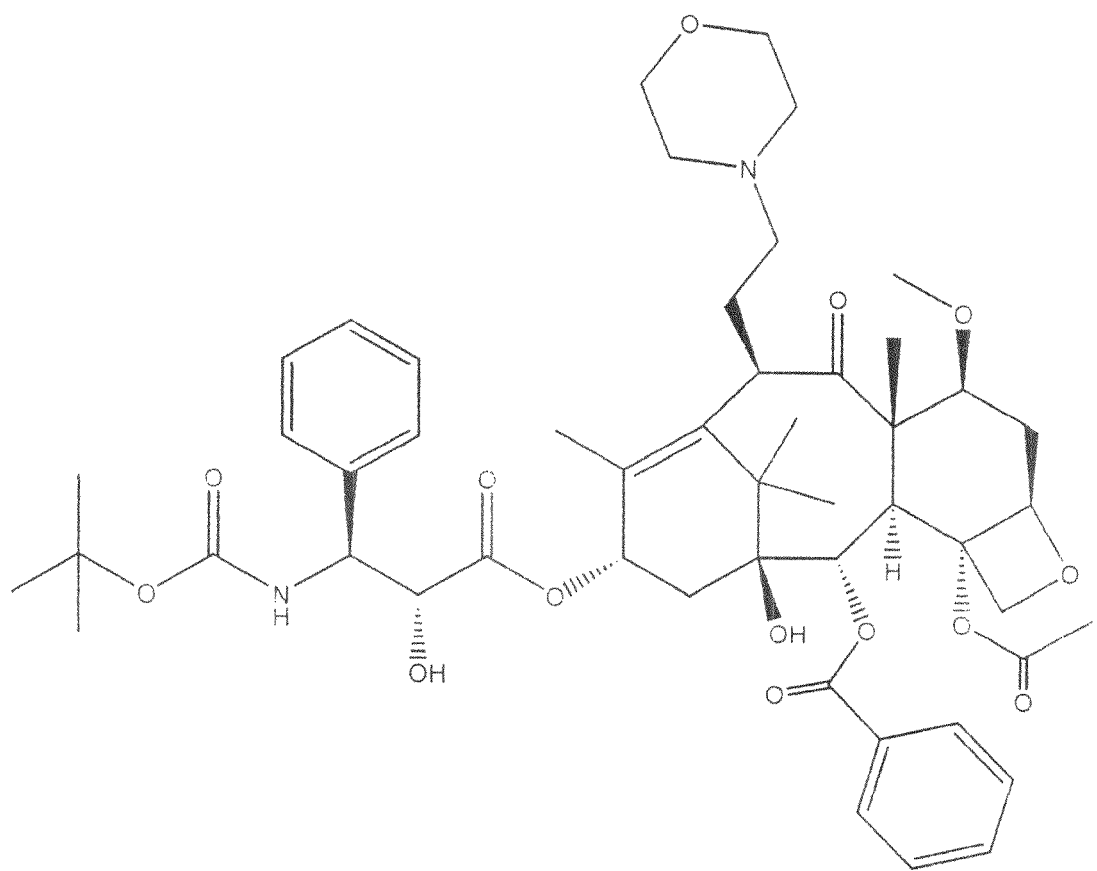
Figure 10:
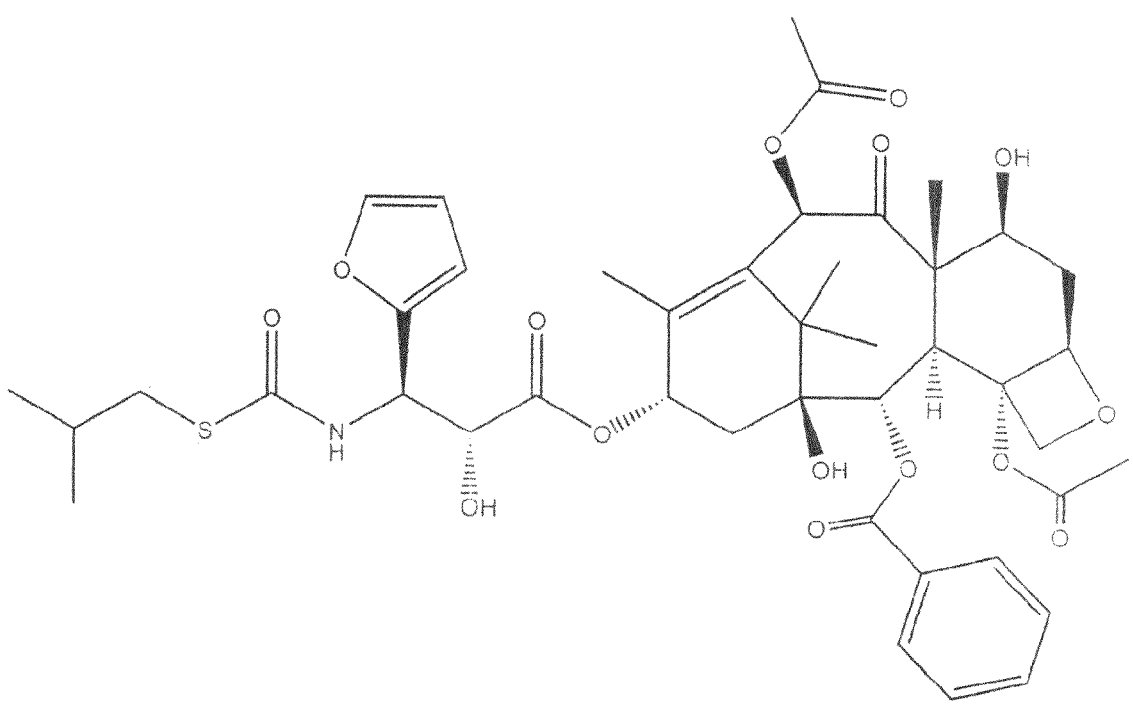
Figure 11:
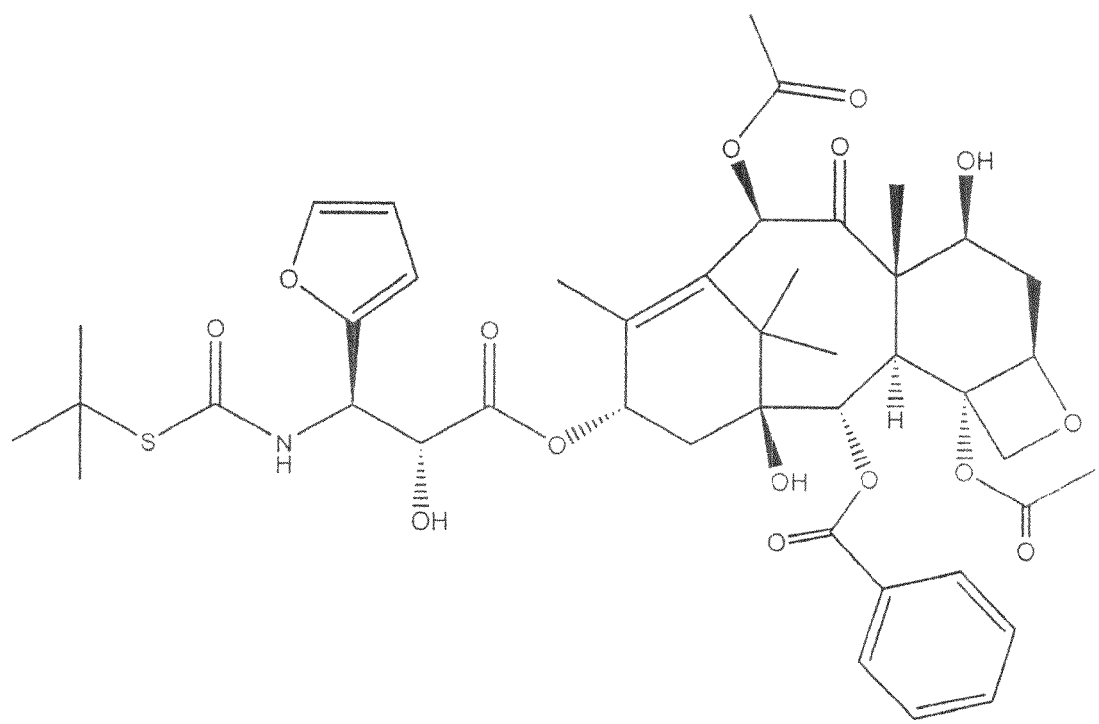
Figure 12:
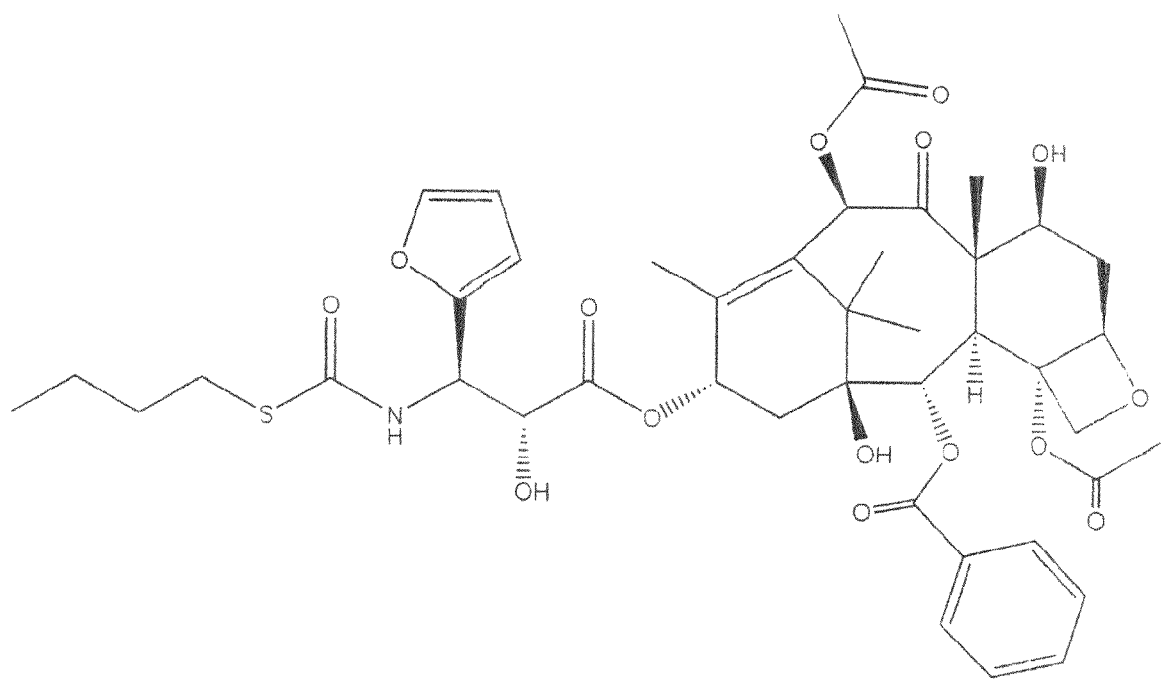
Figure 13:
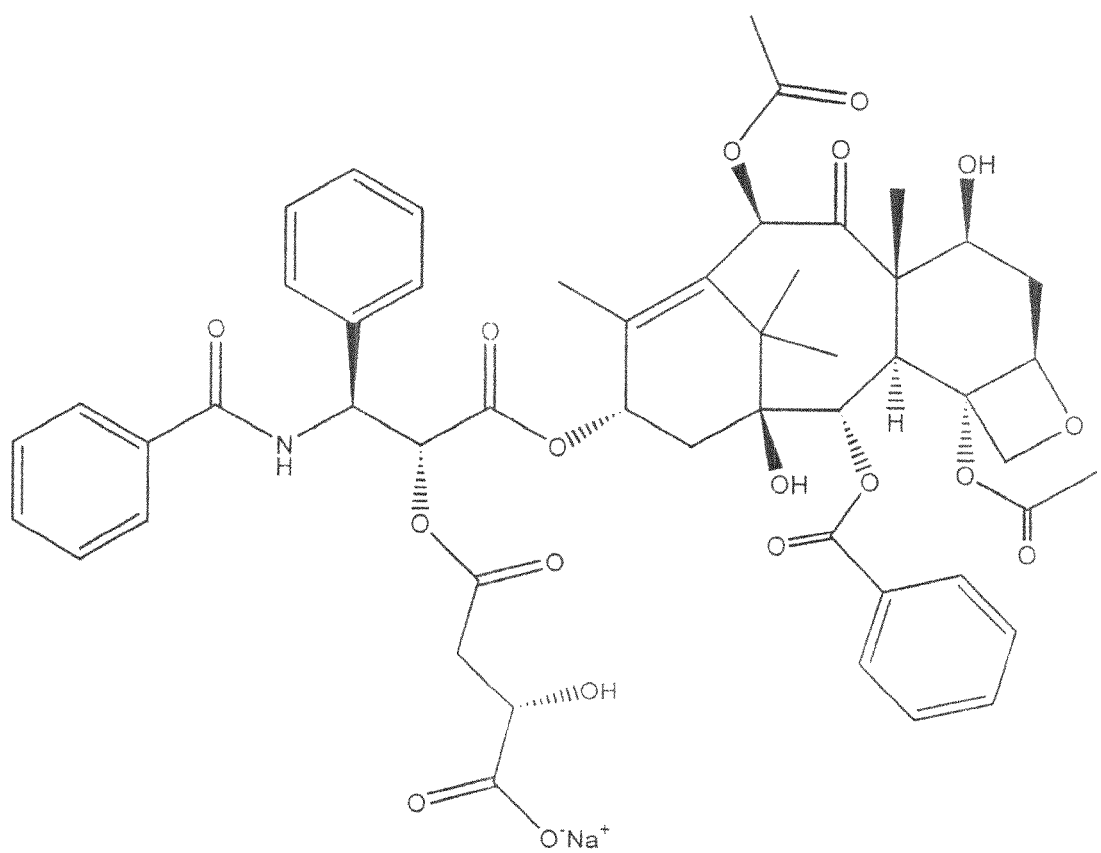
Figure 14:
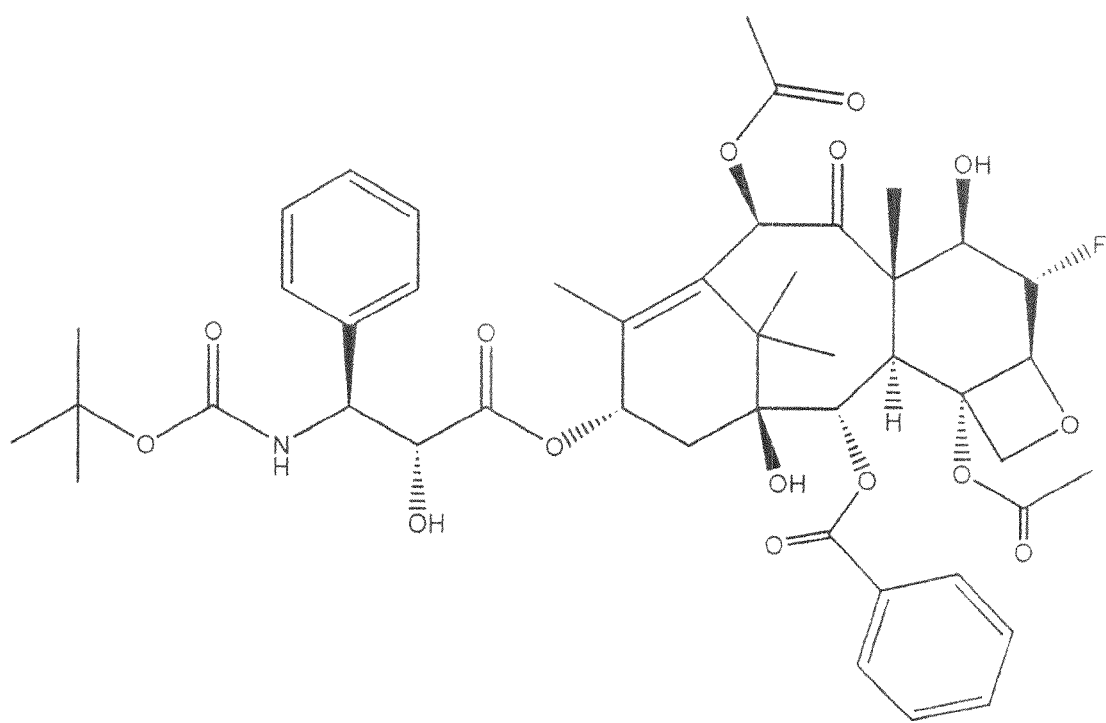
Figure 15:
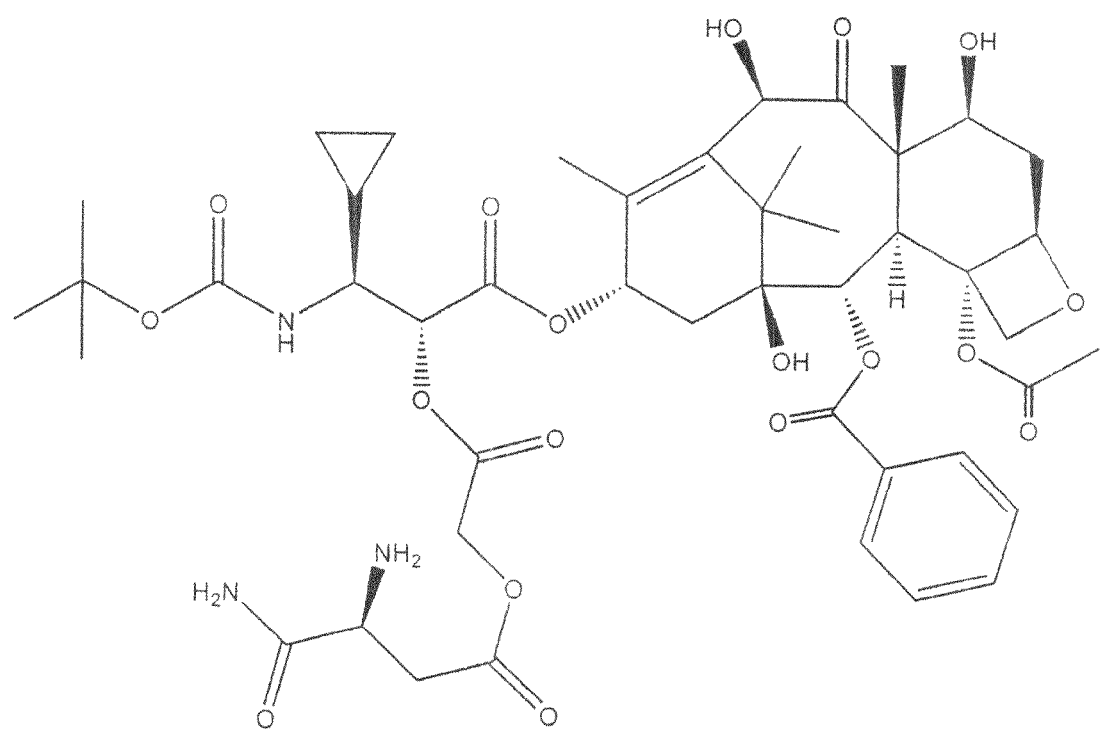
Figure 16:
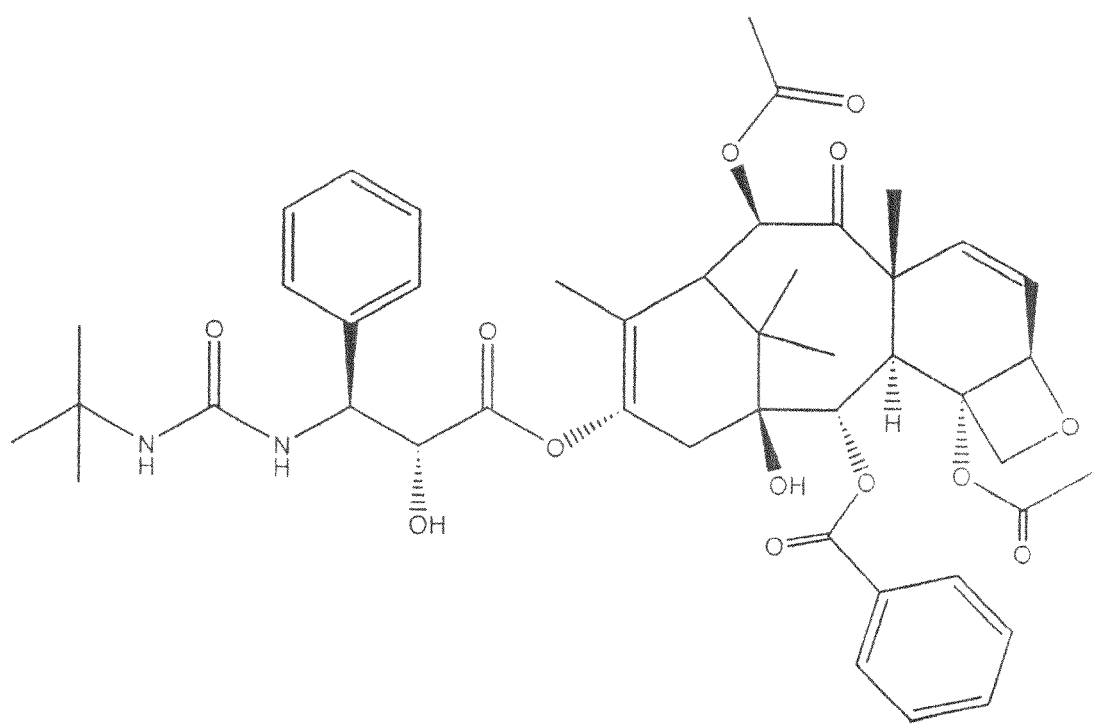
Figure 17:
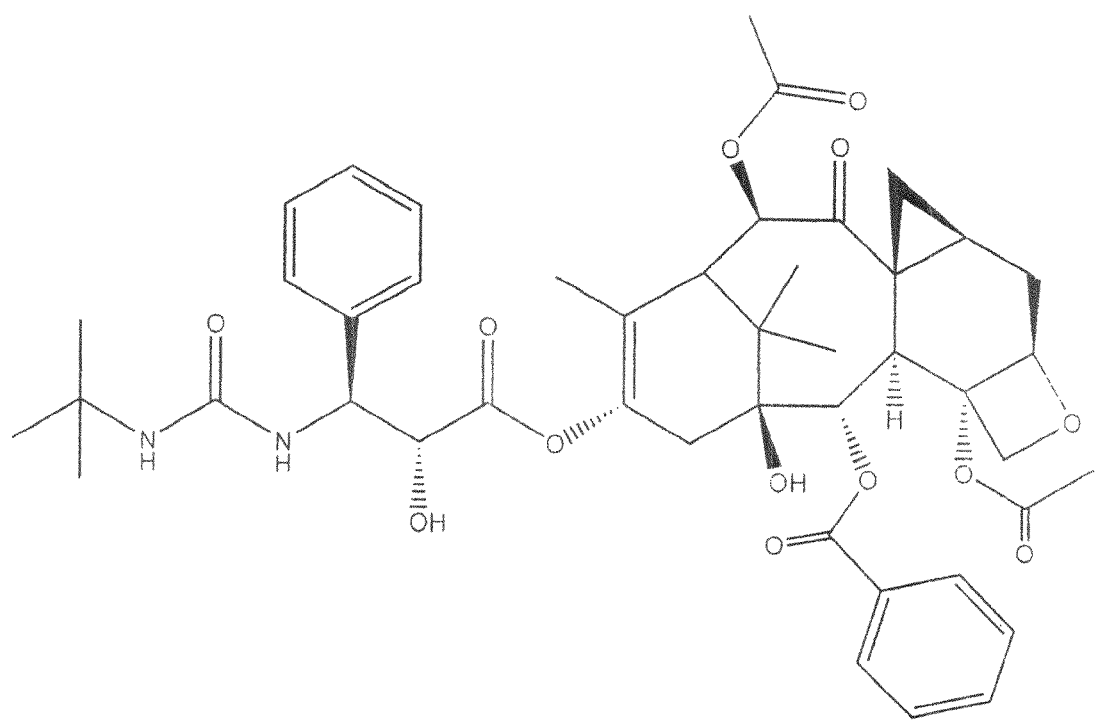
Figure 18:
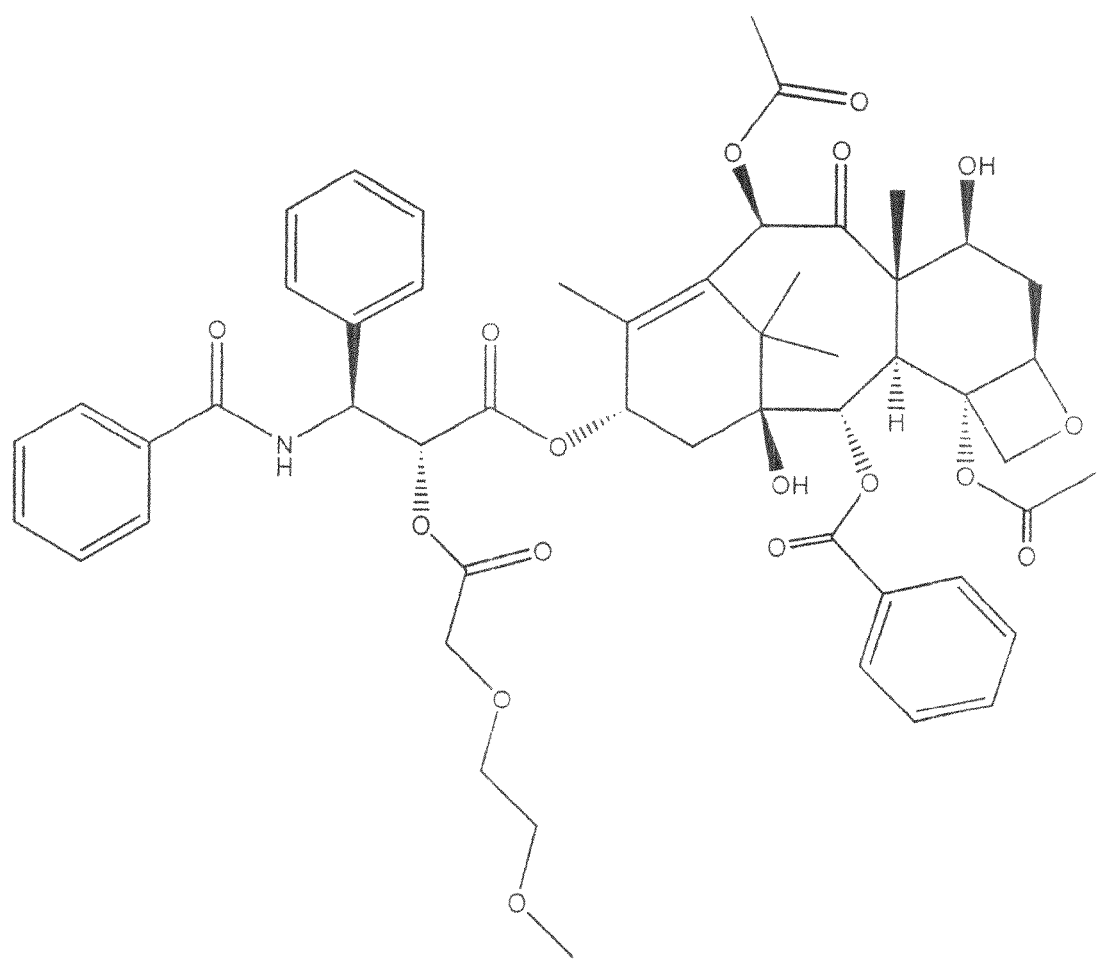
Figure 19:
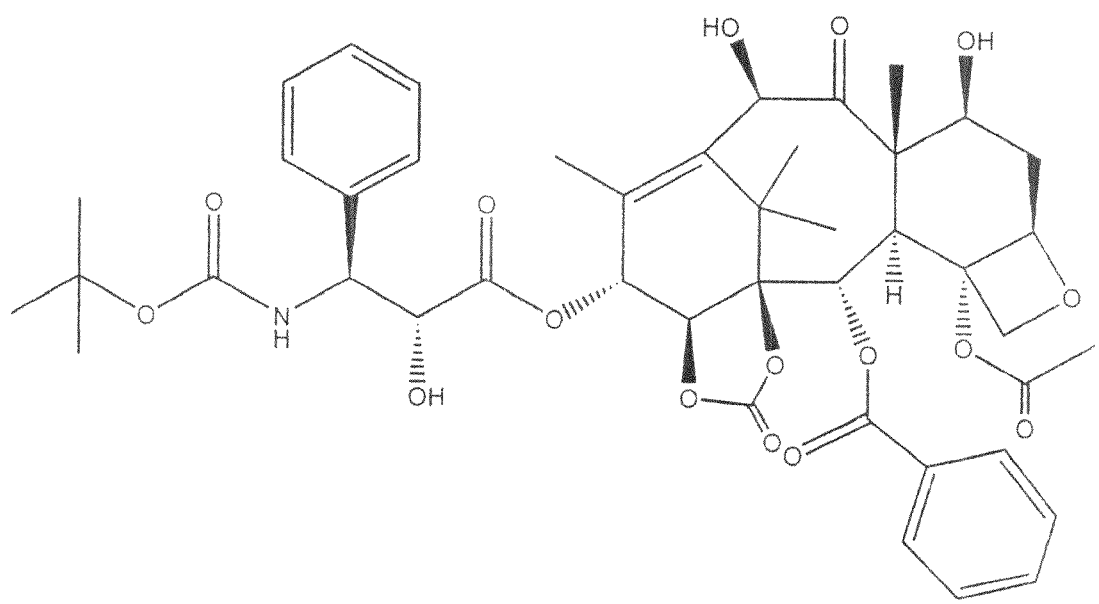
Figure 20:
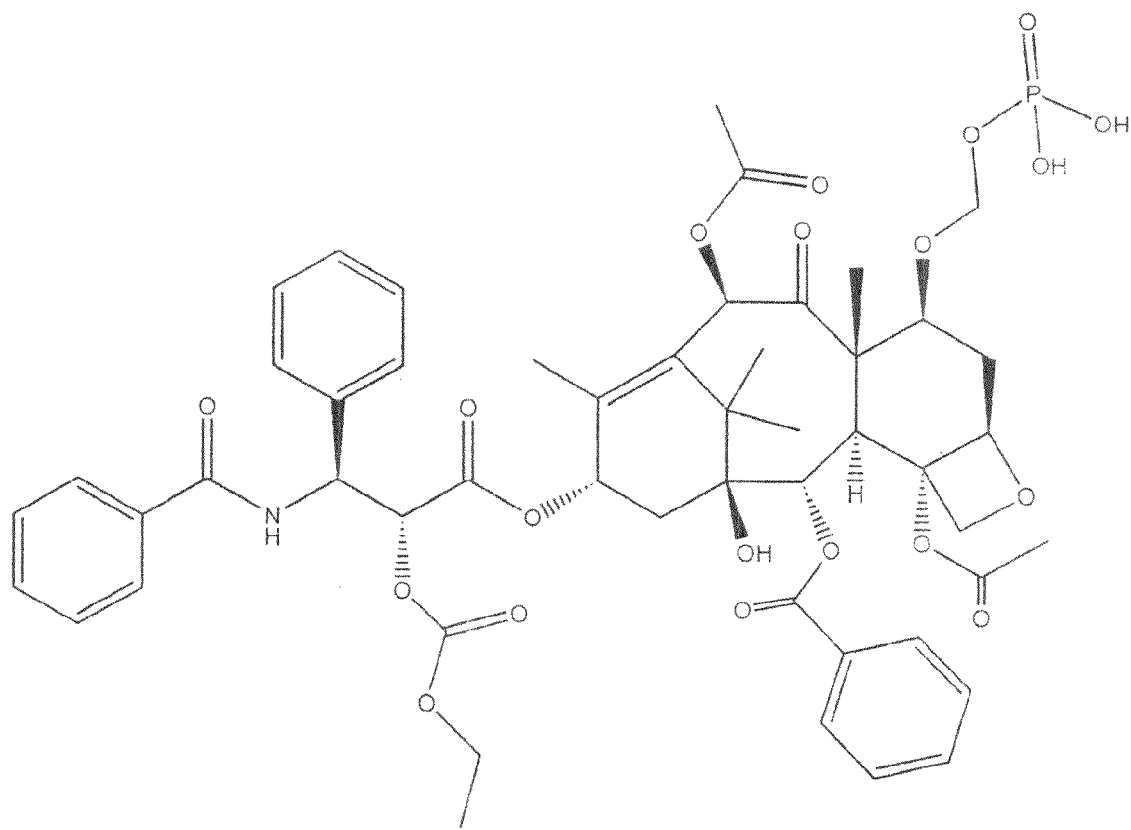
Figure 21:
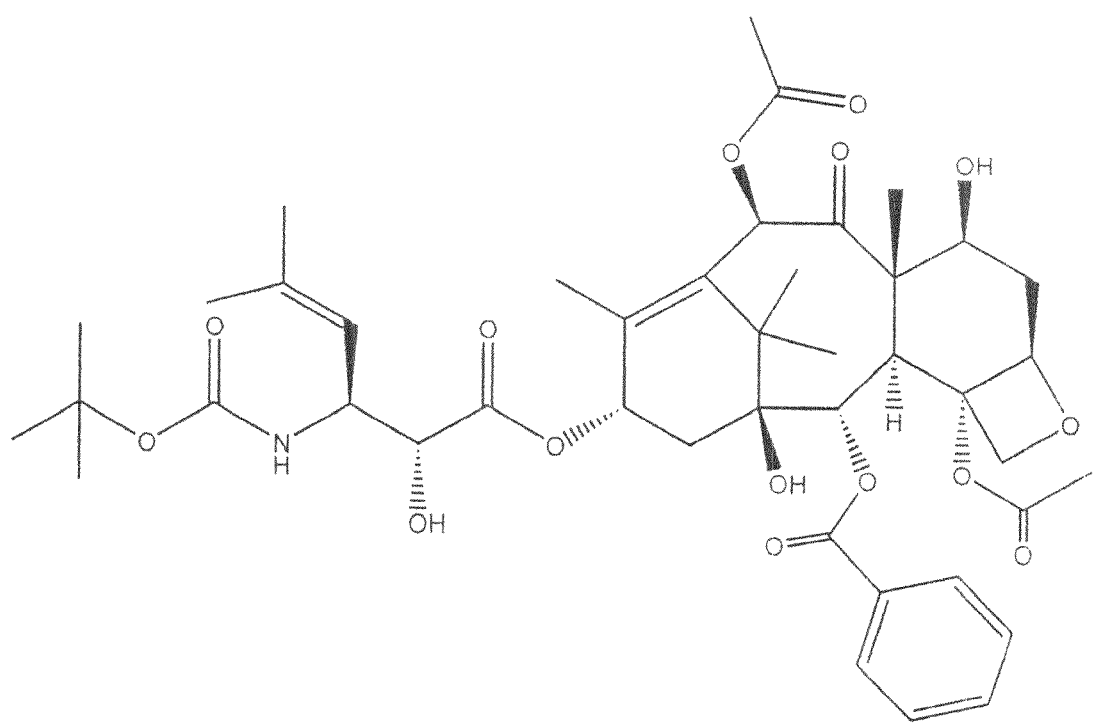
Figure 22:
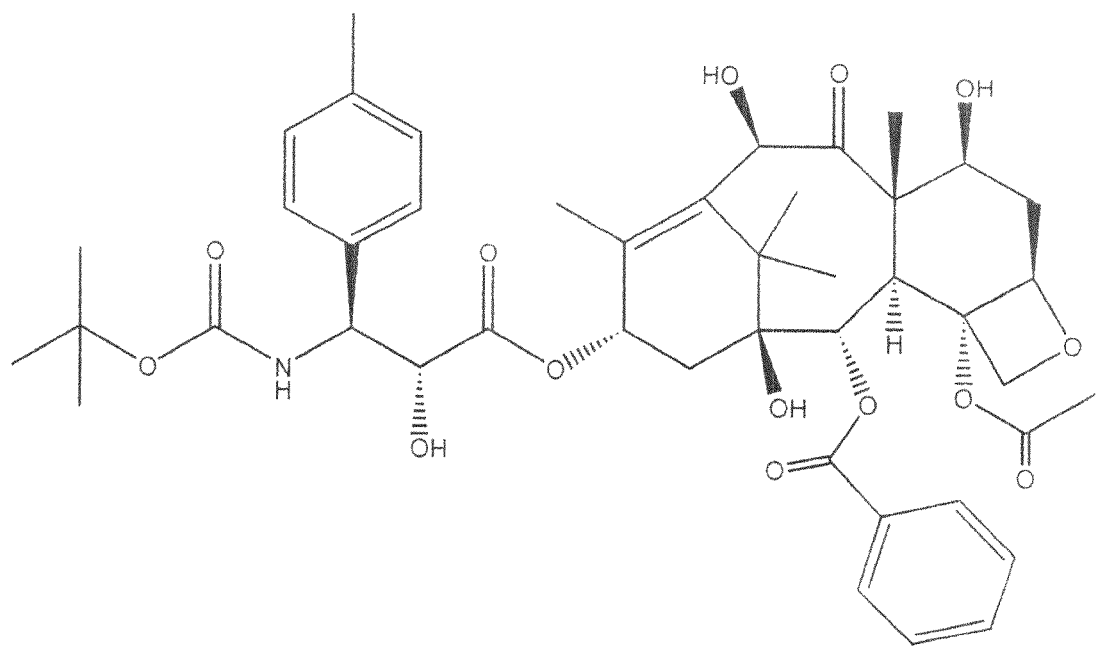
Figure 23:
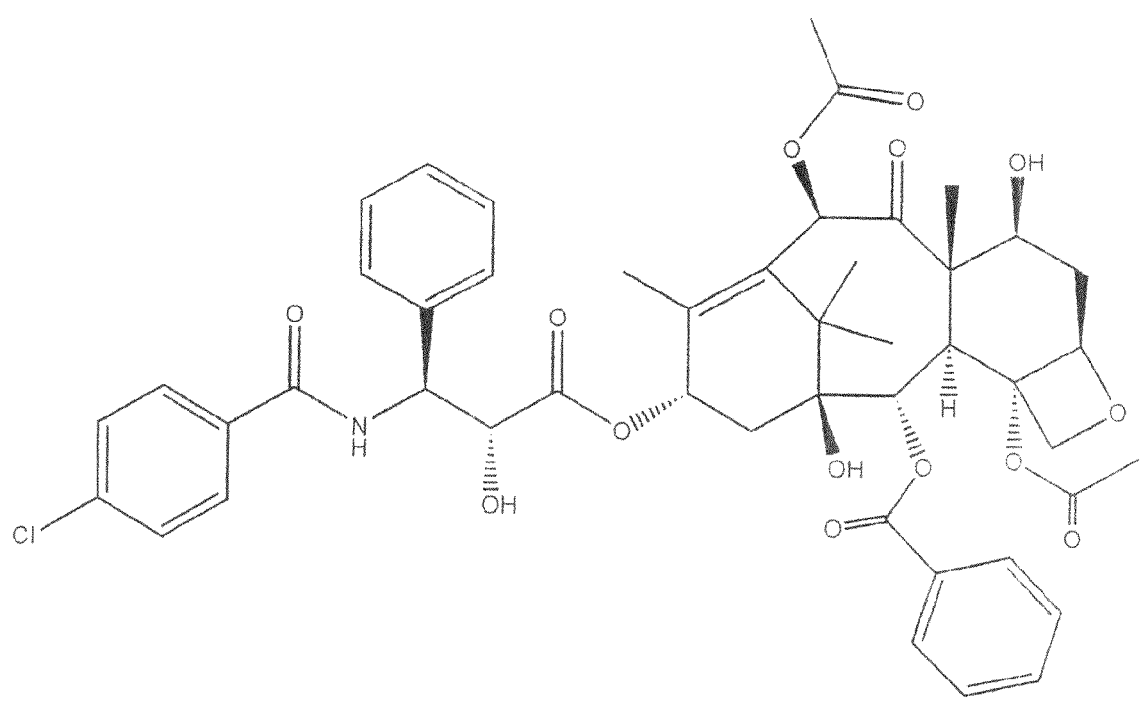

Paclitaxel, also referred to as "Taxol®", is a well-known anti-cancer drug which acts by enhancing and stabilizing microtubule formation. The structure of paclitaxel is shown in FIG. 1. Many analogs of paclitaxel are known, including Taxotere®, the structure of which is shown in FIG. 2. Docetaxol is also referred to as "Taxotere®". The structures of other paclitaxel analogs are shown in FIGS. 3-23. These compounds have the basic taxane skeleton as a common structure feature and have also been shown to have the ability to arrest cells in the G2-M phases due to stabilization of microtubules. Thus, it is apparent from FIGS. 3-23 that a wide variety of substituents can decorate the taxane skeleton without adversely affecting biological activity. It is also apparent that zero, one or both of the cyclohexane rings of a paclitaxel analog can have a double bond at the indicated positions. For clarity purposes, the basic taxane skeleton is shown below in Structural Formula (VI):

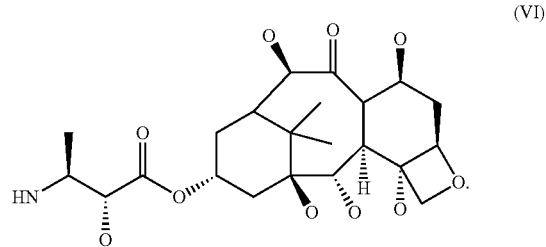

(VI)

Double bonds have been omitted from the cyclohexane rings in the taxane skeleton represented by Structural Formula (VI). The basic taxane skeleton can include zero or one double bond in one or both cyclohexane rings, as indicated in FIGS. 3-23 and Structural Formulas (VII) and (VIII) below. A number of atoms have also been omitted from Structural Formula (VI) to indicate sites in which structural variation commonly occurs among paclitaxel analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "paclitaxel analog" is defined herein to mean a compound which has the basic taxane skeleton and which promotes microtubule formation. Paclitaxel analogs may be formulated as a nanoparticle colloidal composition to improve the infusion time and to eliminate the need to deliver the drug with Cremophor which causes hypersensitivity reactions in some patients. An example of a paclitaxel analog formulated as a nanoparticle colloidal composition is Abraxane which is a nanopartiele colloidal composition of protein-stabilized paclitaxel that is reconstituted in saline.

Typically, the paclitaxel analogs used herein are represented by Structural Formula (VII) or (VIII):

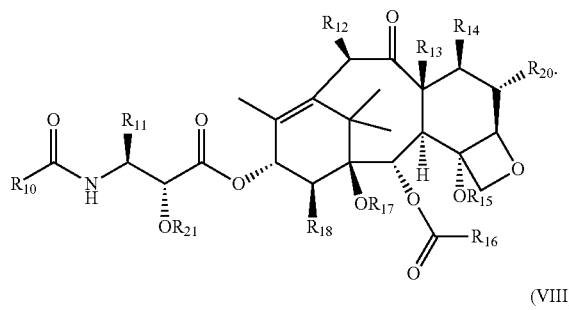

(VII)

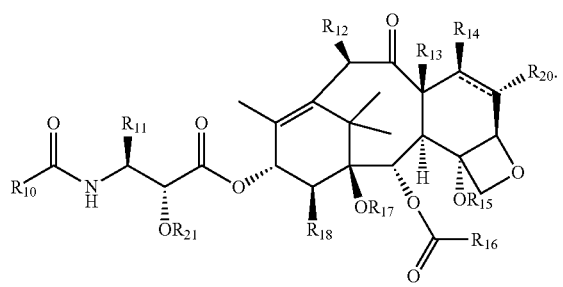

(VIII)

$R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl)-S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —OC(O)—O(lower alkyl), —OC(O)—O(substituted lower alkyl), —OC(O)—NH (lower alkyl) or —OC(O)—NH(substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (VII) and (VIII) are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH=C(CH$_3$)$_2$ or para-chlorophenyl; $R_{11}$ is phenyl, (CH$_3$)$_2$CHCH$_2$—, -2-furanyl, cyclopropyl or para-toluoyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—; $R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 24:
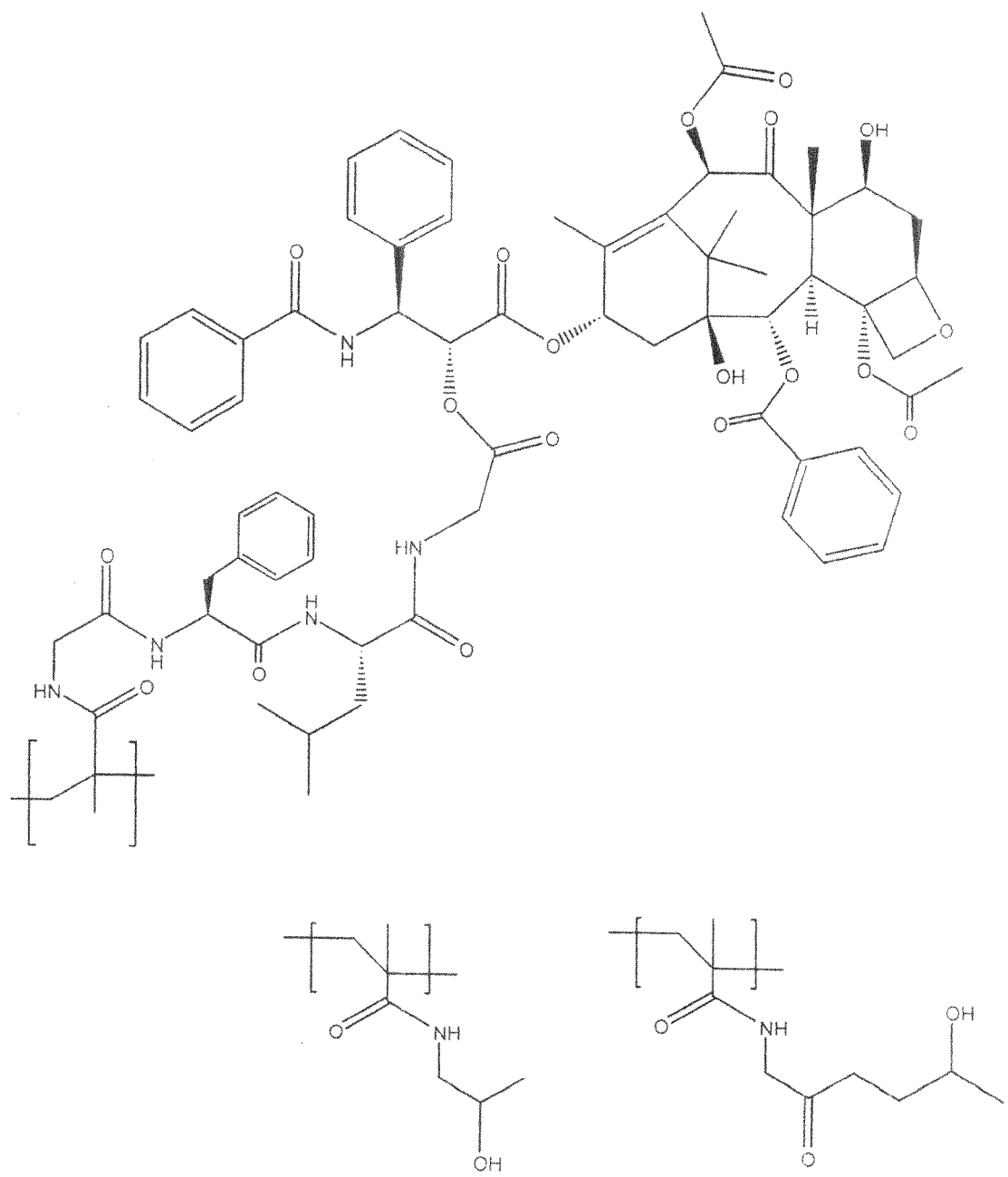
FIG. 24 is the structure of a polymer comprising a paclitaxel analog group pendent from the polymer backbone. The polymer is a terpolymer of the three monomer units shown.

A paclitaxel analog can also be bonded to or be pendent from a pharmaceutically acceptable polymer, such as a polyacrylamide. One example of a polymer of this type is shown in FIG. 24. The term "paclitaxel analog", as it is used herein, includes such polymers.

In some embodiments, paclitaxel analogs have a taxane skeleton represented by Structural Formula IX, wherein W is O, S, or NR. Paclitaxel analogs that have the taxane skeleton shown in Structural Formula IX can have various substituents attached to the taxane skeleton and can have a double bond in zero, one or both of the cyclohexane rings as shown, for example in FIGS. 3-23.

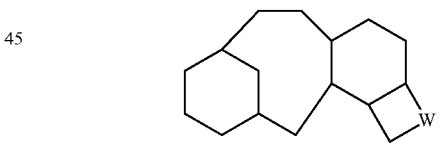

(IX)

Various paclitaxel analogs and paclitaxel formulations are described in Hennenfent et al. (2006)*Annals of Oncology* 17:735-749; Gradishar (2006)*Expert Opin. Pharmaeother.* 7(8):1041-53; Attard et. al. (2006)*Pathol Biol* 54(2):72-84; Straubinger et al. (2005)*Methods Enzymol.* 391:97-117; Ten Tije et al. (2003) *Clin Pharmacokinet.* 42(7):665-85; and Nuijen et al. (2001) *Invest New Drugs.* 19(2):143-53, the entire teachings of which are incorporated herein by reference.

In co-therapy in combination with one or more other therapeutic agents (e.g., paclitaxel or paclitaxel analogs), the compound or the pharmaceutical composition disclosed herein can be administered simultaneously or separately with the other therapeutic agent(s). The exact details of the administration will depend on the pharmacokinetics of the two substances in the presence of each other, and can include administering two substances substantially at the same time, and one substance within a certain time period (e.g., within 24 hours) of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

In one embodiment, the present invention is directed to a method of treating a subject with a Hsp70-responsive disorder. The method comprises administering to the subject an effective amount of a compound or a pharmaceutical composition describe herein.

As used herein, "Hsp70" includes each member of the family of heat shock proteins having a mass of about 70-kiloDaltons, including forms such as constituitive, cognate, cell-specific, glucose-regulated, inducible, etc. Examples of specific Hsp70 proteins include hsp70, hsp70hom; hsc70; (Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. In humans, the Hsp70 family encompasses at least 11 genes encoding a group of highly related proteins. See, for example, Tavaria, et al., Cell Stress Chaperones, 1996; 1(1): 23-28; Todryk, et al., Immunology. 2003, 110(1): 1-9; and Georgopoulos and Welch, Annu Rev Cell Biol. 1993; 9:601-634; the entire teachings of these documents are incorporated herein by reference.

As used herein, an "Hsp70-responsive disorder" is a medical condition wherein stressed cells can be treated by increased Hsp70 expression. Such disorders can be caused by a wide variety of cellular stressors, including, but not limited to Alzheimer's disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; autoimmune disease; infection (bacterial, viral, fungal, or parasitic); and the like.

In some embodiments, the Hsp70-responsive disorder is a neurodegenerative disorder. As used herein, a neurodegenerative disorder involves degradation of neurons such as cerebral, spinal, and peripheral neurons (e.g., at neuromuscular junctions), more typically degradation of cerebral and spinal neurons, or in preferred embodiments, degradation of cerebral neurons. Neurodegenerative disorders can include Alzheimer's disease; Huntington's disease; Parkinson's disease; spinal/bulbar muscular atrophy and other neuromuscular atrophies; and familial amyotrophic lateral sclerosis or other diseases associated with superoxide dismutase (SOD) mutations. Neurodegenerative disorders can also include degradation of neurons caused by ischemia, seizure, thermal stress, radiation, toxin exposure, infection, injury, and the like.

In some embodiments, the Hsp70-responsive disorder is a disorder of protein aggregation/misfolding, such as Alzheimer's disease; Huntington's disease; Parkinson's disease; spongiform encephalopathies; and the like.

In another embodiment the Hsp70-responsive disorder is a treatment or condition which causes or may cause nerve damage. The compounds for use in the methods of the present invention can be used to reduce or prevent (inhibit the onset of) nerve damage (i.e., provide neuroprotection) in a subject i) suffering from a condition which causes or may cause nerve damage or ii) receiving treatment which causes or may cause nerve damage. In one aspect, the treatment which causes or may cause nerve damage is radiation therapy. In another aspect, the treatment is chemotherapy. In one aspect, the chemotherapy comprises administering an antimitotic agent (e.g. vincristine, vinorelbine, paclitaxel, or a paclitaxel analog). In one aspect, the chemotherapy comprises administering paclitaxel. En another aspect, the chemotherapy comprises administering a platinum derivative (e.g. cisplatin, carboplatin, or oxaliplatin). In certain embodiments, the compounds for use in the methods of the present invention can be administered simultaneously as a combination therapy with the treatment which causes or may cause nerve damage. In other embodiments the compounds for use in the methods of the present invention can be administered before or after the treatment which causes may cause nerve damage. In certain embodiments the compounds for use in the methods of the present invention can be administered between 30 minutes and 12 hours, between 1 hour and 6 before or after the treatment which causes or may cause nerve damage.

Nerve damage may be caused by a number of treatments including, but not limited to, radiation therapy; chemotherapy, e.g. cisplatin, carboplatin, oxaliplatin, vincristine, vinblastine, vinorelbine, vindesine, ifosfamide, methotrexate, cladribine, altretamine, fludarabine, procarbazine, thiotepa, teniposide, arsenic trioxide, alemtuzumab, capecitabine, dacarbazine, denileukin diftitox, interferon alpha, liposomal daunorubicin, tretinoin, etoposide/VP-16, cytarabine, hexamethylmelamine, suramin, paclitaxel, docetaxel, gemcitibine, thalidomide, and bortezomib; heart or blood pressure medications, e.g. amiodarone, hydralazine, digoxin, and perhxiline; medications to fight infection, e.g. metronidazole, nitrofurantoin, thalidomide, and INH; medications to treat skin conditions, e.g. dapsone; anticonvulsants, e.g. phenyloin; anti-alcohol medications, e.g. disulfiram; HIV medications, e.g. zidovudine, didanonsine, stavudine, zalcitabine, ritonavir, d4T, ddC, ddl, and amprenavir; cholesterol medications, e.g. lovastatin, pravastatin, indapamid, simvastatin, fluvastatin, atorvastatin, cerivastatin, and gemfibrozil; anti-rheumatics, e.g. chloroquine, cholchicine, organic gold, and penicillamine; nitrous oxide; lithium; and ergots.

In some embodiments, the HSP70-responsive disorder is ischemia. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like. In one preferred embodiment, the Hsp70-responsive disorder is cerebral or spinal ischemia. In another preferred embodiment, the Hsp70-responsive disorder is cardiac ischemia.

In various embodiments, the Hsp70-responsive disorder is seizure, e.g., epileptic seizure, injury-induced seizure, chemically-induced seizure, and the like.

In some embodiments, the Hsp70-responsive disorder is due to thermal stress. Thermal stress includes hyperthermia (e.g., from fever, heat stroke, burns, and the like) and hypothermia. In a preferred embodiment the disorder is hyperthermia. In another preferred embodiment, the Hsp70-responsive disorder is burn trauma.

In preferred embodiments, the Hsp70-responsive disorder is atherosclerosis.

In various embodiments, the Hsp70-responsive disorder is radiation damage, e.g., due to visible light, ultraviolet light, microwaves, cosmic rays, alpha radiation, beta radiation, gamma radiation, X-rays, and the like. For example, the damage could be radiation damage to non-cancerous tissue in a subject treated for cancer by radiation therapy. In a preferred embodiment, the Hsp70-responsive disorder is radiation damage from visible light or ultraviolet light.

In various embodiments, the Hsp70-responsive disorder is mechanical injury, e.g., trauma from surgery, accidents, certain disease conditions (e.g., pressure damage in glaucoma) and the like. In a preferred embodiment, the Hsp70-responsive disorder is cerebral or spinal trauma. In another preferred embodiment, the Hsp70-responsive disorder is glaucoma (leading to pressure damage to retinal ganglions).

In various embodiments, the Hsp70-responsive disorder is exposure to a toxin. In preferred embodiments, the Hsp70-responsive disorder is exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

The present invention also provides a method of treating a subject with a natural killer, cell-responsive disorder, wherein the method comprises administering to the subject an effective amount of a compound or a pharmaceutical composition describe herein.

Certain compounds of the invention also increase Natural Killer (NK) cell activity. As used herein, a "NK cell-responsive disorder" is a medical condition which is improved by an increased in NK cell activity. For example, a subject with a NK cell-responsive disorder may need immune system augmentation because of infection or the possibility thereof. In some embodiments, such a subject can have an infection (or has been exposed to an infectious environment where pathogens are present, e.g., in a hospital) the symptoms of which may be alleviated by the methods disclosed herein. For example, a subject in need of treatment can have an infection (bacterial, viral, fungal, or parasitical (protozoal) for which the disclosed methods of activating NK cells can be a treatment.

In some embodiments, a subject having an NK cell-responsive disorder has an immunodeficiency. Such a subject is in need of or can benefit from prophylactic therapy, for example, a subject that has incomplete, damaged or otherwise compromised defenses against infection, or is subject to an infective environment, or the like. For example, a subject can be in an infectious environment where pathogens are present, e.g., in a hospital; can have an open wound or burn injury; can have an inherited or acquired immune deficiency (e.g., severe combined immunodeficiency or "bubble boy" syndrome, variable immunodeficiency syndrome acquired immune deficiency syndrome (AIDS), or the like); can have a depressed immune system due to physical condition, age, toxin exposure, drug effect (immunosuppressants, e.g., in a transplant recipient) or side effect (e.g., due to an anticancer agent); or the like.

In some embodiments, NK cell activity can be increased in subjects that have decreased or deficient NK cell activity, in conditions such as chronic fatigue syndrome (chronic fatigue immune dysfunction syndrome) or Epstein-Barr virus infection, post viral fatigue syndrome, post-transplantation syndrome (especially allogeneic transplants) or host-graft disease, exposure to drugs such as anticancer agents or nitric oxide synthase inhibitors, natural aging, and various immunodeficient conditions such as severe combined immunodeficiency, variable immunodeficiency syndrome, and the like.

In some embodiments, a subject having an NK cell-responsive disorder is in need of treatment for bacteremia. Bacteremia is the condition of bacterial infection in the bloodstream. Septic shock includes serious localized or bacteremic infection accompanied by systemic inflammation, in other words sepsis with hypoperfusion and hypotension refractory to fluid therapy. Sepsis, or systemic inflammatory response syndrome, includes various severe conditions such as infections, pancreatitis, burns, trauma) that can cause acute inflammation. Septic shock is typically related to infections by gram-negative organisms, staphylococci, or meningoeocci. Septic shock can be characterized by acute circulatory failure, typically with hypotension, and multiorgan failure.

Transient bacteremia can be caused by surgical or trauma wounds. Gram-negative bacteremia can be intermittent and opportunistic; although it may have no effect on a healthy person, it may be seriously important in immunocompromised patients with debilitating underlying diseases, after chemotherapy, and in settings of malnutrition. The infection can typically be in the lungs, in the genitouritory (GU) or gastrointestinal (GI) tract, or in soft tissues, e.g., skin in patients with decubitus ulcer, oral ulcers in patients at risk, and patients with valvular heart disease, prosthetic heart valves, or other implanted prostheses.

Typically, gram-negative bacteremia can manifest in chronically ill and immunocompromised patients. Also in such patients, bloodstream infections can be caused by aerobic bacilli, anaerobes, and fungi. *Bacteroides* can lead to abdominal and pelvic infective complications, especially in females. Transient or sustained bactercmia can typically result in metastatic infection of the meninges or serous cavities, such as the pericardium or larger joints. *Enterococcus, staphylococcus*, or fungus can lead to endocarditis, but is less common with gram-negative bacteremia. Staphylococcal bacteremia can be typical of IV drug users, and can be a typical cause of gram-positive bacterial endocarditis.

The incidence of systemic fungal infections has undergone a significant increase, particularly in humans, due in part to increases in the number of subjects with compromised immune systems, for example, the elderly, AIDS patients, patients undergoing chemotherapy, burn patients, patients with diabetic ketoaeidosis, and transplant patients on immunosuppressive drugs. A study found that about 40% of deaths from infections acquired during hospitalization were due to mycoses; see Sternberg et. al, *Science*, Vol. 266, (1994), pp. 1632-1634, the entire teachings of which are incorporated herein by reference.

In various embodiments, the subject having an NK cell-responsive disorder can be in need of treatment for a fungal infection, such as a pathogenic dermatophyte, a pathogenic filamentous fungus, and/or a pathogenic non-filamentous fungus, e.g., a yeast, or the like. Pathogenic dermatophytes can include, e.g., species of the genera *Trichophyton, Tinea, Microsporum, Epidermophyton*, or the like. Pathogenic filamentous fungus can include, e.g., species of genera such as *Aspergillus, Histoplasma, Cryptococcus, Microsporum*, or the like. Pathogenic non-filamentous fungus, e.g., yeasts, can include, for example, species of the genera *Candida, Malassezia, Trichosporon, Rhodotorula, Torulopsis, Blastomyces, Paracoccidioides, Coccidioides*, or the like. In various embodiments, the subject can be treated for a fungal infection from a species of the genera *Aspergillus* or *Trichophyton*. Species of *Trichophyton* can include, for example, *Trichophyton mentagrophytes, Trichophyton rubrum, Trichophyton schoenleinii, Trichophyton tonsurans, Trichophyton verrucosum*, and *Trichophyton violaceum*, Species of *Aspergillus* can include, for example, *Aspergillus fumigatus, Aspergillus flavus, Aspergillus niger, Aspergillus amstelodami, Aspergillus candidus, Aspergillus carneus, Aspergillus nidulans, A*

*oryzae, Aspergillus restrictus, Aspergillus sydowi, Aspergillus terreus, Aspergillus ustus, Aspergillus versicolor, Aspergillus caesiellus, Aspergillus clavatus, Aspergillus avenaceus,* and *Aspergillus deflectus.* In some embodiments, the subject can be treated for a fungal infection from a pathogenic dermatophyte, e.g., *Trichophyton* (e.g., *Trichophyton rubrum*), *Tinea, Microsporum,* or *Epidermophyton;* or *Cryptococcus* (e.g., *Cryptococcus neolormans*) *Candida* (e.g., *Candida albicans*), *Paracoccidioides* e.g., *Paracoccidioides brasiliensis*), or *Coccidioides* (e.g., *Coccidioides immitis*). In particular embodiments, the subject can be treated for a fungal infection from *Trichophyton rubrum, Cryptococcus neoformans, Candida albicans, Paracoccidioides brasiliensis,* or *Coccidioides immitis.*

Thus, in various embodiments, a subject can have an infection caused by a fungus selected from the genera *Trichophyton, Tinea, Microsporum, Epidermophyton, Aspergillus, Histoplasma, Cryptococcus, Microsporum, Candida, Malassezia, Trichosporon, Rhodotorula, Torulopsis, Blastomyces, Paracoccidioides,* and *Coccidioides.* In some embodiments, the subject can have an infection caused by a fungus selected from the genera *Trichophyton, Tinea, Microsporum, Epidermophyton; Cryptococcus, Candida, Paracoccidioides,* and *Coccidioides.* In certain embodiments, the subject can have an infection caused by a fungus selected from *Trichophyton rubrum, Cryptococcus neoformans, Candida albicans, Paracoccidioides brasiliensis,* and *Coccidioides immitis.*

In various embodiments, the subject having an NK cell-responsive disorder can be in need of treatment for a bacterial infection caused, for example, by a bacteria of a genus selected from *Allochromatium, Acinetobacter, Bacillus, Campylobacter, Chlamydia, Chlamydophila, Clostridium, Citrobacter, Escherichia, Enterobacter, Enterococcus, Francisella, Haemophilus, Helicobacter, Klebsiella, Listeria, Moraxella, Mycobacterium, Micrococcus, Neisseria, Proteus, Pseudomonas, Salmonella, Serratia, Shigella, Stenotrophomonas, Staphyloccocus, Streptococcus, Synechococcus, Vibrio,* and *Yersina;* or anerobic bacterial genera such as *Peptostreptococci, Porphyromonas, Actinomyces, Clostridium, Bacteroides, Prevotella, Anaerobiospirillum, Fusobacterium,* and *Bilophila.* In some embodiments, the subject having an NK cell-responsive disorder can be in need of treatment for a bacterial infection from *Allochromatium vinosum, Acinetobacter baumanii, Bacillus anthracis, Campylobacter jejuni, Chlamydia trachomatis, Chlamydia pneumoniae, Clostridium* spp., *Citrobacter* spp., *Escherichia coli, Enterobacter* spp., *Enterococcus faecalis., Enterococcus faecium, Francisella tularensis, Haemophilus influenzae, Helicobacter pylori, Klebsiella* spp., *Listeria monocytogenes, Moraxella catarrhalis, Mycobacterium tuberculosis., Neisseria meningitidis, Neisseria gonorrhoeae, Proteus mirabilis, Proteus vulgaris, Pseudomonas aeruginosa, Salmonella* spp., *Serratia* spp., *Shigella* spp., *Streptococcus pneumoniae, Staphyloccocus aureus, Staphyloccocus epidermidis, Streptococcus pneumoniae, Streptococcus pyogenes, Streptococcus agalactiae, Yersina pestis,* and *Yersina enterocolitica,* or the like; or *Peptostreptococci asaccharolyticus, Peptostreptococci magnus, Peptostreptococci micros, Peptostreptococci prevotii, Porphyromonas asaccharolytica, Porphyromonas canoris, Porphyromonas gingivalis, Porphyromonas macaccae, Actinomyces israelii, Actinomyces odontolyticus, Clostridium innocuum, Clostridium clostridioforme, Clostridium difficile, Bacteroides tectum, Bacteroides ureolyticus, Bacteroides gracilis (Camaylobacter gracilis), Prevotella intermedia, Prevotella heparinolytica, Prevotella oris-buccae, Prevotella bivia, Prevotella melaminogenica, Fusobacterium naviforme, Fusobacterium necrophorum, Fusobacterium varium, Fusobacterium ulcerans, Fusobacterium russii, Bilophila wadsworthia, Haemophilus ducreyi; Calymmatobacterium granulomatis,* or the like.

Compounds or pharmaceutical compositions of the invention can be particularly useful for treating a subject with an intracellular infection. It is generally believed in the art that NK cells are particularly effective against intracellular infections. Intracellular infections are those wherein a portion of the infecting pathogen resides within cells of the subject.

For example, intracellular infections can be caused by one or more bacteria selected from: *Ehrlichia* (e.g., obligate, intracellular bacteria that can appear as small cytoplasmic inclusions in lymphocytes and neutrophils such as *Ehrlichia sennetsu, Ehrlichia canis, Ehrlichia chaffeensis, Ehrlichia phagocytophilia,* or the like); *Listeria* (e.g., *Listeria monocytogenes*), *Legionella* (e.g., *Legionella pneumophila*); *Rickettsiae* (e.g., *Rickettsiae prowazekii, Rickettsiae typhi (Rickettsiae mooseri), Rickettsiae rickettsii,Rickettsiae tsutsugamushi, Rickettsiae sibirica; Rickettsiae australis; Rickettsiae conorii; Rickettsiae akari; Rickettsiae burnetii*); *Chlamydia* (e.g., *Chlamydia psittaci; Chlamydia pneumoniae; Chlamydia trachomatis,* or the like); *Mycobacterium* (*Mycobacterium tuberculosis; Mycobacterium marinum; Mycobacterium Avium* Complex; *Mycobacterium bovis; Mycobacterium scrofulaceum; Mycobacterium ulcerans; Mycobacterium leprae* (*Leprosy*, Hansen's *Bacillus*)); *Brucella* (e.g., *Brucella melitensis; Brucella abortus; Brucella suis; Brucella canis*); genus *Coxiella* (e.g., *Coxiella burnetii*); or the like. Thus, in some embodiments, the subject can have an intracellular bacterial infection caused by a bacterium selected from the genera *Ehrlichia; Listeria; Legionella; Rickettsiae; Chlamydia; Mycobacterium; Brucella;* and *Coxiella.*

In various embodiments, the subject having an NK cell-responsive disorder can be in need of treatment for a bacterial infection from one or more upper respiratory tract bacteria. Examples of upper respiratory tract bacteria include those belonging genera such as *Legionella, Pseudomonas,* and the like. In some embodiments, the bacteria can be *Pseudomonas aeruginosa.* In particular embodiments, the bacteria can be *Legionella pneumophila* (e.g., including serogroups 1, 2, 3, 4, 5, 6, 7, 8, and the like), *Legionella dumoffli, Legionella longbeacheae, Legionella micdadei, Legionella oakridgensis, Legionella feelei, Legionella anisa, Legionella sainthelensi, Legionella bozemanii, Legionella gormanii, Legionella wadsworthii, Legionella jordanis,* or *Legionella gormanii.*

In some embodiments, the subject having an NK cell-responsive disorder can be in need of treatment for a bacterial infection from one that causes acute bacterial exacerbation of chronic bronchitis (ABECB) in the subject. Typically, ABECB can be caused by *Streptococcus pneumoniae, Haemophilia influenzae, Haemophilus parainfluenzae,* or *Moraxella catarrhalis.*

In some embodiments, the subject having NK cell-responsive disorder can be in need of treatment for a bacterial infection from one that causes acute community acquired pneumonia (CAP) in the subject. Typically, CAP can be caused by *Streptococcus pneumoniae, Haemophilus influenzae, Moraxella catarrhalis, Mycoplasma pneumoniae, Chlamydia pneumoniae,* or *Klebsiella pneumoniae.* In a particular embodiment, the CAP can be caused by drug resistant bacteria, e.g., a multi-drug resistant strain of *Streptococcus pneumoniae.*

In various embodiments, the subject having an NK cell-responsive disorder can be in need of treatment for a bacterial infection from *Streptococcus pneumoniae, Haemophilus* influenzae, Haemophilus parainfluenzae, Moraxella catarrhalis, Mycoplasma pneumoniae, Chlamydia pneumoniae, Klebsiella pneumoniae, Staphylococcus aureus, Streptococcus pyogenes, Acinetobacter Iwoffi, Klebsiella oxytoca, Legionella pneumophila, or Proteus vulgaris.

In various embodiments, the subject having an NK cell-responsive disorder can be in need of treatment for a bacterial infection from maxillary sinus pathogenic bacteria. As used herein, maxillary sinus pathogenic bacteria is a bacterial strain isolated from acute or chronic maxillary sinusitis, or, for example, a maxillary sinus isolate of *Staphylococcus aureus, Streptococcus pneumoniae, Haemophilus* spp., *Moraxella catarrhalis*, an anaerobic strain of non-fermentative Gram negative bacilli, *Neisseria meningitides* or β-haemolytic *Streptococcus*. In various embodiments, maxillary sinus pathogenic bacteria can include a bacterial strain isolated from acute or chronic maxillary sinusitis; a maxillary sinus isolate of *Staphylococcus aureus, Streptococcus pneumoniae, Haemophilus* spp., *Moraxella catarrhalis*, an anaerobic strain of non-fermentative Gram negative bacilli, *Neisseria meningitidis*β-haemolytic *Streptococcus, Haemophilus influenzae*, an *Enterobacteriaceae*, a non-fermentative Gram negative bacilli, *Streptococcus pneumoniae, Streptococcus pyogenes*, a methicillin-resistant *Staphylococcus* spp., *Legionella pneumophila, Mycoplasma* spp. and *Chlamydia* spp., *Haemophilus influenzae, Haemophilus parainfluenzae, Peptostreptococcus, Bacteroides* spp., and *Bacteroides* urealyticus.

In various embodiments, the subject having an NK cell-responsive disorder can be in need of treatment for a bacterial infection that causes a urinary tract infection (UTI) in the subject. Examples of UTIs include urethritis, cystitis, prostatitis, pyelonephritis (acute, chronic, and xanthogranulmnatous), and hematogenous UTI (e.g., from bacteremia with virulent bacilli such as *Salmonella, Staphylococcus aureus*, and the like). Typically, UTIs can be caused by gram-negative aerobic bacteria, e.g., *Escherichia* (e.g., *Escherichia coli*), *Klebsiella, Proteus, Enterobacter, Pseudomonas*, and *Serratia*; gram-negative anaerobic bacteria; gram-positive bacteria, e.g., *Enterococci* (e.g., *Enterococcus faecalis*) and *Staphylococcus* sp (e.g., *Staphylococcus saprophyticus, Staphylococcus aureus*, and the like); *Mycobacterium tuberculosis*; and sexually transmitted bacterial infections (e.g., *Chlamydia trachomatis, Neisseria gonorrhoeae*, and the like).

In certain embodiments, the subject having an NK cell-responsive disorder can be in need of treatment for infections from microorganisms that cause sexually transmitted diseases, for example, *Treponema pallidum; Trichomonas* vaginalis; Candidia (*Candida albicans*); *Neisseria gonorrhoeae; Chlamydia trachomatis; Mycoplasma genitalium, Ureaplasma urealyticum; Haemophilus ducreyi; Calymmatobacterium granulomatis* (formerly *Donovania granulomatis*); herpes simplex viruses (HSV-1 or HSV-2); human papillomavirus [HPV]; human immunodeficiency virus (HIV); various bacterial (*Shigella, Campylobacter*, or *Salmonella*), viral (hepatitis A), or parasitic (*Giardia* or amoeba, e.g., *Entamoeba dispar* (previously *Entamoeba histolytica*); or the like.

Thus, in various embodiments, the subject having an NK cell-responsive disorder can be in need of treatment for an infection resulting in upper respiratory tract bacterial infection, acute bacterial exacerbation of chronic bronchitis; acute community acquired pneumonia, maxillary sinus pathogenic bacteria; a urinary tract infection; or a sexually transmitted infection.

The compounds and pharmaceutical compositions of the present invention can be particularly effective for treating a subject with a viral infection. Thus, in various embodiments, a subject having an NK cell-responsive disorder can be in need of treatment for infection from viruses such as Picornaviruses (e.g., Polio Virus, rhinoviruses and certain echoviruses and coxsackieviruses); Parvoviridae (Human Parvovirus B19); Hepatitis, e.g., Hepadnavirus (Hepatitis B); Papovavirus (JC Virus); Adenovirus (Human Adenovirus); Herpesvirus Cytomegalovirus, Epstein Ban Virus (Mononucleosis), Mononucleosis-Like Syndrome, Roseola Infantum, Varicella Zoster Virus (Chicken Pox), Herpes Zoster (Shingles), Herpes Simplex Virus (Oral Herpes, Genital Herpes)), Poxvirus (Smallpox); Calicivirus (Norwalk Virus), Arbovirus (e.g., Togavirus (Rubella virus, Dengue virus), Flavivirus (Yellow Fever virus), Bunyavirus (California Encephalitis Virus), Reovirus (Rotavirus)); Coronavirus (Coronavirus); Retrovirus (Human Immunodeficiency Virus 1, Human Immunodeficiency Virus 2); Rhabdovirus (Rabies Virus), Filovirus (Marburg Virus, Ebola virus, other hemorrhagic viral diseases); Paramyxovirus (Measles Virus; Mumps Virus); Orthomyxovirus (Influenza Virus); Arenavirus (Lassa Fever); human T-cell Lymphotrophic virus type I and II (HTLV-I, HTLV II); human papillomavirus [HPV]; or the like. Thus, in various embodiments, the subject can have an infection caused by a virus selected from Picornavirus; Parvoviridae, Hepatitis virus; Papovavirus; Adenovirus; Herpesvirus, Poxvirus; Calicivirus; Arbovirus; Coronavirus; a Retrovirus; Rhabdovirus; Paramyxovirus; Orthomyxovirus; Arenavirus; human T-cell Lymphotrophic virus; human papillomavirus; and human immunodeficiency virus.

In some embodiments, a subject having an NK cell-responsive disorder can be in need of treatment for an infection from a virus or an infection thereof such as human immunodeficiency virus-1, human immunodeficiency virus-2, Cytomegalovirus, Epstein Ban Virus, Mononucleosis-Like Syndrome, Roseola Infantum, Varicella Zoster Virus, Herpes Zoster, Herpes Simplex Virus, or hepatitis.

It is believed that the methods can be particularly effective for treating a subject with a parasitic infection. Thus, in various embodiments, a subject having an NK cell-responsive disorder can be in need of treatment for an infection from *Plasmodia* (e.g., *Plasmodia falciparum, Plasmodia vivax, Plasmodia ovale*, and *Plasmodia malariae*, typically transmitted by anopheline mosquitoes); *Leishmania* (transmitted by sandflies and caused by obligate intracellular protozoa, e.g., *Leishmania donovani, Leishmania infantum, Leishmania chagasi, Leishmania mexicana, Leishmania amazonensis, Leishmania venezuelensis, Leishmania tropica; Leishmania major; Leishmania aethiopica*; and the subgenus *Viannia, Leishmania Viannia braziliensis, Leishmania Viannia guyanensis, Leishmania Viannia panamensis*, and *Leishmania Viannia peruviana*); *Trypanosoma* (e.g., sleeping sickness caused by *Trypanosoma brucei gambiense*, and *Trypanosoma brucei rhodesiense*); amoebas of the genera *Naegleria* or *Acanthamoeba*; pathogens such as genus *Entamoeba* (*Entamoeba histolytica* and *Entamoeba dispar*); *Giardia lamblia; Cryptosporidium; Isospora; Cyclospora; Microsporidia; Ascaris lumbricoides*; infection with blood flukes of the genus *Schistosoma* (e.g.; *S. haematobium; S. mansoni; S. japonicum; S. mekongi; S. intercalatum*); Toxoplasmosis (e.g., *Toxoplasma gondii*); *Treponema pallidum; Trichomonas* vaginalis; or the like.

In some embodiments, the subject having an NK cell-responsive disorder can have an infection caused by a protozoa selected from *Toxoplasma gondii, Trypcinosoma brucei gambiense, Trypanosoma brucei rhodesiense, Leishmania donovani, Leishmania infantum, Leishmania chagasi, Leishmania mexicana, Leishmania amazonensis, Leishmania venezuelensis, Leishmania tropica; Leishmania major; Leishmania aethiopica; and the subgenus Viannia, Leishmania Viannia braziliensis, Leishmania Viannia guyanensis, Leishmania Viannia panamensis, Leishmania Viannia peruviana, Plasmodia falciparum, Plasmodia vivax, Plasmodia ovale, and Plasmodia malariae.

In the last century, antibiotics were developed that led to significant reductions in mortality. Unfortunately, widespread use has led to the rise of antibiotic resistant bacteria, e.g., methicillin resistant *Staphyloccocus aureus*(MRSA), vancomycin resistant *enterococci* (VRE), and penicillin-resistant *Streptococcus pneumoniae* (PRSP). Some bacteria are resistant to a range of antibiotics, e.g., strains of *Mycobacterium tuberculosis* resist isoniazid, rifampin, ethambutol, streptomycin, ethionamide, kanamycin, and rifabutin. In addition to resistance, global travel has spread relatively unknown bacteria from isolated areas to new populations. Furthermore, there is the threat of bacteria as biological weapons. These bacteria may not be easily treated with existing antibiotics.

The compounds or the pharmaceutical compositions of the invention can be particularly effective for treating a subject for drug-resistant pathogens, for example, drug resistant bacteria, or pathogens for which no drugs are available, e.g., many viruses. Without wishing to be bound by theory, it is believed that because the compounds of the invention can act by increasing NK cell activity, and thus the NK cells can kill infective microorganisms or infected cells separately from any direct action of the compounds on the pathogen or infected cells. Thus, it is believed that the compounds of the invention can have at least one mode of action that is separate from typical anti-infective drugs such as antibiotics which can typically act directly on the bacteria themselves.

Drug resistant pathogens can be resistant to at least one and typically multiple agents, for example, drug resistant bacteria can be resistant to one antibiotic, or typically at least two antibiotics such as penicillin, Methicillin, second generation cephalosporins cefuroxime, and the like), macrolides, tetracyclines, trimethoprim/methoxazole, vancomycin, or the like. For example, in some embodiments, a subject can be treated for bacteria selected from a strain of multiple drug resistant *Streptococcus pneumoniae* (MDRSP, previously known as penicillin resistant *Streptococcus pneumoniae*, PRSP), vancomycin resistant *Enterococcus*, methicillin resistant *Staphylococcus Aureus*, penicillin resistant Pneumococcus, antibiotic resistant *Salmonella*, resistant and multi-resistant *Neisseria Gonorrhea* (e.g., resistant to one, two or more of tetracycline, penicillin, fluoroquinolones, cephalosporins, ceftriaxone (Rocephin), Cefixime (Suprax), Azithromycin, or the like), and resistant and multi-resistant Tuberculosis (e.g., resistant to one, two or more of Isoniazid, Rifampin, Ethambutol, Pyrazinamide, Aminoglycoside, Capreomycin, Ciprofloxacin, Ofloxacin, gemifloxacin, Cycloserine, Ethionamide, para-aminosalicylic acid or the like).

In some embodiments, NK cell activity can be increased in subjects that have an immunodeficiency. In various embodiments, this can be due to decreased or deficient NK cell activity. In some embodiments, the immunodeficiency can be any known immunodeficiency, even those that do not directly impact NK cells. Without wishing to be bound by theory, it is believed that boosting NK cell activity can augment immune function in many immunodeficiency conditions to "make-up" at least in part, for aspects of immunodeficiency separate from those aspects directly concerned with NK cell activity.

In various embodiments, immunodeficiency disorders can include disorders with increased susceptibility to infection, for example, one or more disorders selected from: circulatory and systemic disorders (sickle cell disease, diabetes mellitus, nephrosis, varicose veins, congenital cardiac defects); obstructive disorders (ureteral or urethral stenosis, bronchial asthma, bronchiectasis, allergic rhinitis, blocked Eustachian tubes); integumentary defects (eczema, burns, skull fractures, midline sinus tracts, ciliary abnormalities); primary immunodeficiencies (X-linked agammaglobulinemia, DiGeorge anomaly, chronic granulomatous disease, C3 deficiency); secondary immunodeficiencies (malnutrition, prematurity, lymphoma, splenectomy, uremia, immunosuppressive therapy, protein-losing enteropathy, chronic viral diseases); unusual microbiologic factors (antibiotic overgrowth, chronic infections with resistant organism, continuous reinfection (contaminated water supply, infectious contact, contaminated inhalation therapy equipment)); foreign bodies, trauma (ventricular shunts, central venous catheter, artificial heart valves, urinary catheter, aspirated foreign bodies) allogeneic transplant, graft-versus-host disease, uterine dysfunction (e.g., endometriosis), or the like.

In various embodiments, immunodeficiency disorders can include for example, transient hypogarnmaglobulinemia of infancy, selective IgA deficiency, X-linked agammaglobulinemian (Bruton's Agammaglobulinemia; Congenital Agammaglobulinemia), common variable immunodeficiency (Acquired Agammaglobulinemia), hyper-IgM immunodeficiency, IgG subclass deficiency, chronic mucocutaneous Candidiasis, combined immunodeficiency, Wiskott-Aldrich syndrome, ataxia-telangiectasia, X-linked lymphoproliferative syndrome, hyper-IgE syndrome (Job-Buckley Syndrome), chronic granulotomatous disease, leukocyte adhesion deficiency (MAC-1/LFA-1/CR3 deficiency), or the like.

In various embodiments, immunodeficiency disorders can include primary immunodeficiency disorders for example: B-cell (antibody) deficiencies (X-linked agammaglobulinemia; Ig deficiency with hyper-IgM (XL); IgA deficiency); IgG subclass deficiencies, Antibody deficiency with normal or elevated Igs, Immunodeficiency with theymoma, Common variable immunodeficiency, Transient hypogammaglobulinemia of infancy); T-cell (cellular) deficiencies (Predominant T-cell deficiency: DiGeorge anomaly, Chronic mucocutaneous candidiasis, Combined immunodeficiency with Igs (Nezelof syndrome), Nucleoside phosphorylase deficiency (AR), Natural killer cell deficiency, Idiopathic CD4 lymphocytopenia, Combined T- and B-cell deficiencies: Severe combined immunodeficiency (AR or XL), Adenosine deaminase deficiency (AR), Reticular dysgenesis, Bare lymphocyte syndrome, Ataxia-telangiectasia (AR), Wiskott-Aldrich syndrome (XL), Short-limbed dwarfism, XL lymphoproliferative syndrome); Phagocytic disorders (Defects of cell movement: Hyperimmunoglobulinemia E syndrome, Leukocyte adhesion defect type 1 (AR), Defects of microbicidal activity: Chronic granulomatous disease (XL or AR), Neutrophil G6PD deficiency, Myeloperoxidase deficiency (AR), Chediak-Higashi syndrome (AR)); Complement disorders (Defects of complement components: C1q deficiency, Defects of control proteins: C1 inhibitor deficiency (D1), Factor I (C3b inactivator) deficiency (ACD), Factor H deficiency (ACD) Factor D deficiency (ACD), Properdin deficiency (XL)); or the like.

In various embodiments, immunodeficiency disorders can include secondary immunodeficiency disorders, for example, one or more conditions selected from: Premature and newborn infants (Physiologic immunodeficiency due to immaturity of immune system); Hereditary and metabolic diseases (Chromosome abnormalities (e.g., Down syndrome), Uremia, Diabetes (i.e., complications from diabetes such as gangrene associated with peripheral circulatory and nerve dysfunction), Malnutrition, Vitamin and mineral deficiencies, Protein-losing enteropathies, Nephrotic syndrome, Myotonic dystrophy, Sickle cell disease); Immunosuppressive agents (Radiation, Immunosuppressive drugs, Corticosteroids, Anti-lymphocyte or anti-thymocyte globulin, Anti-T-cell monoclonal antibodies); Infectious diseases (Congenital rubella, Viral exanthems (e.g., measles, varicella), HIV infection, Cytomegalovirus infection, Infectious mononucleosis, Acute bacterial disease, Severe mycobacterial or fungal disease); Infiltrative and hematologic diseases (Histiocytosis, Sarcoidosis, Hodgkin's disease and lymphoma, Leukemia, Myeloma, Agranulocytosis and aplastic anemia); Surgery and trauma (Burns, Splenectomy, Anesthesia, wounds); and Miscellaneous (SLE, Chronic active hepatitis, Alcoholic cirrhosis, Aging, Anticonvulsive drugs, Graft-vs.-host disease); or the like.

In certain embodiments, the subject having an NK cell-responsive disorder can be in need of treatment for burns or wounds. Typically, such a wound or burn is a severe injury that places a significant burden on the subject's immune defenses. For example, in some embodiments, the subject is treated for a second or third degree burn covering at least about 5%, 10%, 15%, 20%, 25%, 30%, 40%, 50%, 75%, or more of the surface area of the subject's body. Also, in some embodiments, the subject is treated for a wound or wounds, e.g., an open wound of at least about 1 cm$^2$, 2 cm$^2$, 5 cm$^2$, 10 cm$^2$, 20 cm$^2$, 50 cm$^2$ or larger, or 1%, 2%, 3%, 4%, 5%, 10%, 15%, or more of the surface area of the subject's body; or one or more incisions penetrating the skin totaling at least 1 cm, 2 cm, 3 cm, 4 cm, 5 cm, 7 cm, 10 cm, 20 cm, 25 cm, 50 cm in length; an amputation; and the like.

In various embodiments, the subject having an NK cell-responsive disorder can have an infection caused by antibiotic resistant bacteria. In some embodiments, the subject can have an infection caused by a bacterium selected from multiple drug resistant *Streptococcus pneumoniae*, vancomycin resistant *Enterococcus*, methicillin resistant *Staphylococcus Aureus*, penicillin resistant Pneumococcus, antibiotic resistant *Salmonella*, resistant/multi-resistant *Neisseria Gonorrhea*, and resistant/multi-resistant Tuberculosis. In some embodiments, the subject can have a bacterial infection resistant to at least one antibiotic selected from penicillin, Methicillin, second generation cephalosporins, macrolides, tetracyclines, trimethoprim/methoxazole, vancomycin, tetracycline, fluoroquinolones, ceftriaxone, Cefixime, Azithromycin, Isoniazid, Rifampin, Ethambutol, Pyrazinamide, Aminoglycoside, Capreomycin, Ciprofloxacin, Ofloxacin, gemifloxacin, Cycloserine, Ethionamide, and para-aminosalicylic acid.

Thus, various embodiments, the subject having an NK cell responsive disorder can have an immunodeficiency disorder. In some embodiments, the subject can have a primary immunodeficiency disorder. In some embodiments, the subject can have a secondary immunodeficiency disorder.

In some embodiments, immunodeficiency disorders can include uremia, diabetes (infective complications thereof, malnutrition, vitamin and mineral deficiencies, protein-losing enteropathies, nephrotic syndrome, myotonic dystrophy, sickle cell disease; or the like.

In some embodiments, immunodeficiency disorders can be cause or be partially caused by immunosuppressive agents, e.g., radiation, immunosuppressive drugs, corticosteroids, anti-lymphocyte or anti-thymocyte globulin, anti-T-cell monoclonal antibodies; or the like.

In some embodiments, immunodeficiency disorders can caused or partially caused by surgery and trauma, e.g., burns, splenectomy, anesthesia, wounds, implanted medical devices; or the like.

In some embodiments, immunodeficiency disorders can include chronic fatigue syndrome (chronic fatigue immune dysfunction syndrome); Epstein-Barr virus infection, post viral fatigue syndrome, post-transplantation syndrome (host-graft disease), exposure to nitric oxide synthase inhibitors, aging, severe combined immunodeficiency, variable immunodeficiency syndrome, and the like.

Increasing NK cell activity would also be beneficial for treating subjects with disorders including, but not limited to a neurodegenerative disorder. As used herein, a neurodegenerative disorder involves degradation of neurons such as cerebral, spinal, and peripheral neurons (e.g., at neuromuscular junctions), more typically degradation of cerebral and spinal neurons. Neurodegenerative disorders can include Alzheimer's disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; epileptic seizure, injury-induced seizure, chemically-induced seizure, or other diseases associated with superoxide dismutase (SOD) mutations; and the like. Neurodegenerative disorders can also include degradation of neurons caused by ischemia, seizure, thermal stress, radiation, toxin exposure, infection, injury, and the like, Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively; tissues that can be damaged by ischemia include neurons, cardiac muscle, liver tissue, skeletal muscle, kidney tissue, pulmonary tissue, pancreatic tissue, and the like.

Other disorders in which increasing NK cell activity would be beneficial include disorders due to thermal stress, (thermal stress includes hyperthermia (e.g., from fever, heat stroke, burns, and the like) and hypothermia); radiation damage, e.g., due to visible light, ultraviolet light, microwaves, cosmic rays, alpha radiation, beta radiation, gamma radiation, X-rays, and the like, (for example, the damage could be radiation damage to non-cancerous tissue in a subject treated for cancer by radiation (therapy); mechanical injury, e.g., trauma from surgery, accidents, certain disease conditions (e.g., pressure damage in glaucoma) and the like; and exposure to a toxin, e.g., exposure to a neurotoxin selected from methamphetamine; antiretroviral HIV therapeutics (e.g., nucleoside reverse transcriptase inhibitors; heavy, metals (e.g., mercury, lead, arsenic, cadmium, compounds thereof and the like), amino acid analogs, chemical oxidants, ethanol, glutamate, metabolic inhibitors, antibiotics, and the like.

In some embodiments, the invention provides a method for treating or inhibiting angiogenesis in a subject in need thereof, comprising administering to the subject an effective amount of a compound as described herein. As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; *Mycobacteria* infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin discolorations (e.g., hemangioma, nevus flammeus, or nevus simplex); wound healing; hypertrophic scars, i.e., keloids; wound granulation; vascular adhesions; cat scratch disease (Rochele ninalia quintosa); ulcers (*Helicobacter pylori*); keratoconjunctivitis; gingivitis; periodontal disease; epulis; hepatitis; tonsillitis; obesity; rhinitis; laryngitis; tracheitis; bronchitis; bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease. Anti-angiogenesis can be demonstrated by any method known to those skilled in the art, such as the method described herein in Examples 10 and 11.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Suitable pharmaceutically acceptable carriers or diluents may contain inert ingredients which do not inhibit the biological activity of the compounds described herein. The pharmaceutically acceptable carriers or diluents should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, Mack Publishing Company, Easton, Pa. Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Flank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

An "effective amount" is the quantity of compound in which a beneficial clinical outcome is achieved when the compound is administered to a subject. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a an Hsp70-responsive disorder or an NK cell-responsive disorder, a "beneficial clinical outcome" includes reduction in the severity or number of symptoms associated with the disorder, elimination of an infection, or increase in the longevity of the subject compared with the absence of the treatment.

The precise amount of compound administered to a subject will depend on the type and severity of the disease or condition and on the characteristics of the subject, such as general health, age, sex, body weight and tolerance to drugs. It may also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. In some embodiments, effective amounts of the disclosed compounds include microgram to milligram amounts of the compound per kilogram of subject or sample weight (e.g., about 1 µg/kg to about 500 mg/kg, about 500 µg/kg to about 250 mg/kg, about 1 mg/kg to about 100 mg/kg, about 10 mg/kg to about 50 mg/kg, and the like). When co-administered with another anti-cancer agent for the treatment of cancer, an "effective amount" of the second anti-cancer agent will depend on the type of drug used. Suitable dosages are known for approved anti-cancer agents and can be adjusted by the skilled artisan according to the condition of the subject, the type of cancer being treated and the compound of the invention being used.

The compounds and pharmaceutical compositions disclosed herein is administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound and pharmaceutical composition disclosed herein can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

The present invention is illustrated by the following examples, which are not intended to be limiting in any way.

EXEMPLIFICATION

Example 1

Synthesis of the Compounds
Synthesis of Compound 1

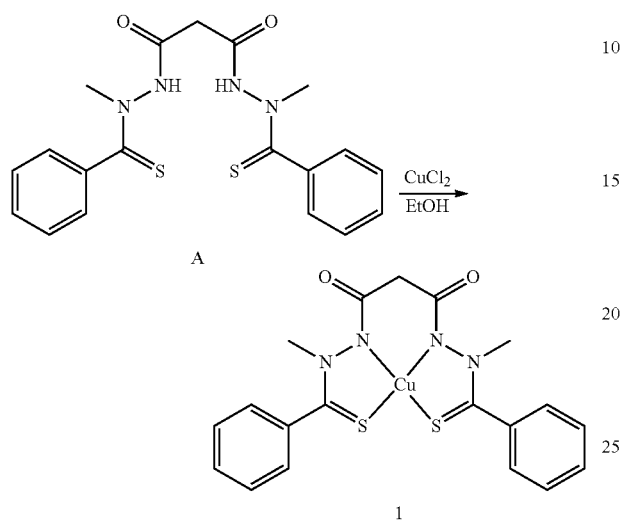

Into a solution of bis[thiohydrazide amide] A (800 mg, 2.0 mmol) in EtOH (10.0 mL) was added copper(II) chloride (277 mg, 2.0 mmol). The mixture was stirred at room temperature for 20 minutes. Water was added. The solid was collected by filtration. The solid was taken up in methylene chloride. The resulting solution was washed with water (2×), dried ($Na_2SO_4$), filtered and concentrated to give crude solid. The solid was washed with acetone to give the pure compound 1 (600 mg). Single crystal solid can be obtained by recrystallization from acetonitrile. MS (ESI) [M+H$^+$]: 462. MP: 198-202° C. (decomposed). Anal. calc. For $C_{19}H_{18}CuN_4O_2S_2$: C, 49.39; H, 3.93; N, 12.13. Found: C, 49.36; H, 3.68; N, 11.92.

Figure 26:
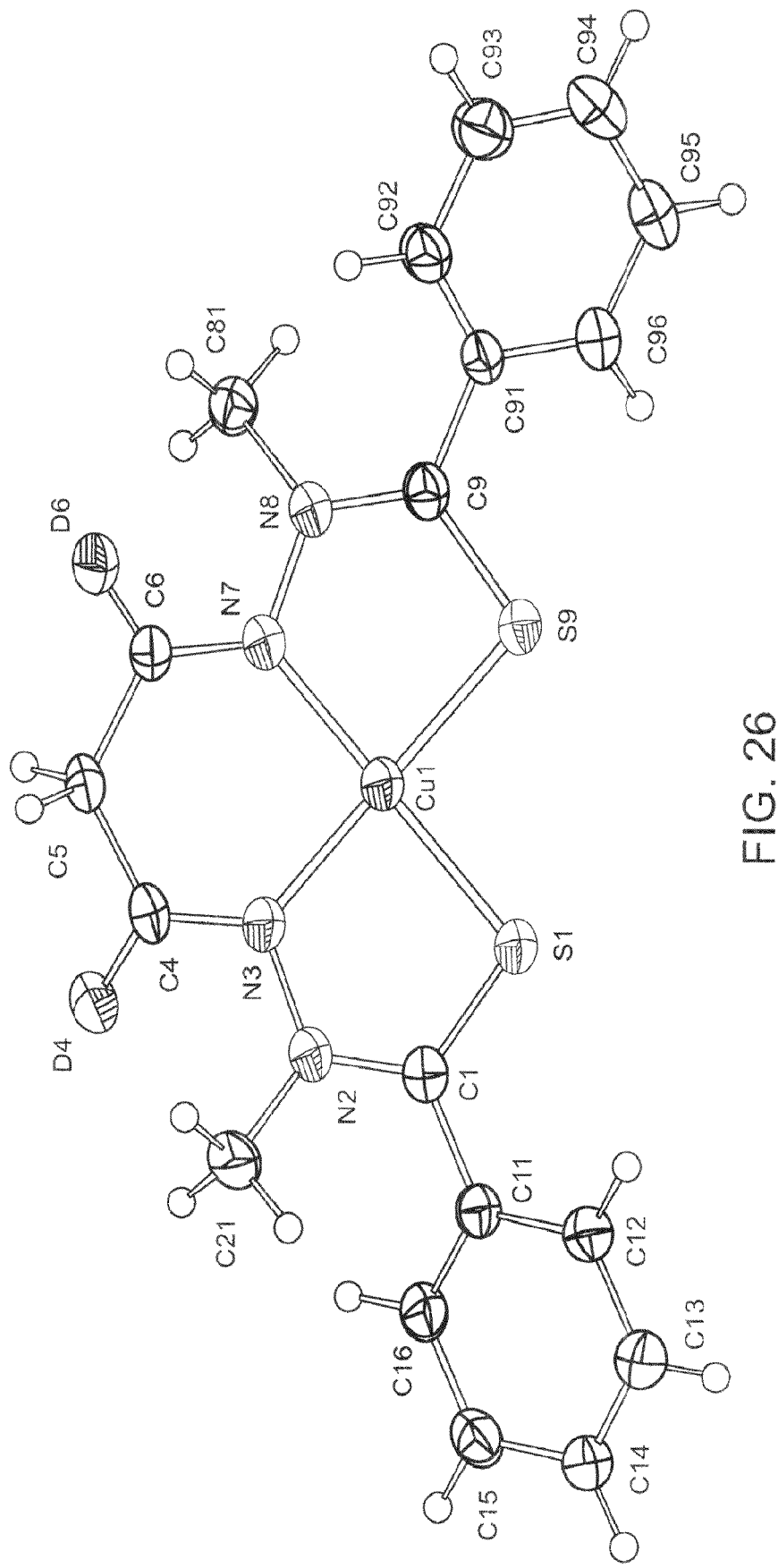
FIG. 26 is an ORTEP diagram of compound 1 showing 50% thermal ellipsoids.

FIG. 26 is an ORTEP diagram of compound 1 showing 50% thermal ellipsoids

Table of Bond Distances in Armstrongs for Compound 1

| Atom 1 | Atom 2 | Distance |
| --- | --- | --- |
| Cu1 | N7 | 1.944(2) |
| Cu1 | N3 | 1.948(2) |
| Cu1 | S1 | 2.2346(7) |
| Cu1 | S9 | 2.2375(7) |
| S1 | C1 | 1.694(3) |
| S9 | C9 | 1.707(3) |
| O4 | C4 | 1.231(3) |
| O6 | C6 | 1.227(3) |
| N2 | C1 | 1.321(3) |
| N2 | N3 | 1.405(3) |
| N2 | C21 | 1.482(3) |
| N3 | C4 | 1.370(3) |
| N7 | C6 | 1.363(3) |
| N7 | N8 | 1.414(3) |
| N8 | C9 | 1.316(3) |
| N8 | C81 | 1.481(3) |
| C1 | C11 | 1.479(4) |
| C4 | C5 | 1.510(4) |
| C5 | C6 | 1.519(4) |
| C5 | H51 | 0.94(4) |
| C5 | H52 | 1.01(3) |
| C9 | C91 | 1.481(4) |
| C11 | C12 | 1.392(3) |
| C11 | C16 | 1.394(3) |
| C12 | C13 | 1.383(4) |
| C12 | H12 | 0.950 |
| C13 | C14 | 1.389(4) |
| C13 | H13 | 0.950 |
| C14 | C15 | 1.389(4) |
| C14 | H14 | 0.950 |
| C15 | C16 | 1.384(4) |
| C15 | H15 | 0.950 |
| C16 | H16 | 0.950 |
| C21 | H21A | 0.980 |
| C21 | H21B | 0.980 |
| C21 | H21C | 0.980 |
| C81 | H81A | 0.980 |
| C81 | H81B | 0.980 |
| C81 | H81C | 0.980 |
| C91 | C92 | 1.391(4) |
| C91 | C96 | 1.403(3) |
| C92 | C93 | 1.388(4) |
| C92 | H92 | 0.950 |
| C93 | C94 | 1.382(4) |
| C93 | H93 | 0.950 |
| C94 | C95 | 1.393(4) |
| C94 | H94 | 0.950 |
| C95 | C96 | 1.384(4) |
| C95 | H95 | 0.950 |
| C96 | H96 | 0.950 |

Numbers in parentheses are estimated standard deviations in the least significant digits.

Table of Bond Angles in Degrees for Compound 1

| Atom 1 | Atom 2 | Atom 3 | Angle | Atom 1 | Atom 2 | Atom 3 | Angle |
| --- | --- | --- | --- | --- | --- | --- | --- |
| N7 | Cu1 | N3 | 96.27(8) | C11 | C12 | H12 | 120.20 |
| N7 | Cu1 | S1 | 161.69(6) | C12 | C13 | C14 | 120.7(3) |
| N3 | Cu1 | S1 | 86.92(6) | C12 | C13 | H13 | 119.60 |
| N7 | Cu1 | S9 | 86.58(6) | C14 | C13 | H13 | 119.60 |
| N3 | Cu1 | S9 | 158.38(6) | C13 | C14 | C15 | 119.6(3) |
| S1 | Cu1 | S9 | 97.10(3) | C13 | C14 | H14 | 120.20 |
| C1 | S1 | Cu1 | 96.53(9) | C15 | C14 | H14 | 120.20 |
| C9 | S9 | Cu1 | 96.97(9) | C16 | C15 | C14 | 119.9(2) |
| C1 | N2 | N3 | 118.7(2) | C16 | C15 | H15 | 120.00 |
| C1 | N2 | C21 | 122.7(2) | C14 | C15 | H15 | 120.00 |
| N3 | N2 | C21 | 116.67(19) | C15 | C16 | C11 | 120.4(2) |
| C4 | N3 | N2 | 112.6(2) | C15 | C16 | H16 | 119.80 |
| C4 | N3 | Cu1 | 118.96(18) | C11 | C16 | H16 | 119.80 |
| N2 | N3 | Cu1 | 115.96(14) | N2 | C21 | H21A | 109.50 |
| C6 | N7 | N8 | 113.3(2) | N2 | C21 | H21B | 109.50 |
| C6 | N7 | Cu1 | 120.48(17) | H21A | C21 | H21B | 109.50 |
| N8 | N7 | Cu1 | 116.52(14) | N2 | C21 | H21C | 109.50 |
| C9 | N8 | C81 | 118.6(2) | H21A | C21 | H21C | 109.50 |
| C9 | N8 | C81 | 123.2(2) | H21B | C21 | H21C | 109.50 |
| N7 | N8 | C81 | 115.93(19) | N8 | C81 | H81A | 109.50 |
| N2 | C1 | C11 | 120.7(2) | N8 | C81 | H81B | 109.50 |
| N2 | C1 | S1 | 121.3(2) | H81A | C81 | H81B | 109.50 |
| C11 | C1 | S1 | 118.07(17) | N8 | C81 | H81C | 109.50 |
| O4 | C4 | N3 | 125.2(2) | H81A | C81 | H81C | 109.50 |
| O4 | C4 | C5 | 119.7(2) | H81B | C81 | H81C | 109.50 |
| N3 | C4 | C5 | 114.9(2) | C92 | C91 | C96 | 119.1(2) |
| C4 | C5 | C6 | 124.5(2) | C92 | C91 | C9 | 121.6(2) |
| C4 | C5 | H51 | 111(2) | C96 | C91 | C9 | 119.1(2) |
| C6 | C5 | H51 | 106(2) | C93 | C92 | C91 | 120.6(2) |
| C4 | C5 | H52 | 101.6(19) | C91 | C92 | H92 | 119.70 |
| C6 | C5 | H52 | 111.1(19) | C93 | C92 | H92 | 119.70 |
| H51 | C5 | H52 | 99(3) | C94 | C93 | C92 | 120.1(3) |
| O6 | C6 | N7 | 125.4(2) | C94 | C93 | H93 | 119.90 |
| O6 | C6 | C5 | 118.8(2) | C92 | C93 | H93 | 119.90 |

-continued

Table of Bond Angles in Degrees for Compound 1

| Atom 1 | Atom 2 | Atom 3 | Angle | Atom 1 | Atom 2 | Atom 3 | Angle |
|---|---|---|---|---|---|---|---|
| N7 | C6 | C5 | 115.6(2) | C93 | C94 | C95 | 119.8(3) |
| N8 | C9 | C91 | 121.6(2) | C93 | C94 | H94 | 120.10 |
| N8 | C9 | S9 | 120.7(2) | C95 | C94 | H94 | 120.10 |
| C91 | C9 | S9 | 117.68(18) | C96 | C95 | C94 | 120.5(2) |
| C12 | C11 | C16 | 119.6(2) | C96 | C95 | H95 | 119.80 |
| C12 | C11 | C1 | 119.8(2) | C94 | C95 | H95 | 119.80 |
| C16 | C11 | C1 | 120.5(2) | C95 | C96 | C91 | 119.9(3) |
| C13 | C12 | C11 | 119.7(2) | C95 | C96 | H96 | 120.00 |
| C13 | C12 | H12 | 120.20 | C91 | C96 | H96 | 120.00 |

Numbers in parentheses are estimated standard deviations in the least significant digits.

Synthesis of Compound 2

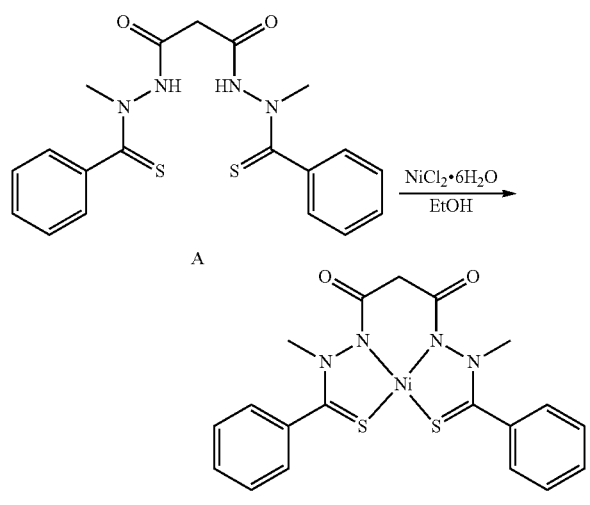

Compound 2 was prepared similarly as described for the preparation of compounds 1 using bis[thiohydrazide amide] A and nickel(II) chloride hexahydrate. MS (ESI) [M+H$^+$]: 457

$^1$H NMR (300 MHz, CDCl$_3$) δ7.58-7.44 (m, 10H), 3.61 (s, 6H) 3.59 (s, 2H).

Synthesis of Compound 3

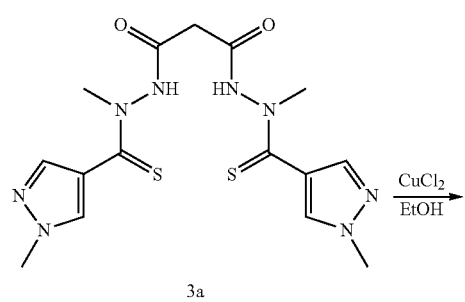

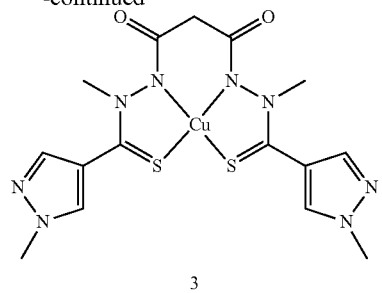

Compound 3 was prepared similarly as described for the preparation of compounds 1 using compound 3a. MS (ESI) [M+H$^+$]: 470

Synthesis of Compound 4

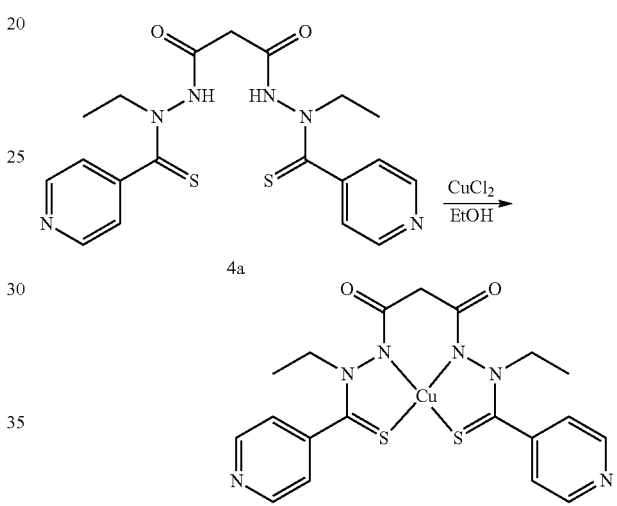

Compound 4 was prepared similarly as described for the preparation of compounds 1 using compound 4a. MS (ESI) [M+H$^+$]: 492

Synthesis of Compound 5

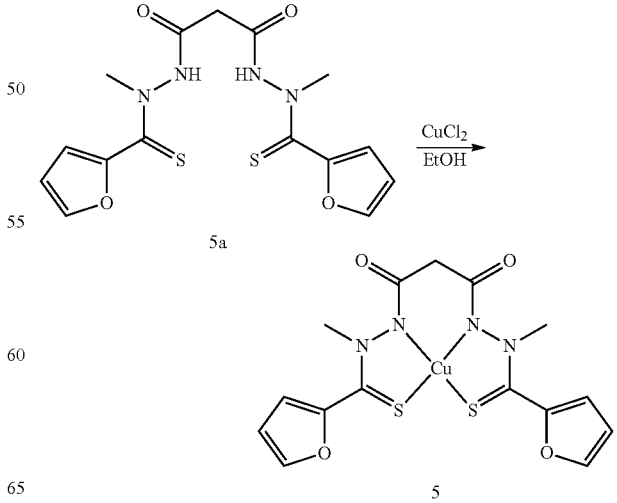

Compound 5 was prepared similarly as described for the preparation of compounds 1 using compound 5a. MS (ESI) [M+H⁺]: 442

Synthesis of Compound 6

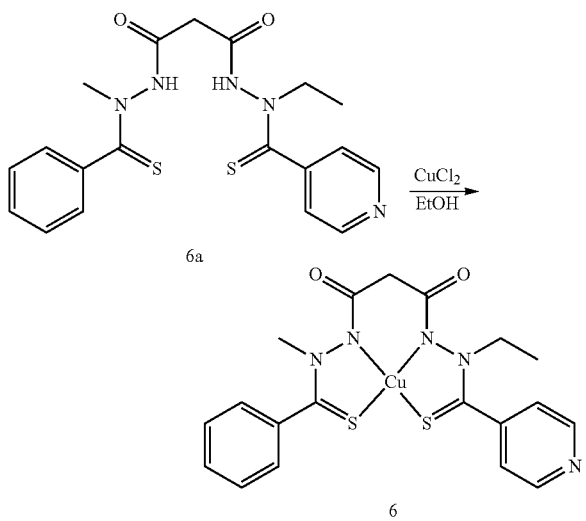

6a

6

Compound 6 was prepared similarly as described for the preparation of compounds 1 using compound 6a. MS (ESI) [M+H⁺]: 477

Synthesis of Compound 7

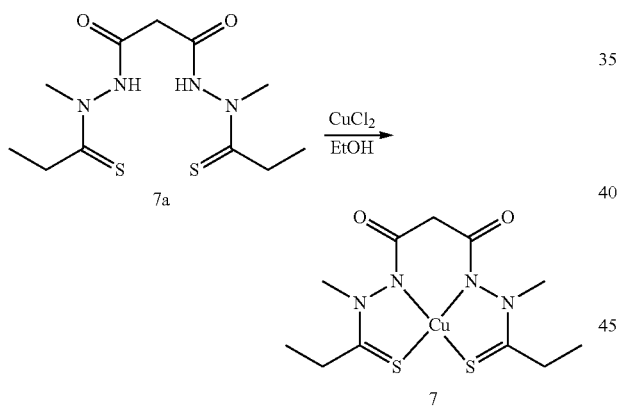

7a

7

Compound 7 was prepared similarly as described for the preparation of compounds 1 using compound 7a. MS (ESI) [M+H⁺]: 366

Example 2

Biological Activity of Compounds of the Invention

Figure 25:
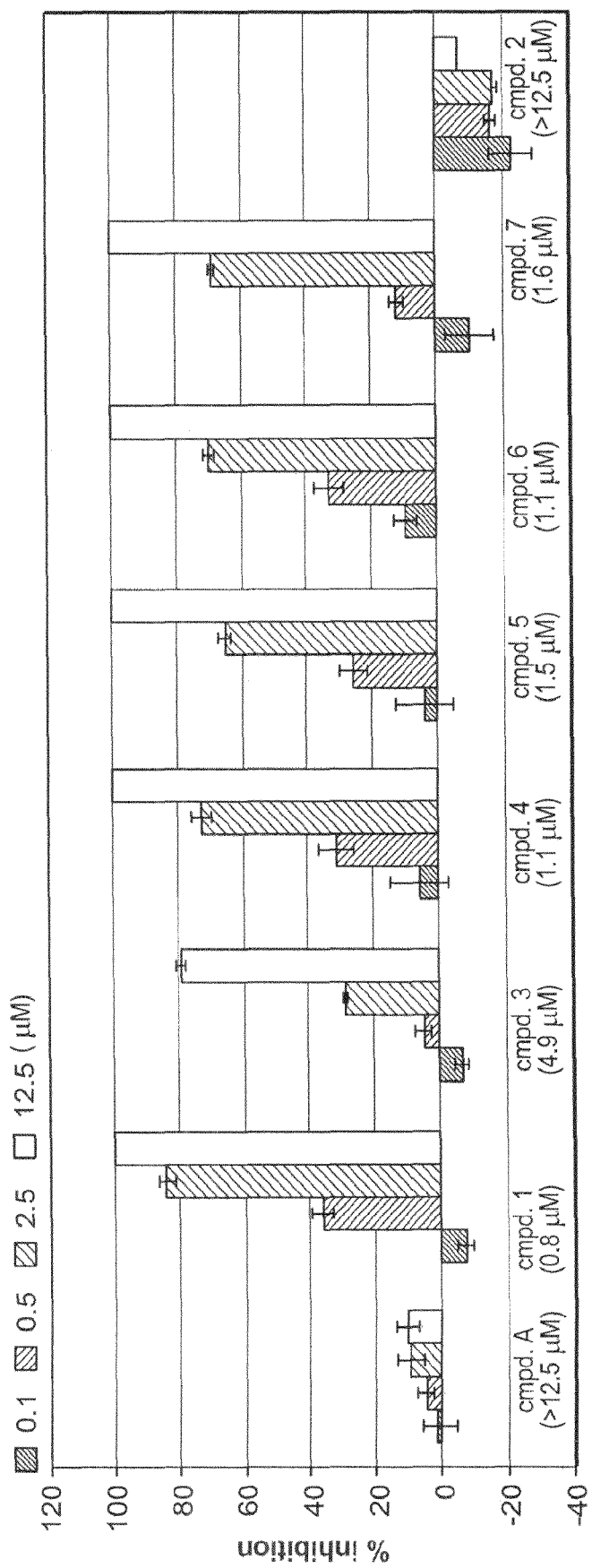
FIG. 25 shows the cytotoxicity of compounds of the invention in confluent M14 cells.

M14 melanoma cells were seeded at 50,000 cells per well of 96-well plate in 100 μl of Dulbecco's minimum essential medium (DMEM) supplemented with 10% fetal bovine serum. Cells were cultured at 37° C. under 5% $CO_2$-95% air. After 16 hours of incubation, the test compound was added to the cell culture. The compound was first diluted in 100% dimethyl sulfoxide (DMSO) at 400-fold of final concentrations actually used in the assay. The DMSO solution was next diluted 20 fold with the culture medium, and then finally added to the assay wells at another 20-fold dilution. The assay medium included the test compound with concentrations as indicated with 0.25% DMSO. Cell viability was measured with a CCK8 assay (as described in the Technical Manual for Cell Counting Kit-8, Product #CK04-11, CK04-13 and CK04-20, Dojindo Molecular Technologies, Inc. MD; Tantular, I. S. et al. Tropical Medicine and International Health, 8(6), 569-574, 2003) in the last 15 min after a 48 h incubation with the test compound. The data for compounds 1-7 are compared with that of compound A, shown in FIG. 25. Each bar of the figure expresses average percent inhibition against vehicle (0.25% DMSO) control (n=4). Error bars indicate standard deviation. The $IC_{50}$ values for compounds 1-7 are listed in Table 1.

| Compound | $IC_{50}$ (μM) |
|---|---|
| A | >12.5 |
| 1 | 0.8 |
| 2 | >12.5 |
| 3 | 4.9 |
| 4 | 1.1 |
| 5 | 1.5 |
| 6 | 1.1 |
| 7 | 1.6 |

Examples 3-7

Heat shock proteins (Hsp) are induced under a variety of stress conditions and bind to other proteins to prevent their denaturation. Hsps can protect the cell from apoptotic death. Agents that induce the production of Hsp70 can have protective activity against a wide range of insults, and may have particular utility in neurological disorders. The neuroprotectant activity of Hsp70 inducing compounds of the invention can be assessed in a variety of animal neurological disease models. Specifically, animal models of stroke, amyotrophic lateral sclerosis, Huntington's disease, Parkinson's disease, and Alzheimer's disease are appropriate settings for testing efficacy. Some example animal models are provided below.

Example 3

Cerebral Ischemia (Stroke)

The benefit of the disclosed treatment with Hsp70 inducing compounds of the invention can be assessed in rodent models of stroke. For example the stroke model described in Longa, et al. (Longa, E. Z., Weinstein, P. R., Carlson, S., and Cummins, R. (1989) Reversible middle cerebral artery occlusion without craniectomy in rats. Stroke 20:84-91) can be utilized.

Rats are anesthetized with ketamine, and then infarction is induced by extracranial vascular occlusion. A 4-0 nylon intraluminal suture is placed into the cervical internal carotid artery and is advanced intracranially to block blood flow into the middle cerebral artery. Collateral blood flow is reduced by interrupting all branches of the external carotid artery and all extracranial branches of the internal carotid artery. A compounds of the invention can be dosed just prior to or just after induction of the infarction. The dose may be, for example, 10 to 100 mg/kg body weight administered once per week, three times per week, or daily by any conventional mode of administration, e.g., orally or intravenously. Neurologic deficit, mortality, gross pathology (infarction size), and histochemical staining can be analyzed to assess efficacy of the compounds. Since this is a very acute model, and death is often observed by three days after infarction, the modeling may consist of only a single administration of drug.

Example 4

Familial Amyotrophi Lateral Sclerosis (ALS)

The efficacy of compounds of the invention in the treatment of ALS can be modeled using the SOD1 transgenic mouse model (Gurney, M. E., Pu, Chiu, A. Y., Dal Canto, M. C., Polchow, C. Y., Alexander, D. D., Caliendo, J., Hentati, A., Kwon, Y. W., and Deng, H. X. (1994) Motor neuron degeneration in mice that express a human CuZn superoxide dismutase mutation. *Science* 264:1772-1775). Mutations of human CuZn superoxide dismutase (SOD) are found in patients with familial ALS. Expression of the human SOD gene containing a substitution of glycine-to-alanine at amino acid 93 leads to motor neuron disease in transgenic mice. As a result of motor neuron loss from the spinal cord, the mice became paralyzed and die by 5 to 6 months of age.

To test the efficacy of the Hsp70 inducing compounds of the invention, transgenic mice having the SOD1 mutation (SOD1$^{G93A}$) are treated with the compounds, and the effect on disease is monitored. The symptoms are clinically apparent in these animals at 2.5 to 3 months of age. Compounds can be dosed starting at this time. The dose may be, for example, 10 to 100 mg/kg body weight administered once per week or three times per week by the oral or intravenous route. Endpoints include functional impairment of motor function as well as histological changes. The latter endpoints include histopathology of brain and spinal cord assessing degeneration of motor neurons and the appearance of neurofilament-rich inclusions in spinal motor neurons. If long-term administration is performed, the impact on mouse survival can be assessed.

Example 5

Huntington's Disease (HD)

A transgenic mouse model of HD exists, allowing the testing of Hsp70 inducing compounds of the invention for efficacy in this disease setting (Mangiarini, L., Sathasivam, K., Seller, M., Cozens, B., Harper, A., Hetherington, C., Lawton, M., Trottier, Y., Lehrach, H., Davies, S. W., and Bates, G. P. (1996) Exon 1 of the HD gene with an expanded CAG repeat is sufficient to cause a progressive neurological phenotype in transgenic mice. *Cell* 87:493-506; Carter, R. J., Lione, L. A., Humby, Mangiarini, L., Mahal, A., Bates, G. P., Dunnett, S. B., and Morton, A. J. (1999) Characterization of progressive motor deficits in mice transgenic for the human Huntington's disease mutation. *J. Neuroscience* 19:3248-3257). HD is caused by a CAG/polyglutamine repeat expansion. These transgenic mice (R6/2 transgenics) have the 5' end of the human HD gene with (CAG)115-(CAG)150 repeat expansions. The mice exhibit progressive neurological pathologies similar to HD, including abnormal and involuntary movements, tremors, and epileptic seizures.

These transgenic mice show overt behavioral changes at approximately 8 weeks of age. As early as 5 to 6 weeks of age, they display more subtle deficiencies in motor skills. Hsp70-inducing compounds of the invention can be administered by intravenous or oral administration at doses of 10-100 mg per kg of body weight starting at various times (for example, at 5 to 6 weeks of age). Compounds can be given on multiple different dosing schedules (e.g., once per week versus three times per week). Performance on one or more rodent motor tests such as swimming tank, beam walking, rotarod apparatus, and footprint test (see Carter, et al., 1999) can be performed to assess the activity of the compounds in preventing loss of neurological function in HD mice.

Example 6

Parkinson's Disease (PD)

There are two widely employed models of PD in which disease is induced by chemical treatment. These are the 6-OHDA (Zigmond, M. J. and Stricker, E. M. (1984) Parkinson's disease: studies with an animal model. *Life Sci.* 35:5-18; Sauer, H. and Oertel, W. H. (1994) Progressive degeneration of nigrostriatal dopamine neurons following intrastriatal terminal lesions with 6-hydroxydopamine: a combined retrograde tracing and in immunocytochemical study in the rat. *Neuroscience* 59:401-415) and the MPTP (Langston, J. W., Forno, L. S., Rebert, C. S., and Irwin, I. (1984) Selective nigral toxicity after systemic administration of 1-methyl-4-phenyl-1,2,5,6-tetrahydropyrine (MPTP) in the squirrel monkey. *Brain Res.* 292:390-4) models. An example of a test of Hsp70 inducing compounds of the invention using the 6-OHDA is described.

Young adult male rats are injected with Fluoro-Gold (FG) by stereotactic injection into the striatum in the brain in order to facilitate visualization of the neurons in the substantia nigra, the site of PD. Under anesthesia, 0.2 μl of a 4% solution of FG is administered by stereotactic injection (1 mm anterior from bregma, 3 mm lateral, and 4.5 mm ventral from dura into both striata). One week after FG injection, the rats receive a stereotactic injection of 6-OHDA (20 μg dissolved in 4 μl saline; Sigma) into the striatum on one side of the brain, at the same coordinates as the FG injection. Hsp70 inducing compounds of the invention can be administered by intravenous or oral administration at doses of 10-100 mg per kg of body weight. The compounds can be given at the time of 6-OHDA injection or some time (2-4 weeks, for example) subsequent to 6-OHDA treatment. Rats are sacrificed 8 and 16 weeks after 6-OHDA injection. The endpoints of this model are 1) behavioral changes as monitored in-life at various times by assessment of turning (rotational) behavior using classical neurological read-out, and 2) the brain is removed after sacrifice, thin sections are made using a cryostat, and immunohistochemistry is performed as described in Zigmond and Stricker (1984). Efficacy of the Hsp70 inducing compounds of the invention is demonstrated by a decrease in rotational behavior as well as a reduction in the loss of nigral dopaminergic neurons.

Example 7

Alzheimer's Disease (AD)

There are several transgenic mouse models of AD. One such model that is widely used to test the efficacy of drugs in AD was described by Holcomb, et al. (Holcomb, L., Gordon, M. N., McGowan, E., Yu, X., Benkovic, S., Jantzen, P., Wright, K., Saad, I., Mueller, R., Morgan, D., Sanders, S., Zehr, O'Campo, Hardy, J., Prada, C. M., Eckman, C., Younkin, S., Hsiao, K., and Duff, K. (1998) Accelerated Alzheimer-type phenotype in transgenic mice carrying both mutant amyloid precursor protein and presenilin 1 transgenes. *Nature Medicine* 4:97-100). This model contains two different genes associated with AD. One is a mutation in the amyloid precursor protein (APP), The mutant APP (K670N, M671L) transgenic line, Tg2576, has elevated amyloid beta-protein levels at an early age, and, later, develops extracellular AD-type A beta deposits in the brain. The other gene is a mutated presenilin-1 (PS1) gene. The doubly transgenic progeny from across between Tg2576 and the PS1 mutant PS1M146L, transgenic line develop large numbers of fibrillar A beta deposits in cerebral cortex and hippocampus far earlier than their singly transgenic Tg2576 mice.

Hsp70 inducing compounds of the invention can be dosed in mice at various times. The age of mice at the start of drug dosing may be varied. For example, a treatment starting time may be at 3 months of age, a time at which the brain deposits are first detectable. The dose may be, for example, 10 to 100 mg/kg body weight administered once per week or three times per week by the oral or intravenous route. The effect of drug treatment can be assessed by measuring AD-type deposits in the brain as well as by assessing function of the mice in a maze test.

Example 8

Measurement of Heat Shock Protein 70 (Hsp70)

Plasma Hsp70 can be measured by a sandwich ELISA kit (Stressgen Bioreagents Victoria, British Columbia, CANADA) according to a modified protocol in house. In brief, Hsp70 in plasma specimens and serial concentrations of Hsp70 standard are captured onto 96-well plate on which anti-Hsp70 antibody was coated. Then captured Hsp70 is detected with a biotinylated anti-Hsp70 antibody followed by incubation with europium-conjugated streptavidin. After each incubation unbound materials are removed by washing. Finally, antibody-Hsp70 complex was measured by time resolved fluorometry of europium. Concentration of Hsp70 is calculated from a standard curve.

Example 9

Measurement of Natural Killer Cell Cytotoxic Activity

The following procedure can be employed to assay NK cell activity in a subject. The procedure is adapted from Kantakamalakul W, Jaroenpool J, Pattanapanyasat K. A novel enhanced green fluorescent protein (EGFP)-K562 flow cytometric method for measuring natural killer (NK) cell cytotoxic activity. *J Immunol Methods*, 2003 Jan. 15; 272:189-197, the entire teachings of which are incorporated herein by reference.

Materials and methods: Human erythroleukaemic cell line, K562, is obtained from American Type Culture Collection (CCL-243, American Type Culture Collection, Manassas, Va.), and cultured in RPMI-1640 medium (Cat #11875-093 Gibco Invitrogen Corp, Carlsbad, Calif.) supplemented with 10% heat inactivated fetal calf serum (Gibco), 2 mM L-glutamin, 100 µg/ml streptomycin and 100 IU/ml penicillin at 37° C. with 5% $CO_2$. K562 cells are transduced with retroviral vector which encode green fluorescent protein (eGFP). Stable cell line is selected with antibiotic, G418. About 99.6% G418 resistant cells are eGFP positive after section.

The subject's peripheral blood mononuclear cells (PBMCs) are prepared by clinical study sites and received in BD Vacutainer Cell Preparation Tube with sodium heparin (Product Number: 362753, Becton Dickinson, Franklin Lakes, N.J.).

Two-fold serial dilution of 800 µl effector cells (patient's PBMC) starting at concentration of $1 \times 10^6$ cells/mL are put into four individual polystyrene 12×75-mm tubes. Log phase growing target cells (K562/eGFP) are adjusted with growth medium (RPMI-1640) to a concentration of $1 \times 10^5$ cells/mL and 100 µl targets then added into the tubes to provide effector/target (E/T) ratios of 80:1, 40:1, 20:1, 10:1. Effector cells alone and target cells alone are used as controls. All tubes are incubated at 37° C. with 5% $CO_2$ for about 3.5 hr. Ten microliters of propidium iodide (PI) at a concentration of 1 mg/mL is added to each tube including effector and target control tubes and then incubated at room temperature for 15 min.

Cytotoxic activity is analyzed with a FACSCalibur flow cytometer (Becton Dickinson). Linear amplification of the forward and side scatter (FSC/SSC) signals, as well as logarithmic amplification of eGFP and PI emission in green and red fluorescence is obtained. Ten thousand events per sample tube with no gating for acquisition are collected for analysis. Data analysis for two-parameter dot plots for eGFP versus PI is performed using CELLQuest (Becton Dickinson Biosciences) software to enumerate live and dead target cells. Debris and dead cells are excluded by setting a threshold of forward light scatter.

Example 10

Inhibition of HUVEC cell migration

To examine if the compounds of the invention affect endothelial cell function, an in vitro human umbilical vein endothelial cell (HUVEC) migration assay is performed in the presence of a compound of the invention. HUVEC cells (passage number 4) are cultured on 12-well plates and time-lapse imaging is performed with the live cell imaging system on an inverted microscope supplied with 6-7% $CO_2$. The temperature is kept at 37° C. Images are taken every 30 minutes using the 2× objective for up to 106 hr or every 60 seconds using the 20× objective for 30 min. Confluent HUVEC cultures are scraped similarly to make a blank area, followed by culturing in HUVEC medium for 15 hr without treatment. The migration areas, which are imaged as time-lapse sequences for each well, are used as a basis to standardize/correct migration rates. Then, migration of cells under different treatments is imaged at the same time to generate time-lapse image sequences for each well. Time-lapse movies are further analyzed by measuring areas that are covered by migrating cells. During experiments, HUVEC cells are activated by the presence of VEGF and basic FGF. Compounds of the invention (e.g. 100 nM and 1 µM) are expected to completely block migration of HUVEC cells to the blank area, indicating that compounds of the invention possesses potent inhibitory effect on the migration of activated HUVEC cell in vitro induced by VEGF and basic FGF.

It is also possible to track HUVEC behavior during above treatments. It is expected that HUVEC cells will begin to shrink after 24 hr treatment with compounds of the invention.

Example 11

Enhanced VE-cadherin junctions of HUVEC cells

An immunofluorescence study is performed by using anti-VE-cadherin antibodies to examine VE-cadherin junctions between HUVEC cells. HUVEC cells are treated with DMSO or a compound of the invention (e.g. 10, 100 and 1000 nM) for 24 hrs and fixed for immunostaining, DMSO concentration is 1:100 for all treatments. To boost the immunofluorescence signal, cells are stained with a mixture of 2 polyclonal anti-human VE-cadherin Abs followed by staining with a mixture of fluorescent secondary antibodies. It is expected that with compounds of the invention, VE-cadherin staining will be extremely strong in cell-cell junction regions, but not the non-contacted regions compared to that in DMSO treated cultures. Compounds of the invention are expected to enhance the assembly of cell-cell junctions of activated human endothelial cells, likely through induction of the accumulation of VE-cadherin molecules at the junctions. This effect could result in limited motility of the cells and reducing permeability of the endothelium, thus contributing to the cell migration inhibition and the potential anti-angiogenesis effect of compounds of the invention.

While this invention has been particularly shown and described with references to example embodiments thereof, it will be understood by those skilled in the art that various changes in form and details may be made therein without departing from the scope of the invention encompassed by the appended claims.

What is claimed is:

1. A compound comprising a bis[thiohydrazide amide] or a deprotonated form thereof complexed to a transition metal cation, wherein the bis[thiohydrazide amide] is represented by the following Structural Formula:

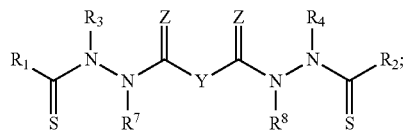

wherein:

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aryl group; and Y is a covalent bond of a substituted or unsubstituted straight chained hydrocarbyl group, or Y, taken together with both >C=Z groups to which it is bonded, is a substituted or unsubstituted aryl group;

$R_7$ and $R_8$ are independently —H, an optionally substituted aliphatic group, or an optionally substituted aryl group; and each Z is independently O or S.

2. The compound of claim 1, wherein the compound is greater than 90% pure by weight.

3. The compound of claim 1, wherein the transition metal cation is $Ni^{2+}$, $Cu^{2+}$, $Co^{2+}$, $Fe^{2+}$, $Pt^{2+}$ or $Pd^{2+}$.

4. The compound of claim 3, wherein the transition metal cation is $Cu^{2+}$.

5. The compound of claim 1, wherein the molar ratio of bis[thiohydrazide amide] or deprotonated form thereof to transition metal cation is equal to or greater than 0.5 and equal to or less than 2.0.

6. The compound of claim 1, wherein the molar ratio of bis[thiohydrazide amide] or deprotonated form thereof to transition metal cation is 1:1.

7. The compound of claim 1, wherein the compound is represented by the following Structural Formula:

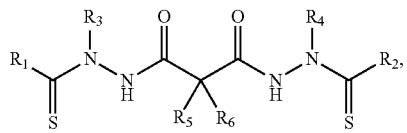

wherein $R_5$ and $R_6$ are each independently —H, an aliphatic or substituted aliphatic group, or $R_5$ is —H and $R_6$ is optionally substituted aryl group, or $R_5$ and $R_6$, taken together, are an optionally substituted $C_2$-$C_6$ alkylene group.

8. The compound of claim 7, wherein:

$R_1$ and $R_2$ are each an optionally substituted phenyl group;

$R_3$ and $R_4$ are each an optionally substituted alkyl group; and $R_5$ is —H and $R_6$ is —H, an alkyl or substituted alkyl group.

9. The compound of claim 7, wherein:

$R_1$ and $R_2$ are each an optionally substituted aliphatic group; and $R_3$ and $R_4$ are each an optionally substituted aliphatic group.

10. The compound of claim 9, wherein:

$R_1$ and $R_2$ are both a $C_3$-$C_8$ cycloalkyl group optionally substituted with at least one alkyl group;

$R_3$ and $R_4$ are each an optionally substituted alkyl group; and $R_5$ is —H and $R_6$ is —H, an alkyl or substituted alkyl group.

11. The compound of claim 10, wherein $R_1$ and $R_2$ are both cyclopropyl or 1-methylcyclopropyl.

12. The compound of claim 1, wherein the bis[thiohydrazide amide] is represented by a structural formula selected from:

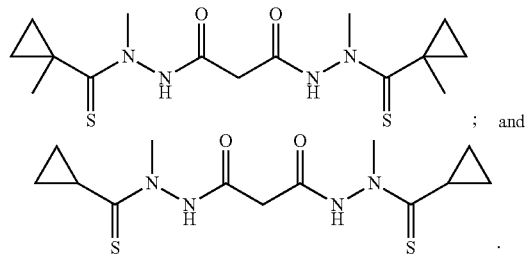

13. The compound of claim 7 represented by the following structural formula:

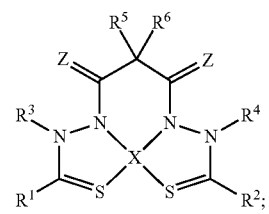

wherein:

X is a transition metal cation with a +2 charge;

$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aryl group;

$R_5$ and $R_6$ are each independently —H, an aliphatic or substituted aliphatic group, or $R_5$ is —H and $R_6$ is an optionally substituted aryl group, or, $R_5$ and $R_6$, taken together, are an optionally substituted $C_2$-$C_6$ alkylene group; and each Z is independently O or S.

14. The compound of claim 13, wherein the compound is greater than 90% pure by weight.

15. The compound of claim 13, wherein X is $Ni^{2+}$, $Cu^{2+}$, $Co^{2+}$, $Fe^{2+}$, $Pt^{2+}$ or $Pd^{2+}$.

16. The compound of claim 13, wherein X is $Cu^{2+}$.

17. The compound of claim 13, wherein:
$R_1$ and $R_2$ are each an optionally substituted phenyl group;
$R_3$ and $R_4$ are each an optionally substituted alkyl group; and
$R_5$ is —H and $R_6$ is —H, an alkyl or substituted alkyl group.

18. The compound of claim 13, wherein:
$R_1$ and $R_2$ are each an optionally substituted aliphatic group; and
$R_3$ and $R_4$ are each an optionally substituted aliphatic group.

19. The compound of claim 18, wherein:
$R_1$ and $R_2$ are both a $C_3$-$C_8$ cycloalkyl group optionally substituted with at least one alkyl group;
$R_3$ and $R_4$ are each an optionally substituted alkyl group; and
$R_5$ is —H and $R_6$ is —H, an alkyl or substituted alkyl group.

20. The compound of claim 13, wherein $R_1$ and $R_2$ are both cyclopropyl or 1-methylcyclopropyl.

21. The compound of claim 1, wherein the compound is represented by a structural formula selected from:

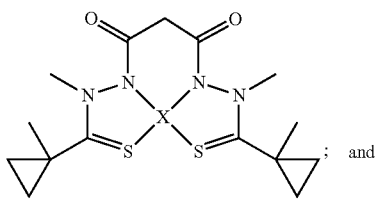 ; and

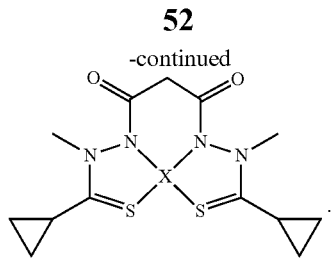

22. A pharmaceutical composition comprising the compound of claim 1 and a pharmaceutically acceptable carrier or diluent.

23. A method of treating a subject with cancer, said method comprising administering to the subject an effective amount of compound of claim 1.

24. A compound comprising a bis[thiohydrazide amide] complexed to a transition metal cation, wherein the bis[thiohydrazide amide] is represented by the following Structural Formula:

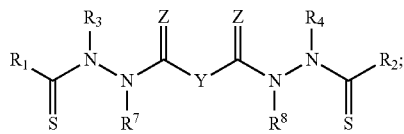

wherein:
$R_1$-$R_4$ are independently —H, an optionally substituted aliphatic group, an optionally substituted aryl group, or $R_1$ and $R_3$ taken together with the carbon and nitrogen atoms to which they are bonded, and/or $R_2$ and $R_4$ taken together with the carbon and nitrogen atoms to which they are bonded, form a non-aromatic heterocyclic ring optionally fused to an aryl group; and Y is a covalent bond of a substituted or unsubstituted straight chained hydrocarbyl group, or Y, taken together with both >C=Z groups to which it is bonded, is a substituted or unsubstituted aryl group;

$R_7$ and $R_8$ are independently —H, an optionally substituted aliphatic group, or an optionally substituted aryl group; and each Z is independently O or S.

* * * * *